US008628782B2

(12) United States Patent
Berkower

(10) Patent No.: US 8,628,782 B2
(45) Date of Patent: Jan. 14, 2014

(54) DELETION OF THE BETA 20-21 LOOP IN HIV GP120 EXPOSES THE CD4 BINDING SITE FOR IMPROVED ANTIBODY BINDING AND ANTIBODY INDUCTION

(75) Inventor: Ira Berkower, Washington, DC (US)

(73) Assignee: The United States of America, as Represented by the Department of Health and Human Services, Washington, DC (US)

( * ) Notice: Subject to any disclaimer, the term of this patent is extended or adjusted under 35 U.S.C. 154(b) by 638 days.

(21) Appl. No.: 12/714,085

(22) Filed: Feb. 26, 2010

(65) Prior Publication Data

US 2010/0215682 A1    Aug. 26, 2010

Related U.S. Application Data

(60) Provisional application No. 61/155,782, filed on Feb. 26, 2009.

(51) Int. Cl.
*A61K 39/21* (2006.01)

(52) U.S. Cl.
USPC ..................................... 424/188.1; 424/208.1

(58) Field of Classification Search
None
See application file for complete search history.

(56) References Cited

PUBLICATIONS

Berkower, I., et al., 2004, Assembly, structure, and antigenic properties of virus-like particles rich in HIV-1 envelope gp120, Virol. 321:75-86.*
Berkower, I., et al., 2008, Targeted deletion in the beta20-beta21 loop of HIV envelope glycoprotein gp120 exposes the CD4 binding site for antibody binding, Virol. 377:330-338.*
Lore, K., et al., 2003, Toll-like receptor ligands modulate dendritic cells to augment cytomegalovirus- and HIV-1-specific T cell responses, J. Immunol. 171:4320-4328.*
Cordonnier, A., et al., 1989, Effects of mutations in hyperconserved regions of the extracellular glycoprotein of human immunodeficiency virus type 1 on receptor binding, J. Virol. 63(10):4464-4468.*
Barouch, D. H., Oct. 2008, Challenges in the development of an HIV-1 vaccine, Nature 455:613-619.*
Burton, D. R., et al., Mar. 2004, HIV vaccine design and the neutralizing antibody problem, Nat. Immunol. 5(3):233-236.*
Haynes, B. F., Jun. 2006, Aiming to induce broadly reactive neutralizing antibody responses with HIV-1 vaccine candidates, Expert Rev. Vaccines 5(3):347-363.*
Walker, B. D., 2008, Toward an AIDS vaccine, Science 320:760-764.*
Berkower et al., "Assembly, structure, and antigenic properties of virus-like particles rich in HIV-1 envelope gp120," *Virology*, vol. 321, pp. 75-86, 2004.
Berkower et al., "Targeted deletion in the β20-β21 loop of HIV envelope glycoprotein gp120 exposes the CD4 binding site for antibody binding," *Virology*, vol. 377, pp. 330-338, 2008.
Cordonnier et al., "Effects of Mutations in Hyperconserved Regions of the Extracellular Glycoprotein of Human Immunodeficiency Virus Type 1 on Receptor Binding," *J. Virol.*, vol. 63, No. 10, pp. 4464-4468, 1989.
Lasky et al., "Delineation of a region of the human immunodeficiency virus type 1 gp120 glycoprotein critical for interaction with CD4 receptor", *Cell*, vol. 50, pp. 975-985, 1987.
Moore and Sweet, ""The HIV gp120-CD4 interaction: A target for pharmacological or immunological intervention?", *Perspectives in Drug Discovery and Design*, vol. 1, pp. 235-250, 1993.
Pantophlet et al., "Fine mapping of the interaction of neutralizing and nonneutralizing monoclonal antibodies with the CD4 binding site of human immunodeficiency virus type 1 gp120", *J. Virol.*, vol. 77, No. 1, pp. 642-658, 2003.
Xiang et al., "Mutagenetic stabilization and/or disruption of a CD4-bound state reveals distinct conformations of the human immunodeficiency virus type 1 gp120 envelope glycoprotein", *J. Virol.*, vol. 76, No. 19, pp. 9888-9899, 2002.
Zhou et al., "Structural definition of a conserved neutralization epitope on HIV-1 gp120", *Nature*, vol. 445, 732-737, 2007.

* cited by examiner

*Primary Examiner* — Jeffrey S. Parkin
(74) *Attorney, Agent, or Firm* — Klarquist Sparkman, LLP

(57) ABSTRACT

Disclosed herein are isolated immunogens including variant gp120 polypeptides. In an example, a variant gp120 polypeptide includes a deletion of at least 8 consecutive residues of the fourth conserved loop (C4) between residues 419 and 434 of gp120 according to HXB2 numbering. Also provided are isolated nucleic acid molecules encoding the disclosed isolated immunogens. In an example, an isolated nucleic acid molecule further includes a nucleic acid molecule encoding a hepatitis B surface antigen or a variant thereof. Compositions including the isolated immunogens including variant gp120 polypeptides are also disclosed. In some examples, a composition further includes a carrier protein, such as a hepatitis B surface antigen or a variant thereof (natural or recombinant). Viral-like particles are also provided including any of the disclosed isolated immunogens or compositions. Also disclosed are uses of these variant gp120 polypeptides and nucleic acids encoding variant polypeptides, such as to induce an immune response to HIV-1.

10 Claims, 9 Drawing Sheets

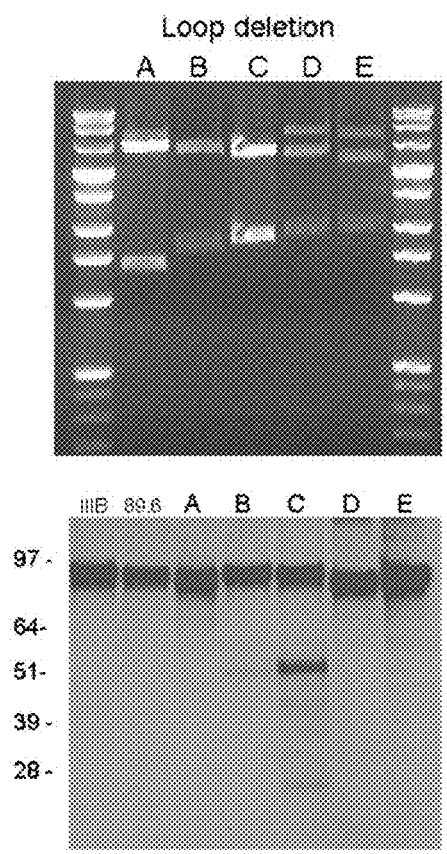
FIG. 2A
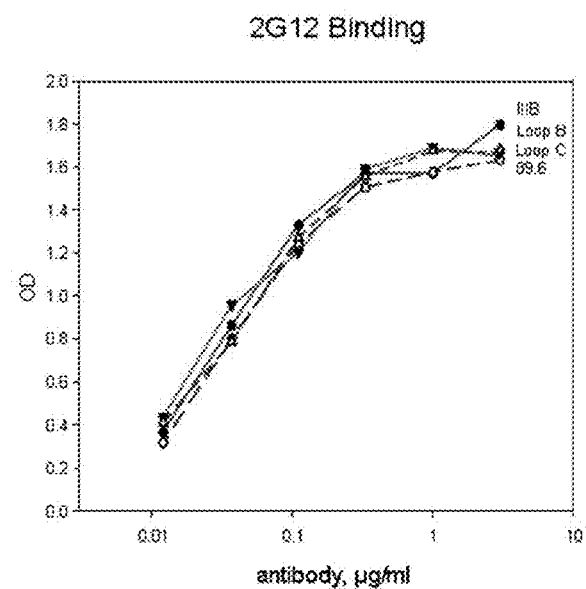
FIG. 2B
FIG. 2C

FIG. 7C  Loop C deletion

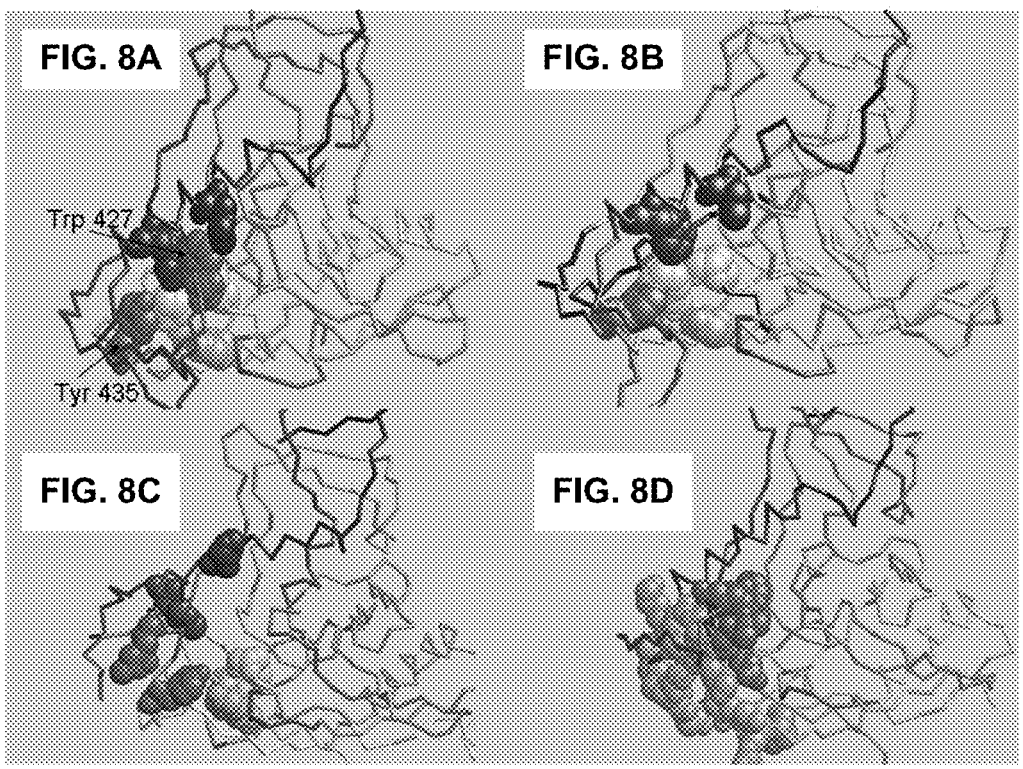

SEQUENCE LISTING

```
<160> NUMBER OF SEQ ID NOS: 58

<210> SEQ ID NO 1
<211> LENGTH: 28
<212> TYPE: PRT
<213> ORGANISM: Artificial sequence
<220> FEATURE:
<223> OTHER INFORMATION: Consensus sequence for MPR of  HIV-1 gp41
<220> FEATURE:
<221> NAME/KEY: MISC_FEATURE
<222> LOCATION: (3)..(4)
<223> OTHER INFORMATION: X can be any naturally occurring amino acid
<220> FEATURE:
<221> NAME/KEY: MISC_FEATURE
<222> LOCATION: (7)..(7)
<223> OTHER INFORMATION: X can be any naturally occurring amino acid

<400> SEQUENCE: 1

Asn Glu Xaa Xaa Leu Leu Xaa Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 2
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 2

Asn Glu Gln Glu Leu Leu Ala Leu Asp Lys Trp Ala Ser Leu Trp Asn
```

```
                1               5                  10                  15
Trp Phe Asp Ile Thr Asn Trp Leu Trp Tyr Ile Lys
                20                  25

<210> SEQ ID NO 3
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 3

Asn Glu Gln Asp Leu Leu Ala Leu Asp Lys Trp Ala Ser Leu Trp Asn
1               5                   10                  15

Trp Phe Asp Ile Thr Asn Trp Leu Trp Tyr Ile Lys
                20                  25

<210> SEQ ID NO 4
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 4

Asn Glu Gln Asp Leu Leu Ala Leu Asp Lys Trp Ala Asn Leu Trp Asn
1               5                   10                  15

Trp Phe Asp Ile Ser Asn Trp Leu Trp Tyr Ile Lys
                20                  25

<210> SEQ ID NO 5
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 5

Asn Glu Gln Asp Leu Leu Ala Leu Asp Lys Trp Ala Asn Leu Trp Asn
1               5                   10                  15

Trp Phe Asn Ile Thr Asn Trp Leu Trp Tyr Ile Arg
                20                  25

<210> SEQ ID NO 6
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 6

Asn Glu Gln Glu Leu Leu Glu Leu Asp Lys Trp Ala Ser Leu Trp Asn
1               5                   10                  15

Trp Phe Asp Ile Thr Asn Trp Leu Trp Tyr Ile Lys
                20                  25

<210> SEQ ID NO 7
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 7

Asn Glu Lys Asp Leu Leu Ala Leu Asp Ser Trp Lys Asn Leu Trp Asn
```

```
                1               5                  10                 15
Trp Phe Asp Ile Thr Asn Trp Leu Trp Tyr Ile Lys
                20                 25

<210> SEQ ID NO 8
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 8

Asn Glu Gln Asp Leu Leu Ala Leu Asp Ser Trp Glu Asn Leu Trp Asn
1               5                  10                 15
Trp Phe Asp Ile Thr Asn Trp Leu Trp Tyr Ile Lys
                20                 25

<210> SEQ ID NO 9
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 9

Asn Glu Gln Glu Leu Leu Glu Leu Asp Lys Trp Ala Ser Leu Trp Asn
1               5                  10                 15
Trp Phe Ser Ile Thr Gln Trp Leu Trp Tyr Ile Lys
                20                 25

<210> SEQ ID NO 10
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 10

Asn Glu Gln Glu Leu Leu Ala Leu Asp Lys Trp Ala Ser Leu Trp Asn
1               5                  10                 15
Trp Phe Asp Ile Ser Asn Trp Leu Trp Tyr Ile Lys
                20                 25

<210> SEQ ID NO 11
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 11

Asn Glu Gln Asp Leu Leu Ala Leu Asp Lys Trp Asp Asn Leu Trp Ser
1               5                  10                 15
Trp Phe Thr Ile Thr Asn Trp Leu Trp Tyr Ile Lys
                20                 25

<210> SEQ ID NO 12
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 12

Asn Glu Gln Asp Leu Leu Ala Leu Asp Lys Trp Ala Ser Leu Trp Asn
```

```
                1               5                  10                  15
Trp Phe Asp Ile Thr Lys Trp Leu Trp Tyr Ile Lys
                20                  25

<210> SEQ ID NO 13
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 13

Asn Glu Gln Asp Leu Leu Ala Leu Asp Lys Trp Ala Ser Leu Trp Asn
1               5                   10                  15
Trp Phe Ser Ile Thr Asn Trp Leu Trp Tyr Ile Lys
                20                  25

<210> SEQ ID NO 14
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 14

Asn Glu Lys Asp Leu Leu Glu Leu Asp Lys Trp Ala Ser Leu Trp Asn
1               5                   10                  15
Trp Phe Asp Ile Thr Asn Trp Leu Trp Tyr Ile Lys
                20                  25

<210> SEQ ID NO 15
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 15

Asn Glu Gln Glu Ile Leu Ala Leu Asp Lys Trp Ala Ser Leu Trp Asn
1               5                   10                  15
Trp Phe Asp Ile Ser Lys Trp Leu Trp Tyr Ile Lys
                20                  25

<210> SEQ ID NO 16
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 16

Asn Glu Gln Asp Leu Leu Ala Leu Asp Lys Trp Ala Asn Leu Trp Asn
1               5                   10                  15
Trp Phe Asn Ile Ser Asn Trp Leu Trp Tyr Ile Lys
                20                  25

<210> SEQ ID NO 17
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 17

Asn Glu Gln Asp Leu Leu Ala Leu Asp Lys Trp Ala Ser Leu Trp Ser
```

```
1               5                   10                  15
Trp Phe Asp Ile Ser Asn Trp Leu Trp Tyr Ile Lys
            20                  25
```

<210> SEQ ID NO 18
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 18

```
Asn Glu Lys Asp Leu Leu Ala Leu Asp Ser Trp Lys Asn Leu Trp Ser
1               5                   10                  15

Trp Phe Asp Ile Thr Asn Trp Leu Trp Tyr Ile Lys
            20                  25
```

<210> SEQ ID NO 19
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 19

```
Asn Glu Gln Glu Leu Leu Gln Leu Asp Lys Trp Ala Ser Leu Trp Asn
1               5                   10                  15

Trp Phe Ser Ile Thr Asn Trp Leu Trp Tyr Ile Lys
            20                  25
```

<210> SEQ ID NO 20
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 20

```
Asn Glu Gln Asp Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25
```

<210> SEQ ID NO 21
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 21

```
Asn Glu Gln Glu Leu Leu Ala Leu Asp Lys Trp Ala Ser Leu Trp Asn
1               5                   10                  15

Trp Phe Asp Ile Ser Asn Trp Leu Trp Tyr Ile Arg
            20                  25
```

<210> SEQ ID NO 22
<211> LENGTH: 28
<212> TYPE: PRT
<213> ORGANISM: Artificial sequence
<220> FEATURE:
<223> OTHER INFORMATION: gp41 MPR peptide variant

<400> SEQUENCE: 22

```
Asn Glu Gln Glu Leu Leu Glu Leu Asp Lys Trp Ala Ser Leu Trp Asn
```

```
1               5                   10                  15
Trp Phe Asn Ile Thr Asn Trp Leu Trp Tyr Ile Lys
            20                  25
```

<210> SEQ ID NO 23
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 23
ctgtgaaatt tatcgatcta attactatgt cttc           34

<210> SEQ ID NO 24
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 24
tgctaaatcg ataatagtac agctaaatga atc            33

<210> SEQ ID NO 25
<211> LENGTH: 22
<212> TYPE: PRT
<213> ORGANISM: Artificial sequence
<220> FEATURE:
<223> OTHER INFORMATION: Consensus sequence for transmembrance spanning
      region of gp41 of HIV-1
<220> FEATURE:
<221> NAME/KEY: MISC_FEATURE
<222> LOCATION: (1)..(1)
<223> OTHER INFORMATION: X can be any naturally occurring amino acid
<220> FEATURE:
<221> NAME/KEY: MISC_FEATURE
<222> LOCATION: (10)..(10)
<223> OTHER INFORMATION: X can be any naturally occurring amino acid
<220> FEATURE:
<221> NAME/KEY: MISC_FEATURE
<222> LOCATION: (18)..(18)
<223> OTHER INFORMATION: X can be any naturally occurring amino acid

<400> SEQUENCE: 25

```
Xaa Phe Ile Met Ile Val Gly Gly Leu Xaa Gly Leu Arg Ile Val Phe
1               5                   10                  15

Thr Xaa Leu Ser Ile Val
            20
```

<210> SEQ ID NO 26
<211> LENGTH: 22
<212> TYPE: PRT
<213> ORGANISM: Artificial sequence
<220> FEATURE:
<223> OTHER INFORMATION: gp41 transmembrane spanning region peptide
      variant

<400> SEQUENCE: 26

```
Ile Phe Ile Met Ile Val Gly Gly Leu Ile Gly Leu Arg Ile Val Phe
1               5                   10                  15

Thr Val Leu Ser Ile Val
            20
```

<210> SEQ ID NO 27
<211> LENGTH: 22
<212> TYPE: PRT
<213> ORGANISM: Artificial sequence

```
<220> FEATURE:
<223> OTHER INFORMATION: gp41 transmembrane spanning region peptide
      variant

<400> SEQUENCE: 27

Leu Phe Ile Met Ile Val Gly Gly Leu Ile Gly Leu Arg Ile Val Phe
1               5                   10                  15

Thr Ala Leu Ser Ile Val
            20

<210> SEQ ID NO 28
<211> LENGTH: 22
<212> TYPE: PRT
<213> ORGANISM: Artificial sequence
<220> FEATURE:
<223> OTHER INFORMATION: gp41 transmembrane spanning region peptide
      variant

<400> SEQUENCE: 28

Ile Phe Ile Met Ile Val Gly Gly Leu Val Gly Leu Arg Ile Val Phe
1               5                   10                  15

Thr Ala Leu Ser Ile Val
            20

<210> SEQ ID NO 29
<211> LENGTH: 276
<212> TYPE: PRT
<213> ORGANISM: Artificial sequence
<220> FEATURE:
<223> OTHER INFORMATION: Synthetic Hepatitis B/HIV-1 peptide

<400> SEQUENCE: 29

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Pro Ile Pro Ser Ser Trp Ala Phe Ala
        195                 200                 205

Lys Tyr Leu Trp Glu Trp Ala Ser Val Arg Phe Ser Trp Leu Ser Leu
    210                 215                 220
```

```
Leu Val Pro Phe Val Gln Trp Phe Val Gly Leu Ser Pro Thr Val Trp
225                 230                 235                 240

Leu Ser Ala Ile Trp Met Met Trp Tyr Trp Gly Pro Ser Leu Tyr Ser
                245                 250                 255

Ile Val Ser Pro Phe Ile Pro Leu Leu Pro Ile Phe Phe Cys Leu Trp
            260                 265                 270

Val Tyr Ile Gly
        275

<210> SEQ ID NO 30
<211> LENGTH: 4
<212> TYPE: PRT
<213> ORGANISM: Artificial sequence
<220> FEATURE:
<223> OTHER INFORMATION: Synthetic peptide

<400> SEQUENCE: 30

Gly Pro Gly Pro
1

<210> SEQ ID NO 31
<211> LENGTH: 226
<212> TYPE: PRT
<213> ORGANISM: Hepatitis B virus

<400> SEQUENCE: 31

Glu Phe Ile Thr Ser Gly Phe Leu Gly Pro Leu Leu Val Leu Gln Ala
1               5                   10                  15

Gly Phe Phe Leu Leu Thr Arg Ile Leu Thr Ile Pro Gln Ser Leu Asp
                20                  25                  30

Ser Trp Trp Thr Ser Leu Asn Phe Leu Gly Gly Ser Pro Val Cys Leu
            35                  40                  45

Gly Gln Asn Ser Gln Ser Pro Thr Ser Asn His Ser Pro Thr Ser Cys
        50                  55                  60

Pro Pro Ile Cys Pro Gly Tyr Arg Trp Met Cys Leu Arg Arg Phe Ile
65                  70                  75                  80

Ile Phe Leu Phe Ile Leu Leu Leu Cys Leu Ile Phe Leu Leu Val Leu
                85                  90                  95

Leu Asp Tyr Gln Gly Met Leu Pro Val Cys Pro Leu Ile Pro Gly Ser
                100                 105                 110

Thr Thr Thr Ser Thr Gly Pro Cys Lys Thr Cys Thr Thr Pro Ala Gln
            115                 120                 125

Gly Asn Ser Lys Phe Pro Ser Cys Cys Cys Thr Lys Pro Thr Asp Gly
        130                 135                 140

Asn Cys Thr Cys Ile Ser Ile Pro Ser Ser Trp Ala Phe Ala Lys Tyr
145                 150                 155                 160

Leu Trp Glu Trp Ala Ser Val Arg Phe Ser Trp Leu Ser Leu Leu Val
                165                 170                 175

Pro Phe Val Gln Trp Phe Val Gly Leu Ser Pro Thr Val Trp Leu Ser
                180                 185                 190

Ala Ile Trp Met Met Trp Tyr Trp Gly Pro Ser Leu Tyr Ser Ile Val
            195                 200                 205

Ser Pro Phe Ile Pro Leu Leu Pro Ile Phe Phe Cys Leu Trp Val Tyr
        210                 215                 220

Ile Gly
225
```

```
<210> SEQ ID NO 32
<211> LENGTH: 15
<212> TYPE: PRT
<213> ORGANISM: Homo sapiens

<400> SEQUENCE: 32

Ala Ser Leu Trp Asn Trp Phe Asn Ile Thr Asn Trp Leu Trp Tyr
1               5                   10                  15

<210> SEQ ID NO 33
<211> LENGTH: 15
<212> TYPE: PRT
<213> ORGANISM: Homo sapiens

<400> SEQUENCE: 33

Ile Lys Leu Phe Ile Met Ile Val Gly Gly Leu Val Gly Leu Arg
1               5                   10                  15

<210> SEQ ID NO 34
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(3)
<223> OTHER INFORMATION: X can be any aliphatic amino acid
<220> FEATURE:
<221> NAME/KEY: MISC_FEATURE
<222> LOCATION: (4)..(4)
<223> OTHER INFORMATION: X can be any naturally occuring amino acid

<400> SEQUENCE: 34

Cys Xaa Xaa Xaa
1

<210> SEQ ID NO 35
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 35
ccatcgattg cttaaagatt attgt                                         25

<210> SEQ ID NO 36
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 36
ccatcgattg taacgcacag tttta                                         25

<210> SEQ ID NO 37
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 37
gccacatatt tgctagctgt tttattctgc attggagtg                          39

<210> SEQ ID NO 38
```

```
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 38
ggcagaaagt agggctagca atgtatgccc c                           31

<210> SEQ ID NO 39
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 39
acctccatcc cgggttagta gcagccctg                              29

<210> SEQ ID NO 40
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 40
gccccggggc ttcagacctg gaggaggaga tatg                        34

<210> SEQ ID NO 41
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 41
ctcctcccgg gcggaagatc tcagtctcag                             30

<210> SEQ ID NO 42
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 42
cgcccgggag gagggacaa ttggagaagt gaattat                      37

<210> SEQ ID NO 43
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 43
ggcccggggg acaattggag aagtg                                  25

<210> SEQ ID NO 44
<211> LENGTH: 271
<212> TYPE: PRT
<213> ORGANISM: Artificial sequence
<220> FEATURE:
<223> OTHER INFORMATION: Synthetic Hepatitis B/HIV-1 peptide

<400> SEQUENCE: 44
```

```
Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Ile Thr Ser Gly
            20                  25                  30

Phe Leu Gly Pro Leu Leu Val Leu Gln Ala Gly Phe Phe Leu Leu Thr
            35                  40                  45

Arg Ile Leu Thr Ile Pro Gln Ser Leu Asp Ser Trp Trp Thr Ser Leu
50                  55                  60

Asn Phe Leu Gly Gly Ser Pro Val Cys Leu Gly Gln Asn Ser Gln Ser
65                  70                  75                  80

Pro Thr Ser Asn His Ser Pro Thr Ser Cys Pro Pro Ile Cys Pro Gly
                85                  90                  95

Tyr Arg Trp Met Cys Leu Arg Arg Phe Ile Ile Phe Leu Phe Ile Leu
                100                 105                 110

Leu Leu Cys Leu Ile Phe Leu Leu Val Leu Leu Asp Tyr Gln Gly Met
            115                 120                 125

Leu Pro Val Cys Pro Leu Ile Pro Gly Ser Thr Thr Thr Ser Thr Gly
            130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Asn
                165                 170                 175

Ile Asn Glu Lys Glu Leu Leu Glu Leu Asp Lys Trp Ala Ser Leu Trp
                180                 185                 190

Asn Trp Phe Asp Ile Thr Asn Trp Leu Trp Tyr Ile Arg Leu Phe Ile
            195                 200                 205

Met Ile Val Gly Gly Leu Ile Gly Leu Arg Ile Val Phe Ala Val Leu
210                 215                 220

Ser Ile Val Val Gly Leu Ser Pro Thr Val Trp Leu Ser Ala Ile Trp
225                 230                 235                 240

Met Met Trp Tyr Trp Gly Pro Ser Leu Tyr Ser Ile Val Ser Pro Phe
                245                 250                 255

Ile Pro Leu Leu Pro Ile Phe Phe Cys Leu Trp Val Tyr Ile Gly
            260                 265                 270

<210> SEQ ID NO 45
<211> LENGTH: 295
<212> TYPE: PRT
<213> ORGANISM: Artificial sequence
<220> FEATURE:
<223> OTHER INFORMATION: Synthetic Hepatitis B/HIV-1 peptide

<400> SEQUENCE: 45

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile

-continued

```
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Pro Ile Asn Glu Lys Glu Leu Leu Glu
        195                 200                 205

Leu Asp Lys Trp Ala Ser Leu Trp Asn Trp Phe Asp Ile Thr Asn Trp
    210                 215                 220

Leu Trp Tyr Ile Arg Leu Phe Ile Met Ile Val Gly Gly Leu Ile Gly
225                 230                 235                 240

Leu Arg Ile Val Phe Ala Val Leu Ser Ile Val Val Gly Leu Ser Pro
                245                 250                 255

Thr Val Trp Leu Ser Ala Ile Trp Met Met Trp Tyr Trp Gly Pro Ser
            260                 265                 270

Leu Tyr Ser Ile Val Ser Pro Phe Ile Pro Leu Leu Pro Ile Phe Phe
        275                 280                 285

Cys Leu Trp Val Tyr Ile Gly
    290                 295

<210> SEQ ID NO 46
<211> LENGTH: 865
<212> TYPE: DNA
<213> ORGANISM: Artificial sequence
<220> FEATURE:
<223> OTHER INFORMATION: Synthetic Hepatitis B/HIV-1 polynucleotide

<400> SEQUENCE: 46
ggtaccgtcg acagcaaaag caggggataa ttctattaac catgaagact atcattgctt      60
tgagctacat ttctgtctg gttttcgccc aagaccttcc aggaaatgac aacaacagcg      120
aattcatcac ctccggcttc ctgggccccc tgctggtcct gcaggccggg ttcttcctgc     180
tgacccgcat cctcaccatc ccccagtccc tggactcgtg gtggacctcc ctcaactttc     240
tggggggctc ccccgtgtgt ctgggccaga actcccagtc ccccacctcc aaccactccc     300
ccacctcctg ccccccccatc tgccccggct accgctggat gtgcctgcgc cgcttcatca    360
tcttcctgtt catcctgctg ctgtgcctga tcttcctgct ggtgctgctg gactaccagg     420
gcatgctgcc cgtgtgcccc ctgatccccg gctccaccac cacctccacc ggcccctgca     480
agacctgcac cacccccgcc cagggcaact ccaagttccc ctcctgctgc tgcaccaagc     540
ccaccgacgg caactgcacc tgcatcaata ttaatgaaaa agaattattg gaattggata     600
aatgggcaag tttgtggaat tggtttgaca taacaaactg gctgtggtat ataagattat     660
tcataatgat agtaggaggc ttgataggtt taagaatagt ttttgctgta ctttctatag     720
tagtgggcct gtcccccacc gtgtggctgt ccgccatctg gatgatgtgg tactggggcc     780
cctccctgta ctccatcgtg tccccccttca tcccccctgct gcccatcttc ttctgcctgt    840
gggtgtacat ctgactagtg agctc                                          865

<210> SEQ ID NO 47


```
<211> LENGTH: 379
<212> TYPE: PRT
<213> ORGANISM: Artificial sequence
<220> FEATURE:
<223> OTHER INFORMATION: HIV-1 gp-41 variant polypeptide

<400> SEQUENCE: 47
```

| | | | | | | | | | | | | | | | |
|---|---|---|---|---|---|---|---|---|---|---|---|---|---|---|---|
| Val | Pro | Val | Trp | Arg | Glu | Ala | Thr | Thr | Thr | Leu | Phe | Cys | Ala | Ser | Asp |
| 1 | | | | 5 | | | | | 10 | | | | | 15 | |
| Ala | Lys | Ala | Tyr | Asp | Thr | Glu | Val | Asn | Trp | Ala | Thr | His | Ala | Cys | Val |
| | | | 20 | | | | | 25 | | | | | 30 | | |
| Pro | Thr | Asp | Pro | Asn | Pro | Glu | Val | Val | Leu | Gly | Asn | Val | Thr | Glu | Asn |
| | | 35 | | | | | 40 | | | | | 45 | | | |
| Phe | Asn | Met | Trp | Lys | Asn | Asn | Met | Val | Asp | Gln | Met | His | Glu | Asp | Ile |
| | 50 | | | | | 55 | | | | | 60 | | | | |
| Ile | Ser | Leu | Trp | Asp | Glu | Ser | Leu | Lys | Pro | Cys | Val | Lys | Leu | Thr | Pro |
| 65 | | | | | 70 | | | | | 75 | | | | | 80 |
| Leu | Ser | Val | Gln | Ala | Cys | Pro | Lys | Val | Ser | Phe | Gln | Pro | Ile | Pro | Ile |
| | | | | 85 | | | | | 90 | | | | | 95 | |
| His | Tyr | Cys | Val | Pro | Ala | Gly | Phe | Ala | Met | Leu | Lys | Cys | Asn | Asn | Lys |
| | | | 100 | | | | | 105 | | | | | 110 | | |
| Thr | Phe | Asn | Gly | Ser | Gly | Pro | Cys | Thr | Asn | Val | Ser | Thr | Val | Gln | Cys |
| | | 115 | | | | | 120 | | | | | 125 | | | |
| Thr | His | Gly | Ile | Arg | Pro | Val | Val | Ser | Thr | Gln | Leu | Leu | Leu | Asn | Gly |
| | 130 | | | | | 135 | | | | | 140 | | | | |
| Ser | Leu | Ala | Glu | Glu | Asp | Ile | Val | Ile | Arg | Ser | Glu | Asn | Phe | Thr | Asp |
| 145 | | | | | 150 | | | | | 155 | | | | | 160 |
| Asn | Ala | Lys | Thr | Ile | Ile | Val | Gln | Leu | Asn | Glu | Ser | Val | Val | Ile | Asn |
| | | | | 165 | | | | | 170 | | | | | 175 | |
| Cys | Thr | Arg | Pro | Asn | Asn | Asn | Thr | Arg | Arg | Leu | Ser | Ile | Gly | Pro |
| | | | 180 | | | | | 185 | | | | | 190 | | |
| Gly | Arg | Ala | Phe | Tyr | Ala | Arg | Arg | Asn | Ile | Ile | Gly | Asp | Ile | Arg | Gln |
| | | 195 | | | | | 200 | | | | | 205 | | | |
| Ala | His | Cys | Asn | Ile | Ser | Arg | Ala | Lys | Trp | Asn | Asn | Thr | Leu | Gln | Gln |
| | 210 | | | | | 215 | | | | | 220 | | | | |
| Ile | Val | Ile | Lys | Leu | Arg | Glu | Lys | Phe | Arg | Asn | Lys | Thr | Ile | Ala | Phe |
| 225 | | | | | 230 | | | | | 235 | | | | | 240 |
| Asn | Gln | Ser | Ser | Gly | Gly | Asp | Pro | Glu | Ile | Val | Met | His | Ser | Phe | Asn |
| | | | | 245 | | | | | 250 | | | | | 255 | |
| Cys | Gly | Gly | Glu | Phe | Phe | Tyr | Cys | Asn | Thr | Ala | Gln | Leu | Phe | Asn | Ser |
| | | | 260 | | | | | 265 | | | | | 270 | | |
| Thr | Trp | Asn | Val | Thr | Gly | Gly | Thr | Asn | Gly | Thr | Glu | Gly | Asn | Asp | Ile |
| | | 275 | | | | | 280 | | | | | 285 | | | |
| Ile | Thr | Leu | Gln | Cys | Arg | Ile | Lys | Gln | Ile | Ile | Asn | Met | Trp | Gln | Lys |
| | 290 | | | | | 295 | | | | | 300 | | | | |
| Val | Gly | Lys | Ala | Met | Tyr | Ala | Pro | Pro | Ile | Thr | Gly | Gln | Ile | Arg | Cys |
| 305 | | | | | 310 | | | | | 315 | | | | | 320 |
| Ser | Ser | Asn | Ile | Thr | Gly | Leu | Leu | Leu | Thr | Arg | Asp | Gly | Gly | Asn | Ser |
| | | | | 325 | | | | | 330 | | | | | 335 | |
| Thr | Glu | Thr | Glu | Thr | Glu | Ile | Phe | Arg | Pro | Gly | Gly | Gly | Asp | Met | Arg |
| | | | 340 | | | | | 345 | | | | | 350 | | |
| Asp | Asn | Trp | Arg | Ser | Glu | Leu | Tyr | Lys | Tyr | Lys | Val | Val | Arg | Ile | Glu |
| | | 355 | | | | | 360 | | | | | 365 | | | |
| Pro | Ile | Gly | Val | Ala | Pro | Thr | Arg | Ala | Lys | Arg | | | | | |
| | 370 | | | | | 375 | | | | | | | | | |

<210> SEQ ID NO 48
<211> LENGTH: 1177
<212> TYPE: DNA
<213> ORGANISM: Artificial sequence
<220> FEATURE:
<223> OTHER INFORMATION: HIV-1 gp-41 variant polynucleotide

<400> SEQUENCE: 48

| | | | | | |
|---|---|---|---|---|---|
| ggtacctgtg | tggagagaag | caaccaccac | tctattttgt | gcatcagatg | ctaaagccta | 60 |
| tgatacagag | gtacataatg | tttgggccac | acatgcctgt | gtacccacag | accccaaccc | 120 |
| acaagaagta | gtattgggaa | atgtgacaga | aaattttaac | atgtggaaaa | ataacatggt | 180 |
| agatcagatg | catgaggata | taatcagttt | atgggatgaa | agcctaaagc | catgtgtaaa | 240 |
| attaacccca | ctctcggtcc | aggcctgtcc | aaaggtatcc | tttcagccaa | ttcccataca | 300 |
| ttattgtgtc | ccggctgggt | tgcgatgct | aaagtgtaac | aataagacat | tcaatggatc | 360 |
| aggaccatgc | acaaatgtca | gcacagtaca | atgtacacat | ggaattaggc | cagtggtgtc | 420 |
| aactcaactg | ctgttaaatg | gcagtctagc | agaagaagac | atagtaatta | gatctgaaaa | 480 |
| tttcacagac | aatgctaaaa | ccataatagt | acagctaaat | gaatctgtag | taattaattg | 540 |
| tacaagaccc | aacaacaata | caagaagaag | gttatctata | ggaccaggga | gagcattta | 600 |
| tgcaagaaga | aacataatag | gagatataag | acaagcacat | tgtaacatta | gtagagcaaa | 660 |
| atggaataac | actttacaac | agatagttat | aaaattaaga | gaaaaattta | ggaataaaac | 720 |
| aatagccttt | aatcaatcct | caggagggga | cccagaaatt | gtaatgcaca | gttttaattg | 780 |
| tggaggggaa | tttttctact | gtaatacagc | acaactgttt | aatagtactt | ggaatgttac | 840 |
| tggagggaca | aatggcactg | aaggaaatga | cataatcaca | ctccaatgca | gaataaaaca | 900 |
| aattataaat | atgtggcaga | agtaggaaaa | agcaatgtat | gcccctccca | tcacaggaca | 960 |
| aattagatgt | tcatcaaata | ttacagggct | gctactaaca | agagatggag | gtaatagtac | 1020 |
| tgagactgag | actgagatct | tcagacctgg | aggaggagat | atgagggaca | attggagaag | 1080 |
| tgaattatat | aaatataaag | tagtaagaat | tgaaccaata | ggagtagcac | ccaccagggc | 1140 |
| aaagagatga | ctagtcgcgg | ccgctttcga | atctaga | | | 1177 |

<210> SEQ ID NO 49
<211> LENGTH: 1141
<212> TYPE: DNA
<213> ORGANISM: Artificial sequence
<220> FEATURE:
<223> OTHER INFORMATION: HIV-1 gp-41 variant polynucleotide

<400> SEQUENCE: 49

| | | | | | |
|---|---|---|---|---|---|
| ggtacctgtg | tggagagaag | caaccaccac | tctattttgt | gcatcagatg | ctaaagccta | 60 |
| tgatacagag | gtacataatg | tttgggccac | acatgcctgt | gtacccacag | accccaaccc | 120 |
| acaagaagta | gtattgggaa | atgtgacaga | aaattttaac | atgtggaaaa | ataacatggt | 180 |
| agatcagatg | catgaggata | taatcagttt | atgggatgaa | agcctaaagc | catgtgtaaa | 240 |
| attaacccca | ctctcggtcc | aggcctgtcc | aaaggtatcc | tttcagccaa | ttcccataca | 300 |
| ttattgtgtc | ccggctgggt | tgcgatgct | aaagtgtaac | aataagacat | tcaatggatc | 360 |
| aggaccatgc | acaaatgtca | gcacagtaca | atgtacacat | ggaattaggc | cagtggtgtc | 420 |
| aactcaactg | ctgttaaatg | gcagtctagc | agaagaagac | atagtaatta | gatctgaaaa | 480 |
| tttcacagac | aatgctaaaa | ccataatagt | acagctaaat | gaatctgtag | taattaattg | 540 |
| tacaagaccc | aacaacaata | caagaagaag | gttatctata | ggaccaggga | gagcattta | 600 |

```
tgcaagaaga aacataatag gagatataag acaagcacat tgtaacatta gtagagcaaa    660
atggaataac actttacaac agatagttat aaaattaaga gaaaaattta ggaataaaac    720
aatagccttt aatcaatcct caggagggga cccagaaatt gtaatgcaca gttttaattg    780 tggagggaa ttttctact gtaatacagc acaactgttt aatagtactt ggaatgttac      840
tggagggaca atggcactg aaggaaatga cataatcaca ctccaatgca gaataaaaca     900
gctagcaatg tatgccccctc ccatcacagg acaaattaga tgttcatcaa atattacagg  960
gctgctacta acaagagatg gaggtaatag tactgagact gagactgaga tcttcagacc   1020
tggaggagga gatatgaggg acaattggag aagtgaatta tataaatata agtagtaag    1080 aattgaacca ataggagtag cacccaccag ggcaaagaga tgactagtcg cggccgcttt   1140
c                                                                   1141
```

<210> SEQ ID NO 50
<211> LENGTH: 373
<212> TYPE: PRT
<213> ORGANISM: Artificial sequence
<220> FEATURE:
<223> OTHER INFORMATION: HIV-1 gp-41 variant polynucleotide

<400> SEQUENCE: 50

```
Val Pro Val Trp Arg Glu Ala Thr Thr Thr Leu Phe Cys Ala Ser Asp
1               5                   10                  15

Ala Lys Ala Tyr Asp Thr Glu Val His Asn Val Trp Ala Thr His Ala
                20                  25                  30

Cys Val Pro Thr Asp Pro Asn Pro Gln Glu Val Val Leu Gly Asn Val
            35                  40                  45

Thr Glu Asn Phe Asn Met Trp Lys Asn Asn Met Val Asp Gln Met His
        50                  55                  60

Glu Asp Ile Ile Ser Leu Trp Asp Glu Ser Leu Lys Pro Cys Val Lys
65                  70                  75                  80

Leu Thr Pro Leu Ser Val Gln Ala Cys Pro Lys Val Ser Phe Gln Pro
                85                  90                  95

Ile Pro Ile His Tyr Cys Val Pro Ala Gly Phe Ala Met Leu Lys Cys
            100                 105                 110

Asn Asn Lys Thr Phe Asn Gly Ser Gly Pro Cys Thr Asn Val Ser Thr
        115                 120                 125

Val Gln Cys Thr His Gly Ile Arg Pro Val Val Ser Thr Gln Leu Leu
    130                 135                 140

Leu Asn Gly Ser Leu Ala Glu Glu Asp Ile Val Ile Arg Ser Glu Asn
145                 150                 155                 160

Phe Thr Asp Asn Ala Lys Thr Ile Ile Val Gln Leu Asn Glu Ser Val
                165                 170                 175

Val Ile Asn Cys Thr Arg Pro Asn Asn Asn Thr Arg Arg Arg Leu Ser
            180                 185                 190

Ile Gly Pro Gly Arg Ala Phe Tyr Ala Arg Arg Asn Ile Ile Gly Asp
        195                 200                 205

Ile Arg Gln Ala His Cys Asn Ile Ser Arg Ala Lys Trp Asn Asn Thr
    210                 215                 220

Leu Gln Gln Ile Val Ile Lys Leu Arg Glu Lys Phe Arg Asn Lys Thr
225                 230                 235                 240

Ile Ala Phe Asn Gln Ser Ser Gly Gly Asp Pro Glu Ile Val Met His
                245                 250                 255

Ser Phe Asn Cys Gly Gly Glu Phe Phe Tyr Cys Asn Thr Ala Gln Leu
            260                 265                 270
```

```
Phe Asn Ser Thr Trp Asn Val Thr Gly Gly Thr Asn Gly Thr Glu Gly
            275                 280                 285

Asn Asp Ile Ile Thr Leu Gln Cys Arg Ile Lys Gln Leu Ala Met Tyr
            290                 295                 300

Ala Pro Pro Ile Thr Gly Gln Ile Arg Cys Ser Ser Asn Ile Thr Gly
305                 310                 315                 320

Leu Leu Leu Thr Arg Asp Gly Gly Asn Ser Thr Glu Thr Glu Thr Glu
            325                 330                 335

Ile Phe Arg Pro Gly Gly Gly Asp Met Arg Asp Asn Trp Arg Ser Glu
            340                 345                 350

Leu Tyr Lys Tyr Lys Val Val Arg Ile Glu Pro Ile Gly Val Ala Pro
            355                 360                 365

Thr Arg Ala Lys Arg
            370

<210> SEQ ID NO 51
<211> LENGTH: 655
<212> TYPE: PRT
<213> ORGANISM: Human immunodeficiency virus type 1

<400> SEQUENCE: 51

Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
            35                  40                  45

Leu Ala Gln Lys Leu Pro Gly Asn Asp Asn Asn Ser Glu Phe Ile Thr
        50                  55                  60

Ser Gly Phe Leu Gly Pro Leu Leu Val Leu Gln Ala Gly Phe Phe Leu
65              70                  75                  80

Leu Thr Arg Ile Leu Thr Ile Pro Gln Ser Leu Asp Ser Trp Trp Thr
            85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
            115                 120                 125

Pro Gly Tyr Arg Met Cys Leu Arg Arg Phe Ile Ile Phe Leu Phe Ile
        130                 135                 140

Leu Leu Leu Cys Leu Ile Phe Leu Leu Val Leu Leu Asp Tyr Gln Gly
145                 150                 155                 160

Met Leu Pro Val Cys Pro Leu Ile Pro Gly Ser Thr Thr Thr Ser Thr
            165                 170                 175

Gly Pro Cys Lys Thr Cys Thr Thr Pro Ala Gln Gly Asn Ser Lys Phe
            180                 185                 190

Pro Ser Cys Cys Cys Thr Lys Pro Thr Asp Gly Asn Cys Thr Cys Ile
            195                 200                 205

Pro Ile Pro Ser Ser Trp Ala Phe Ala Lys Tyr Leu Trp Glu Trp Ala
        210                 215                 220

Ser Val Arg Phe Ser Trp Leu Ser Leu Leu Val Pro Phe Val Gln Trp
225                 230                 235                 240

Phe Val Gly Leu Ser Pro Thr Val Trp Leu Ser Ala Ile Trp Met Met
            245                 250                 255

Trp Tyr Trp Gly Pro Ser Leu Tyr Ser Ile Val Ser Pro Phe Ile Pro
            260                 265                 270
```

```
Leu Leu Pro Ile Phe Phe Cys Leu Trp Val Tyr Ile Gly Val Pro Val
            275                 280                 285

Trp Lys Glu Ala Thr Thr Thr Leu Phe Cys Ala Ser Asp Ala Lys Ala
        290                 295                 300

Tyr Asp Thr Glu Val His Asn Val Trp Ala Thr His Ala Cys Val Pro
305                 310                 315                 320

Thr Asp Pro Asn Pro Gln Glu Val Val Leu Glu Asn Val Thr Glu His
                325                 330                 335

Phe Asn Met Trp Lys Asn Asn Met Val Glu Gln Met Gln Glu Asp Ile
            340                 345                 350

Ile Ser Leu Trp Asp Gln Ser Leu Lys Pro Cys Val Lys Leu Thr Pro
        355                 360                 365

Leu Gln Ala Cys Pro Lys Ile Ser Phe Glu Pro Ile Pro Ile His Tyr
    370                 375                 380

Cys Ala Pro Ala Gly Phe Ala Ile Leu Lys Cys Asn Asp Lys Thr Phe
385                 390                 395                 400

Asn Gly Lys Gly Pro Cys Lys Asn Val Ser Thr Val Gln Cys Thr His
                405                 410                 415

Gly Ile Arg Pro Val Val Ser Thr Gln Leu Leu Leu Asn Gly Ser Leu
            420                 425                 430

Ala Glu Glu Glu Val Val Ile Arg Ser Asp Asn Phe Thr Asn Asn Ala
        435                 440                 445

Lys Thr Ile Ile Val Gln Leu Lys Glu Ser Val Glu Ile Asn Cys Thr
    450                 455                 460

Arg Pro Asn Asn Asn Thr Arg Lys Ser Ile His Ile Gly Pro Gly Arg
465                 470                 475                 480

Ala Phe Tyr Thr Thr Gly Glu Ile Ile Gly Asp Ile Arg Gln Ala His
                485                 490                 495

Cys Asn Ile Ser Arg Ala Lys Trp Asn Asp Thr Leu Lys Gln Ile Val
            500                 505                 510

Ile Lys Leu Arg Glu Gln Phe Glu Asn Lys Thr Ile Val Phe Asn His
        515                 520                 525

Ser Ser Gly Gly Asp Pro Glu Ile Val Met His Ser Phe Asn Cys Gly
    530                 535                 540

Gly Glu Phe Phe Tyr Cys Asn Ser Thr Gln Leu Phe Asn Ser Thr Trp
545                 550                 555                 560

Asn Asn Asn Thr Glu Gly Ser Asn Asn Thr Glu Gly Asn Thr Ile Thr
                565                 570                 575

Leu Pro Cys Arg Ile Lys Gln Leu Ala Met Tyr Ala Pro Pro Ile Arg
            580                 585                 590

Gly Gln Ile Arg Cys Ser Ser Asn Ile Thr Gly Leu Leu Leu Thr Arg
        595                 600                 605

Asp Gly Gly Ile Asn Glu Asn Gly Thr Glu Ile Phe Arg Pro Gly Gly
    610                 615                 620

Gly Asp Met Arg Asp Asn Trp Arg Ser Glu Leu Tyr Lys Tyr Lys Val
625                 630                 635                 640

Val Lys Ile Glu Pro Leu Gly Val Ala Pro Thr Lys Ala Lys Arg
                645                 650                 655

<210> SEQ ID NO 52
<211> LENGTH: 2000
<212> TYPE: DNA
<213> ORGANISM: Human immunodeficiency virus type 1

<400> SEQUENCE: 52
```

```
ggattattca taccgtccca ccatcgggcg cggatcccgg tccgaagcgc gcggaattca      60
aaggcctacg tcgacagcaa aagcagggga taattctatt aaccatgaag actatcattg     120
ctttgagcta cattttatgt ctggttctcg ctcaaaaact tcccggaaat gacaacaaca     180
gcgaattcat cacctccggc ttcctgggcc ccctgctggt gctgcaggcc ggcttcttcc     240
tgctgacccg catcctgacc atcccccagt ccctggactc ctggtggacc tccctgaact     300
tcctgggcgg ctcccccgtg tgcctgggcc agaactccca gtcccccacc tccaaccact     360
cccccacctc ctgcccccccc atctgccccg ctaccgctg gatgtgcctg cgccgcttca     420
tcatcttcct gttcatcctg ctgctgtgcc tgatcttcct gctggtgctg ctggactacc     480
agggcatgct gcccgtgtgc ccctgatcc ccggctccac caccacctcc accggcccct     540
gcaagacctg caccaccccc gcccagggca actccaagtt cccctcctgc tgctgcacca     600
agcccaccga cggcaactgc acctgcatcc ccatccccte ctcctgggcc ttcgccaagt     660
acctgtggga gtgggcctcc gtgcgcttct cctggctgtc cctgctggtg ccttcgtgc      720 agtggttcgt gggcctgtcc ccaccgtgt ggctgtccgc catctggatg atgtggtact     780
ggggcccctc cctgtactcc atcgtgtccc ccttcatccc cctgctgccc atcttcttct     840
gcctgtgggt gtacatcggg gtacctgtgt ggaaagaagc aaccaccact ctattttgtg     900
catcagatgc taaagcatat gatacagagg tacataatgt ttgggccaca catgcctgtg     960
tacccacaga ccccaaccca caagaagtag tattggaaaa tgtaacagaa cattttaaca    1020
tgtggaaaaa taacatggta gaacagatgc aggaggatat aatcagttta tgggatcaaa    1080
gcctaaagcc atgtgtaaaa ttaaccccac tccaggcctg tccaaagata cctttgagc     1140 caattcccat acattattgt gccccggctg gttttgcgat tctaaagtgt aatgataaga    1200
cgttcaatgg aaaaggacca tgtaaaaatg tcagcacagt acaatgtaca catggaatta    1260
ggccagtagt atcaactcaa ctgctgctaa atggcagtct agcagaagaa gaggtagtaa    1320
ttagatctga caatttcacg aacaatgcta aaaccataat agtacagctg aaagaatctg    1380
tagaaattaa ttgtacaaga cccaacaaca atacaagaaa aagtatacat ataggaccag    1440
ggagagcatt ttatactaca ggagaaataa taggagatat aagacaagca cattgtaaca    1500
ttagtagagc aaaatggaat gacactttaa aacagatagt tataaaatta agagaacaat    1560
ttgagaataa aacaatagtc tttaatcact cctcaggagg ggacccagaa attgtaatgc    1620
acagttttaa ttgtggagga gaattttttct actgtaattc aacacaactg tttaatagta    1680
cttggaataa taatactgaa gggtcaaata cactgaagg aaatactatc acactcccat    1740
gcagaataaa acagctagca atgtatgccc ctcccatcag aggacaaatt agatgttcat    1800
caaatattac agggctgcta ttaacaagag atggtggtat taatgagaat gggaccgaga    1860
tcttcagacc tggaggagga gatatgaggg acaattggag aagtgaatta tataaatata    1920
aagtagtaaa aattgaacca ttaggagtag cacccaccaa ggcaaagaga tgactagtcg    1980
cggccgcttt cgaatctaga                                                 2000
```

<210> SEQ ID NO 53
<211> LENGTH: 663
<212> TYPE: PRT
<213> ORGANISM: Human immunodeficiency virus type 1

<400> SEQUENCE: 53

```
Ile Ile His Thr Val Pro Pro Ser Gly Ala Asp Pro Gly Pro Lys Arg
1               5                   10                  15
```

-continued

```
Ala Glu Phe Lys Gly Leu Arg Arg Gln Gln Lys Gln Gly Ile Ile Leu
         20                  25                  30

Leu Thr Met Lys Thr Ile Ile Ala Leu Ser Tyr Ile Leu Cys Leu Val
         35                  40                  45

Leu Ala Gln Lys Leu Pro Gly Asn Asp Asn Asn Ser Glu Phe Ile Thr
 50                  55                  60

Ser Gly Phe Leu Gly Pro Leu Leu Val Leu Gln Ala Gly Phe Phe Leu
 65                  70                  75                  80

Leu Thr Arg Ile Leu Thr Ile Pro Gln Ser Leu Asp Ser Trp Trp Thr
                 85                  90                  95

Ser Leu Asn Phe Leu Gly Gly Ser Pro Val Cys Leu Gly Gln Asn Ser
                100                 105                 110

Gln Ser Pro Thr Ser Asn His Ser Pro Thr Ser Cys Pro Pro Ile Cys
            115                 120                 125

Pro Gly Tyr Arg Trp Met Cys Leu Arg Arg Phe Ile Ile Phe Leu Phe
            130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser
                165                 170                 175

Thr Gly Pro Cys Lys Thr Cys Thr Thr Pro Ala Gln Gly Asn Ser Lys
                180                 185                 190

Phe Pro Ser Cys Cys Cys Thr Lys Pro Thr Asp Gly Asn Cys Thr Cys
            195                 200                 205

Ile Pro Ile Pro Ser Ser Trp Ala Phe Ala Lys Tyr Leu Trp Glu Trp
210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
            260                 265                 270

Pro Leu Leu Pro Ile Phe Phe Cys Leu Trp Val Tyr Ile Gly Val Pro
            275                 280                 285

Val Trp Lys Glu Ala Thr Thr Thr Leu Phe Cys Ala Ser Asp Ala Lys
290                 295                 300

Ala Tyr Asp Thr Glu Val His Asn Val Trp Ala Thr His Ala Cys Val
305                 310                 315                 320

Pro Thr Asp Pro Asn Pro Gln Glu Val Val Leu Glu Asn Val Thr Glu
                325                 330                 335

Asn Phe Asn Met Trp Lys Asn Asn Met Val Glu Gln Met His Glu Asp
            340                 345                 350

Ile Ile Ser Leu Trp Asp Gln Ser Leu Lys Pro Cys Val Lys Leu Thr
            355                 360                 365

Pro Leu Gln Ala Cys Pro Lys Val Ser Phe Glu Pro Ile Pro Ile His
            370                 375                 380

Tyr Cys Thr Pro Ala Gly Phe Ala Ile Leu Lys Cys Lys Asp Lys Lys
385                 390                 395                 400

Phe Asn Gly Thr Gly Pro Cys Lys Asn Val Ser Thr Val Gln Cys Thr
                405                 410                 415

His Gly Ile Arg Pro Val Val Ser Thr Gln Leu Leu Leu Asn Gly Ser
            420                 425                 430

Leu Ala Glu Glu Glu Val Val Ile Arg Ser Ser Asn Phe Thr Asp Asn
            435                 440                 445
```

| Ala | Lys | Asn | Ile | Ile | Val | Gln | Leu | Lys | Glu | Ser | Val | Glu | Ile | Asn | Cys |
| --- | --- | --- | --- | --- | --- | --- | --- | --- | --- | --- | --- | --- | --- | --- | --- |
| | 450 | | | | 455 | | | | | 460 | | | | | |
| Thr | Arg | Pro | Asn | Asn | Asn | Thr | Arg | Lys | Ser | Ile | His | Ile | Gly | Pro | Gly |
| 465 | | | | | 470 | | | | | 475 | | | | | 480 |
| Arg | Ala | Phe | Tyr | Thr | Thr | Gly | Glu | Ile | Ile | Gly | Asp | Ile | Arg | Gln | Ala |
| | | | | 485 | | | | | 490 | | | | | 495 | |
| His | Cys | Asn | Ile | Ser | Arg | Thr | Lys | Trp | Asn | Asn | Thr | Leu | Asn | Gln | Ile |
| | | | | 500 | | | | | 505 | | | | | 510 | |
| Ala | Thr | Lys | Leu | Lys | Glu | Gln | Phe | Gly | Asn | Asn | Lys | Thr | Ile | Val | Phe |
| | | 515 | | | | | 520 | | | | | 525 | | | |
| Asn | Gln | Ser | Ser | Gly | Gly | Asp | Pro | Glu | Ile | Val | Met | His | Ser | Phe | Asn |
| 530 | | | | | 535 | | | | | 540 | | | | | |
| Cys | Gly | Gly | Glu | Phe | Phe | Tyr | Cys | Asn | Ser | Thr | Gln | Leu | Phe | Asn | Ser |
| 545 | | | | | 550 | | | | | 555 | | | | | 560 |
| Thr | Trp | Asn | Phe | Asn | Gly | Thr | Trp | Asn | Leu | Thr | Gln | Ser | Asn | Gly | Thr |
| | | | | 565 | | | | | 570 | | | | | 575 | |
| Glu | Gly | Asn | Asp | Thr | Ile | Thr | Leu | Pro | Cys | Arg | Ile | Lys | Gln | Leu | Ala |
| | | | 580 | | | | | 585 | | | | | 590 | | |
| Met | Tyr | Ala | Pro | Pro | Ile | Arg | Gly | Gln | Ile | Arg | Cys | Ser | Ser | Asn | Ile |
| | | 595 | | | | | 600 | | | | | 605 | | | |
| Thr | Gly | Leu | Ile | Leu | Thr | Arg | Asp | Gly | Gly | Asn | His | Asn | Asn | Asp |
| | 610 | | | | | 615 | | | | | 620 | | | | |
| Thr | Glu | Thr | Phe | Arg | Pro | Gly | Gly | Gly | Asp | Met | Arg | Asp | Asn | Trp | Arg |
| 625 | | | | | 630 | | | | | 635 | | | | | 640 |
| Ser | Glu | Leu | Tyr | Lys | Tyr | Lys | Val | Val | Lys | Ile | Glu | Pro | Leu | Gly | Val |
| | | | | 645 | | | | | 650 | | | | | 655 | |
| Ala | Pro | Thr | Lys | Ala | Lys | Arg |
| | | | 660 | | | |

<210> SEQ ID NO 54
<211> LENGTH: 2000
<212> TYPE: DNA
<213> ORGANISM: Human immunodeficiency virus type 1

<400> SEQUENCE: 54

```
ggattattca taccgtccca ccatcgggcg cggatcccgg tccgaagcgc gcggaattca      60
aaggcctacg tcgacagcaa aagcagggga taattctatt aaccatgaag actatcattg     120
ctttgagcta catttatgt ctggttctcg ctcaaaaact tcccggaaat gacaacaaca     180
gcgaattcat cacctccggc ttcctgggcc cctgctggt gctgcaggcc ggcttcttcc     240
tgctgacccg catcctgacc atcccccagt ccctggactc ctggtggacc tccctgaact     300
tcctgggcgg ctcccccgtg tgcctgggcc agaactccca gtcccccacc tccaaccact     360
ccccacctc ctgccccccc atctgccccg gctaccgctg gatgtgcctg cgccgcttca     420
tcatcttcct gttcatcctg ctgctgtgcc tgatcttcct gctggtgctg ctggactacc     480
agggcatgct gccgtgtgc ccctgatcc ccggctccac caccacctcc accggcccct     540
gcaagacctg caccacccc gcccagggca actccaagtt cccctcctgc tgctgcacca     600
agcccaccga cggcaactgc acctgcatcc ccatcccctc ctcctgggcc ttcgccaagt     660
acctgtggga gtgggcctcc gtgcgcttct cctggctgtc cctgctggtg cccttcgtgc     720
agtggttcgt gggcctgtcc ccaccgtgt ggctgtccgc catctggatg atgtggtact     780
ggggcccctc cctgtactcc atcgtgtccc ccttcatccc cctgctgccc atcttcttct     840
gcctgtgggt gtacatcggg gtacctgtgt ggaaagaagc aaccaccact ctattttgtg     900
```

```
catcagatgc taaagcatat gatacagagg tacataatgt ttgggccaca catgcctgtg     960
tacccacaga ccccaaccca caagaagtag tattggaaaa tgtgacagaa aattttaaca    1020
tgtggaaaaa taacatggta gaacagatgc atgaggatat aatcagttta tgggatcaaa    1080
gcctaaagcc atgtgtaaaa ttaaccccac tccaggcctg tccaaggta tcctttgagc     1140 caattcccat acattattgt accccggctg gttttgcgat tctaaagtgt aaagacaaga    1200
agttcaatgg aacagggcca tgtaaaaatg tcagcacagt acaatgtaca catggaatta    1260
ggccagtagt gtcaactcaa ctgctgttaa atggcagtct agcagaagaa gaggtagtaa    1320
ttagatctag taatttcaca gacaatgcaa aaaacataat agtacagttg aaagaatctg    1380
tagaaattaa ttgtacaaga cccaacaaca atacaaggaa agtatacat ataggaccag     1440 gaagagcatt ttatacaaca ggagaaataa taggagatat aagacaagca cattgcaaca    1500
ttagtagaac aaaatggaat aacactttaa atcaaatagc tacaaaatta aaagaacaat    1560
ttgggaataa taaaacaata gtctttaatc aatcctcagg aggggaccca gaaattgtaa    1620
tgcacagttt taattgtgga ggggaattttt ctactgtaa ttcaacacaa ctgtttaata    1680
gtacttggaa ttttaatggt acttggaatt taacacaatc gaatggtact gaaggaaatg    1740
acactatcac actcccatgt agaataaaac agctagcaat gtatgcccct cccatcagag    1800
gacaaattag atgctcatca aatattacag ggctaatatt aacaagagat ggtgaaata    1860 accacaataa tgataccgag acctttagac ctggaggagg agatatgagg gacaattgga    1920
gaagtgaatt atataaatat aaagtagtaa aaattgaacc attaggagta gcacccacca    1980
aggcaaaaag atgactagtc                                               2000

<210> SEQ ID NO 55
<211> LENGTH: 656
<212> TYPE: PRT
<213> ORGANISM: Human immunodeficiency virus type 1

<400> SEQUENCE: 55

Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Asn Ser Glu Phe Ile Thr
    50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
        115                 120                 125

Pro Gly Tyr Arg Trp Met Cys Leu Arg Arg Phe Ile Ile Phe Leu Phe
    130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser
                165                 170                 175
```

```
Thr Gly Pro Cys Lys Thr Cys Thr Thr Pro Ala Gln Gly Asn Ser Lys
            180                 185                 190

Phe Pro Ser Cys Cys Thr Lys Pro Thr Asp Gly Asn Cys Thr Cys
        195                 200                 205

Ile Pro Ile Pro Ser Ser Trp Ala Phe Ala Lys Tyr Leu Trp Glu Trp
        210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
            260                 265                 270

Pro Leu Leu Pro Ile Phe Phe Cys Leu Trp Val Tyr Ile Gly Val Pro
        275                 280                 285

Val Trp Lys Glu Ala Thr Thr Thr Leu Phe Cys Ala Ser Asp Ala Lys
        290                 295                 300

Ala Tyr Asp Thr Glu Val His Asn Val Trp Ala Thr His Ala Cys Val
305                 310                 315                 320

Pro Thr Asp Pro Asn Pro Gln Glu Val Glu Leu Glu Asn Val Thr Glu
                325                 330                 335

Asn Phe Asn Met Trp Lys Asn Asn Met Val Glu Gln Met His Glu Asp
            340                 345                 350

Ile Ile Ser Leu Trp Asp Gln Ser Leu Lys Pro Cys Val Lys Leu Thr
        355                 360                 365

Pro Leu Gln Ala Cys Pro Lys Ile Ser Phe Glu Pro Ile Pro Ile His
        370                 375                 380

Tyr Cys Ala Pro Ala Gly Phe Ala Ile Leu Lys Cys Lys Asp Lys Lys
385                 390                 395                 400

Phe Asn Gly Lys Gly Pro Cys Ser Asn Val Ser Thr Val Gln Cys Thr
                405                 410                 415

His Gly Ile Arg Pro Val Val Ser Thr Gln Leu Leu Leu Asn Gly Ser
            420                 425                 430

Leu Ala Glu Glu Glu Val Val Ile Arg Ser Glu Asn Phe Ala Asp Asn
        435                 440                 445

Ala Lys Thr Ile Ile Val Gln Leu Asn Glu Ser Val Glu Ile Asn Cys
        450                 455                 460

Thr Arg Pro Asn Asn Asn Thr Arg Lys Ser Ile His Ile Gly Pro Gly
465                 470                 475                 480

Arg Ala Leu Tyr Thr Thr Gly Glu Ile Ile Gly Asp Ile Arg Gln Ala
                485                 490                 495

His Cys Asn Leu Ser Arg Ala Lys Trp Asn Asp Thr Leu Asn Lys Ile
            500                 505                 510

Val Ile Lys Leu Arg Glu Gln Phe Gly Asn Lys Thr Ile Val Phe Lys
        515                 520                 525

His Ser Ser Gly Gly Asp Pro Glu Ile Val Thr His Ser Phe Asn Cys
        530                 535                 540

Gly Gly Glu Phe Phe Tyr Cys Asn Ser Thr Gln Leu Phe Asn Ser Thr
545                 550                 555                 560

Trp Asn Val Thr Glu Glu Ser Asn Asn Thr Val Glu Asn Asn Thr Ile
                565                 570                 575

Thr Leu Pro Cys Arg Ile Lys Gln Leu Ala Met Tyr Ala Pro Pro Ile
            580                 585                 590

Arg Gly Gln Ile Arg Cys Ser Ser Asn Ile Thr Gly Leu Leu Leu Thr
        595                 600                 605
```

```
Arg Asp Gly Gly Pro Glu Asp Asn Lys Thr Glu Val Phe Arg Pro Gly
    610                 615                 620

Gly Gly Asp Met Arg Asp Asn Trp Arg Ser Glu Leu Tyr Lys Tyr Lys
625                 630                 635                 640

Val Val Lys Ile Glu Pro Leu Gly Val Ala Pro Thr Lys Ala Lys Arg
                645                 650                 655

<210> SEQ ID NO 56
<211> LENGTH: 2000
<212> TYPE: DNA
<213> ORGANISM: Human immunodeficiency virus type 1

<400> SEQUENCE: 56
ggattattca taccgtccca ccatcgggcg cggatcccgg tccgaagcgc gcggaattca    60
aaggcctacg tcgacagcaa aagcagggga taattctatt aaccatgaag actatcattg   120
ctttgagcta cattttatgt ctggttctcg ctcaaaaact ccccggaaat gacaacaaca   180
gcgaattcat cacctccggc ttcctgggcc ccctgctggt gctgcaggcc ggcttcttcc   240
tgctgacccg catcctgacc atcccccagt ccctggactc ctggtggacc tccctgaact   300
tcctgggcgg ctcccccgtg tgcctgggcc agaactccca gtcccccacc tccaaccact   360
cccccacctc ctgcccccccc atctgccccg gctaccgctg gatgtgcctg cgccgcttca   420
tcatcttcct gttcatcctg ctgctgtgcc tgatcttcct gctggtgctg ctggactacc   480
agggcatgct gccccgtgtgc ccctgatcc ccggctccac caccacctcc accggcccct   540
gcaagacctg caccacccc gcccagggca actccaagtt cccctcctgc tgctgcacca   600
agcccaccga cggcaactgc acctgcatcc ccatcccctc ctcctgggcc ttcgccaagt   660
acctgtggga gtgggcctcc gtgcgcttct cctggctgtc cctgctggtg cccttcgtgc   720
agtggttcgt gggcctgtcc cccaccgtgt ggctgtccgc catctggatg atgtggtact   780
ggggcccctc cctgtactcc atcgtgtccc ccttcatccc cctgctgccc atcttcttct   840
gcctgtgggt gtacatcggg gtacctgtgt ggaaagaagc aaccaccact ctattttgtg   900
catcagatgc taaagcatat gatacagagg tacataatgt ttgggccaca catgcctgtg   960
tacccacaga ccccaaccca caagaagtag aattggaaaa tgtgacagaa aattttaaca  1020
tgtggaaaaa taacatggta gaacagatgc atgaggatat aatcagttta tgggatcaaa  1080
gcctaaagcc atgtgtaaaa ttaactccac tccaggcctg tccaaagata tcctttgagc  1140
caattcccat acattattgt gccccggctg gttttgcgat tctaaagtgt aaagataaga  1200
agttcaatgg aaaaggacca tgttcaaatg tcagcacagt acaatgtaca catgggatta  1260
ggccagtagt atcaactcaa ctgctgttaa atggcagtct agcagaagaa gaggtagtaa  1320
ttagatccga aaatttcgcg gacaatgcta aaaccataat agtacagctg aatgaatctg  1380
tagaaattaa ttgtacaaga cccaacaaca atacaagaaa aagtatacat ataggaccag  1440
gcagagcatt atatacaaca ggagaaataa taggagatat aagacaagca cattgtaacc  1500
ttagtagagc aaaatggaat gacactttaa ataagtagt tataaaatta agagaacaat  1560
ttgggaataa aacaatagtc tttaagcatt cctcaggagg gacccagaa attgtgacgc  1620 acagttttaa ttgtggaggg gaattttttct actgtaattc aacacaactg tttaatagta  1680
cttggaatgt tactgaagag tcaaataaca ctgtagaaaa taacacaatc acactcccat  1740
gcagaataaa acagctagca atgtatgccc ctcccatcag aggacaaatt agatgttcat  1800
caaatattac agggctgcta ttaacaagag atggtggtcc agaggacaac aagaccgagg  1860
```

-continued

```
tcttcagacc tggaggagga gatatgaggg acaattggag aagtgaatta tataaatata    1920
aagtagtaaa aattgaacca ttaggagtag cacccaccaa ggcaaagaga tgactagtcg    1980
cggccgcttt cgaatctaga                                                2000
```

<210> SEQ ID NO 57
<211> LENGTH: 665
<212> TYPE: PRT
<213> ORGANISM: Human immunodeficiency virus type 1

<400> SEQUENCE: 57

```
Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Ser Glu Phe Ile Thr
    50                  55                  60

Ser Gly Phe Leu Gly Pro Leu Leu Val Leu Gln Ala Gly Phe Phe Leu
65              70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
        115                 120                 125

Pro Gly Tyr Arg Trp Met Cys Leu Arg Arg Phe Ile Ile Phe Leu Phe
    130                 135                 140

Ile Leu Leu Leu Cys Leu Ile Phe Leu Leu Val Leu Leu Asp Tyr Gln
145             150                 155                 160

Gly Met Leu Pro Val Cys Pro Leu Ile Pro Gly Ser Thr Thr Thr Ser
                165                 170                 175

Thr Gly Pro Cys Lys Thr Cys Thr Thr Pro Ala Gln Gly Asn Ser Lys
            180                 185                 190

Phe Pro Ser Cys Cys Cys Thr Lys Pro Thr Asp Gly Asn Cys Thr Cys
        195                 200                 205

Ile Pro Ile Pro Ser Ser Trp Ala Phe Ala Lys Tyr Leu Trp Glu Trp
    210                 215                 220

Ala Ser Val Arg Phe Ser Trp Leu Ser Leu Leu Val Pro Phe Val Gln
225             230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
            260                 265                 270

Pro Leu Leu Pro Ile Phe Phe Cys Leu Trp Val Tyr Ile Gly Val Pro
        275                 280                 285

Val Trp Lys Glu Ala Thr Thr Thr Leu Phe Cys Ala Ser Asp Ala Lys
    290                 295                 300

Ala Tyr Asp Thr Glu Val His Asn Val Trp Ala Thr His Ala Cys Val
305             310                 315                 320

Pro Thr Asp Pro Asn Pro Gln Glu Val Val Leu Val Asn Val Thr Glu
                325                 330                 335

Asn Phe Asn Met Trp Lys Asn Asp Met Val Glu Gln Met His Glu Asp
            340                 345                 350
```

Ile Ile Ser Leu Trp Asp Gln Ser Leu Lys Pro Cys Val Lys Leu Thr
            355                 360                 365

Pro Leu Ser Val Gln Ala Cys Pro Lys Val Ser Phe Glu Pro Ile Pro
        370                 375                 380

Ile His Tyr Cys Ala Pro Ala Gly Phe Ala Ile Leu Lys Cys Asn Asn
385                 390                 395                 400

Lys Thr Phe Asn Gly Thr Gly Pro Cys Thr Asn Val Ser Thr Val Gln
                405                 410                 415

Cys Thr His Gly Ile Arg Pro Val Val Ser Thr Gln Leu Leu Leu Asn
            420                 425                 430

Gly Ser Leu Ala Glu Glu Glu Val Val Ile Arg Ser Val Asn Phe Thr
        435                 440                 445

Asp Asn Ala Lys Thr Ile Ile Val Gln Leu Asn Thr Ser Val Glu Ile
450                 455                 460

Asn Cys Thr Arg Pro Ser Val Asn Phe Thr Asp Asn Ala Lys Thr Ile
465                 470                 475                 480

Ile Val Gln Leu Asn Thr Ser Val Glu Ile Asn Cys Thr Arg Pro Met
                485                 490                 495

Arg Gln Ala His Cys Asn Ile Ser Arg Ala Lys Trp Asn Asn Thr Leu
            500                 505                 510

Lys Gln Ile Ala Ser Lys Leu Arg Glu Gln Phe Gly Asn Asn Lys Thr
        515                 520                 525

Ile Ile Phe Lys Gln Ser Ser Gly Gly Asp Pro Glu Ile Val Thr His
        530                 535                 540

Ser Phe Asn Cys Gly Gly Glu Phe Phe Tyr Cys Asn Ser Thr Gln Leu
545                 550                 555                 560

Phe Asn Ser Thr Trp Phe Asn Ser Thr Trp Ser Thr Glu Gly Ser Asn
                565                 570                 575

Asn Thr Glu Gly Ser Asp Thr Ile Thr Leu Pro Cys Arg Ile Lys Gln
            580                 585                 590

Ser Ile Ala Met Tyr Ala Pro Pro Ile Ser Gly Gln Ile Arg Cys Ser
        595                 600                 605

Ser Asn Ile Thr Gly Leu Leu Leu Thr Arg Asp Gly Gly Asn Ser Asn
        610                 615                 620

Asn Glu Ser Glu Ile Phe Arg Pro Gly Gly Asp Met Arg Asp Asn
625                 630                 635                 640

Trp Arg Ser Glu Leu Tyr Lys Tyr Lys Val Val Lys Ile Glu Pro Leu
                645                 650                 655

Gly Val Ala Pro Thr Lys Ala Lys Arg
            660                 665

<210> SEQ ID NO 58
<211> LENGTH: 2000
<212> TYPE: DNA
<213> ORGANISM: Human immunodeficiency virus type 1

<400> SEQUENCE: 58
ggattattca taccgtccca ccatcgggcg cggatcccgg tccgaagcgc gcggaattca      60
aaggcctacg tcgacagcaa agcagggga taattctatt aaccatgaag actatcattg     120
ctttgagcta cattttatgt ctggttctcg ctcaaaaact ccccggaaat gacaacaaca     180
gcgaattcat cacctccggc ttcctgggcc cctgctggt gctgcaggcc ggcttcttcc     240
tgctgacccg catcctgacc atccccagt ccctggactc ctggtggacc tccctgaact     300 tcctgggcg ctcccccgtg tgcctggcc agaactccca gtcccccacc tccaaccact     360

-continued

```
cccccacctc ctgccccccc atctgccccg gctaccgctg gatgtgcctg cgccgcttca    420
tcatcttcct gttcatcctg ctgctgtgcc tgatcttcct gctggtgctg ctggactacc    480
agggcatgct gcccgtgtgc cccctgatcc ccggctccac caccacctcc accggcccct    540
gcaagacctg caccaccccc gcccagggca actccaagtt cccctcctgc tgctgcacca    600
agcccaccga cggcaactgc acctgcatcc ccatcccctc ctcctgggcc ttcgccaagt    660
acctgtggga gtgggcctcc gtgcgcttct cctggctgtc cctgctggtg cccttcgtgc    720
agtggttcgt gggcctgtcc cccaccgtgt ggctgtccgc catctggatg atgtggtact    780
ggggcccctc cctgtactcc atcgtgtccc ccttcatccc cctgctgccc atcttcttct    840
gcctgtgggt gtacatcggg gtacctgtgt ggaaggaagc aaccaccact ctattttgtg    900
catcagatgc taaagcatat gatacagagg tacataatgt ttgggccaca catgcctgtg    960
tacccacaga ccccaaccca caagaagtag tattggtaaa tgtgacagaa aattttaaca   1020
tgtggaaaaa tgacatggta gaacagatgc atgaggatat aatcagttta tgggatcaaa   1080
gcctaaagcc atgtgtaaaa ttaaccccac tctcggtcca ggcctgtcca aaggtatcct   1140
ttgagccaat tcccatacat tattgtgccc cggctggttt tgcgattcta aaatgtaata   1200
ataagacgtt caatggaaca ggaccatgta caaatgtcag cacagtacaa tgtacacatg   1260
gaattaggcc agtagtatca actcaactgc tgttaaatgg cagtctagca gaagaagagg   1320
tagtaattag atctgtcaat ttcacggaca atgctaaaac cataatagta cagctgaaca   1380
catctgtaga aattaattgt acaagaccct ctgtcaattt cacggacaat gctaaaacca   1440
taatagtaca gctgaacaca tctgtagaaa ttaattgtac aagacccatg agacaagcac   1500
attgtaacat tagtagagca aaatggaata acactttaaa acagatagct agcaaattaa   1560
gagaacaatt tggaaataat aaaacaataa tctttaagca atcctcagga ggggacccag   1620
aaattgtaac gcacagtttt aattgtggag gggaattttt ctactgtaat tcaacacaac   1680
tgtttaatag tacttggttt aatagtactt ggagtactga agggtcaaat aacactgaag   1740
gaagtgacac aatcaccctc ccatgcagaa taaaacaatc gatagcaatg tatgcccctc   1800
ccatcagtgg acaaattaga tgttcatcaa atattacagg gctgctatta acaagagatg   1860
gtggtaatag caacaatgag tccgagatct tcagacctgg aggaggagat atgagggaca   1920
attggagaag tgaattatat aaatataaag tagtaaaaat tgaaccatta ggagtagcac   1980
ccaccaaggc aaagagataa                                                 2000
```

DELETION OF THE BETA 20-21 LOOP IN HIV GP120 EXPOSES THE CD4 BINDING SITE FOR IMPROVED ANTIBODY BINDING AND ANTIBODY INDUCTION

CROSS REFERENCE TO RELATED APPLICATION

This application claims the benefit of and priority to U.S. Provisional Application No. 61/155,782 filed on Feb. 26, 2009 which is incorporated herein by reference in its entirety.

FIELD

This disclosure relates to the field of human immunodeficiency virus (HIV), specifically to the use of HIV-1 envelope epitopes, such as glycoprotein 41 (gp41) and glycoprotein 120 (120), to induce an immune response, including a protective immune response.

BACKGROUND

Acquired immune deficiency syndrome (AIDS) is recognized as one of the greatest health threats facing modern society. Treatments for HIV-infected individuals as well as the development of vaccines to protect against infection are urgently needed. One difficulty has been in eliciting neutralizing antibodies to the virus.

The HIV-1 envelope glycoproteins (gp120 and gp41), which mediate receptor binding and entry, are the major targets for neutralizing antibodies. Although the envelope glycoproteins are immunogenic and induce a variety of antibodies, the neutralizing antibodies that are induced are strain-specific, and the majority of the immune response is diverted to non-neutralizing determinants (Weiss, R. A., et al., *Nature*, 316 (6023): 69-72, 1985; Wyatt, R. and J. Sodroski, *Science*, 280 (5371): 1884-1888, 1998). Broadly neutralizing monoclonal antibodies have been isolated only rarely from natural HIV infection. For example, only three gp41-directed neutralizing antibodies (2F5, 4E10 and Z13) and a few gp120-directed neutralizing antibodies have been identified to date.

The HIV envelope spike mediates binding to receptors and virus entry (Wyatt and Sodroski, *Science* 280:188, 1998). The spike is trimeric and composed of three gp120 exterior and three gp41 transmembrane envelope glycoproteins. CD4 binding to gp120 in the spike induces conformational changes that allow binding to a coreceptor, either CCR5 or CXCR4, which is required for viral entry (Dalgleish et al., *Nature* 312:763, 1984; Sattentau and Moore, *J. Exp. Med.* 174:407, 1991; Feng at al., *Science* 272:872, 1996; Wu et al., *Nature* 384:179, 1996; and Trkola et al., *Nature* 384:184, 1996).

The mature gp120 glycoprotein is approximately 470-490 amino acids long depending on the HIV strain of origin. N-linked glycosylation at approximately 20 to 25 sites makes up nearly half of the mass of the molecule. Sequence analysis shows that the polypeptide is composed of five conserved regions (C1-C5) and five regions of high variability (V1-V5).

With the number of individuals infected with HIV-I approaching 1% of the world's population, an effective vaccine is urgently needed. As an enveloped virus, HIV-I hides most of its proteins and genes from humoral recognition behind a protective lipid bilayer. An available exposed viral target for neutralizing antibodies is the envelope spike. Genetic, immunologic and structural studies of the HIV-I envelope glycoproteins have revealed extraordinary diversity as well as multiple overlapping mechanisms of humoral evasion, including self-masquerading glycan, immunodominant variable loops, and conformational masking. These evolutionarily-honed barriers of antigenic diversity and immune evasion have confounded traditional means of vaccine development. It is believed that immunization with effectively immunogenic HIV gp120 envelope glycoprotein can elicit a neutralizing response directed against gp120, and thus HIV. The need exists for immunogens that are capable of eliciting a protective immune response in a suitable subject. In order to be effective, the antibodies raised must be capable of neutralizing a broad range of HIV strains and subtypes.

SUMMARY

Humans can produce cross reactive neutralizing antibodies to HIV-1 in response to infection, as found in polyclonal sera and human monoclonal antibodies such as b12, F105, and 2G12, specific for gp120, as well as monoclonal antibodies 2F5 and 4E10, specific for gp41. These antibodies target conserved epitopes on the envelope glycoproteins gp120 and gp41 that are shared among diverse HIV isolates. Yet, immunization with these glycoproteins has failed so far to elicit broadly neutralizing antibodies, and this difficulty is considered one of the major obstacles to HIV vaccine development. Despite immunizing with gp120 as close as possible to the native form on the virus, the resulting antibodies tend to be specific for unique determinants on the immunizing strain, rather than conserved determinants that could protect against a broad spectrum of strains in circulation.

Under selective pressure, the virus may have developed structures that partially conceal vital envelope domains and protect the virus against broadly neutralizing antibodies. The CD4 binding site (CD4BS) performs essential viral functions during receptor binding and cell entry, but it also defines a neutralizing surface on gp120 which is a target of immunity. Since these functions are shared among all HIV-1 isolates, the sequences are relatively conserved, and antibodies specific for this site can neutralize a broad spectrum of HIV-1 strains. However, because this surface of gp120 it is surrounded by loop structures, this site is blocked from antibody binding. By removing these loops, the site could be exposed for improved antibody binding. In earlier studies, point mutations were created for more than eighty residues in gp120, and each mutant was carefully analyzed for positive or negative effects on antibody binding. However, the change of a single amino acid may be too subtle to enhance antibody binding to a sterically-protected CD4BS. Similarly, it may not alter the protein sufficiently to favor the conformation that exposes the CD4BS for antibody binding.

Disclosed herein are targeted deletions of the loops surrounding the CD4BS that were large enough to expose the CD4BS or to overcome conformational barriers to antibody binding. Deletion of multiple amino acids in the β20-β21 loop gave enhanced antibody binding to the CD4BS, both for a monoclonal that depends strongly on the protein conformation and for one that is relatively insensitive to it. As disclosed herein, molecular modeling suggests that deletion of this loop may improve antibody binding both by reducing steric hindrance and by altering the protein conformation to expose the CD4BS. The same features that prevent antibody binding could also interfere with induction of antibodies to conserved neutralizing determinants. However, the disclosed variant gp120 polypeptides have surprisingly improved antibody binding to the CD4BS and provide novel immunogens capable of eliciting antibodies to this broadly shared neutralizing determinant.

In one embodiment, a variant gp120 includes a gp120 polypeptide with a deletion of at least 8 consecutive residues of the fourth conserved loop (C4) between residues 419 and 434 of gp120 according to HXB2 numbering. In one example, a variant gp120 polypeptide is a gp120 polypeptide in which at least 8 consecutive residues, such as between 8-12, 8-11, 8-10, or 8-9 (for example, 9, 10, 11 or 12) consecutive residues of C4 between residues 419 and 434 of gp120 of SEQ ID NO: 47 have been deleted. In a particular example, a variant gp120 polypeptide includes a gp120 polypeptide in which residues 424-432 are deleted. Additional variant gp120 polypeptides include deletions of INMWQKVGK (residues 424-432 of SEQ ID NO: 47), INMWQKVGKA (residues 424-433 of SEQ ID NO: 47), INMWQKVGKAM (residues 424-434 of SEQ ID NO: 47), RIKQIINMWQKVGK (residues 419-432 of SEQ ID NO: 47), IKQIINMWQKVGK (residues 420-432 of SEQ ID NO: 47), KQIINMWQKVGK (residues 421-432 of SEQ ID NO: 47), QIINMWQKVGK (residues 422-432 of SEQ ID NO: 47), or IINMWQKVGK (residues 423-432 of SEQ ID NO: 47). In other embodiments, variant gp120 polypeptides include combinations of the amino and carboxyl ends between residues 419 and 434.

Isolated nucleic acid molecules encoding the disclosed isolated immunogens, such as nucleic acid molecules encoding a disclosed variant gp120 polypeptide are also provided, as well as host cells transformed with the nucleic acid molecules and viral-like particles produced by the transformed host cells. Additionally, compositions including the disclosed isolated immunogens including a variant gp120 polypeptide are disclosed. In an example, a composition can further include a carrier protein, such as a hepatitis B surface antigen (HBsAg) or variants thereof. In one particular example, the composition includes a wildtype HBsAg.

Viral-like particles including the variant gp120 polypeptides are also provided herein. For example, viral-like particles including variant gp120-HBsAg hybrid constructs are disclosed. In an example, a disclosed viral-like particle further includes at least one TLR ligand. Compositions comprising the viral-like particles are also provided.

The disclosed isolated immunogens including a variant gp120 polypeptide and/or HBsAgs can be used to induce an immune response, such as a protective immune response, when introduced into a subject. The isolated immunogen can also be used in assays to diagnose an HIV infection. Thus, methods are provided for inhibiting HIV infection in a subject, for inducing an immune response to HIV in a subject, for diagnosing HIV infection in a subject, and for identifying a B cell that produces antibodies that bind to gp120.

The foregoing and other features of the disclosure will become more apparent from the following detailed description, which proceeds with reference to the accompanying figures.

BRIEF DESCRIPTION OF THE DRAWINGS

FIGS. 2A-2C are digital images illustrating a DNA gel, a Western blot and a graph showing expression of loop-deleted forms of gp120. FIG. 2A shows the results of a restriction digest of plasmid DNA coding for the loop-deleted mutants. Each mutant was cut from Sal I at the 5'end of the expression cassette to the new restriction site at the deletion, resulting in progressively longer fragments for loops A through E. FIG. 2C shows the results of a Western blot of each gp120 mutant using 2G12 to detect gp120 expression. FIG. 2B shows equal 2G12 binding that indicates equal ELISA plate coating for two wild type gp120s (IIIB and 89.6) and for loop B (on IIIB background) or loop C (on 89.6 background) deletion mutants.

FIGS. 7A-7C are digital images of a graphical representation and analysis of surface properties (GRASP) surface representation of the surface charge density of gp120 including the surface charge density of 89.6 gp120 (FIG. 7B), loop C deleted gp120 (FIG. 7C) and monoclonal antibody b12 (FIG. 7A). The antibody, like CD4 and F105, has an elevated hydrophobic center surrounded by a weakly basic rim. This fits well into the hydrophobic pocket and surrounding negative charge of gp120 in the liganded conformation, and even better in the expanded pocket and more diffuse negative charge of the loop C deletion.

FIGS. 8A-D are digital images of gp120. Hydrophobic CD4 binding pocket of wild type gp120 (FIG. 8A) in the liganded conformation has at least seven aromatic groups. The pocket persists in the loop C deletion mutant (FIG. 8B), and in gp120 in complex with b12 (FIG. 8C). Aromatic residues from loop C from the a1 helix and from the outer sheet are illustrated in FIG. 8D. Loop C is located directly between the CD4 binding pocket on its right and the coreceptor binding site on its left, where it may coordinate CD4 binding and co-receptor function.

BRIEF DESCRIPTION OF SEQUENCES

Figure 1A:
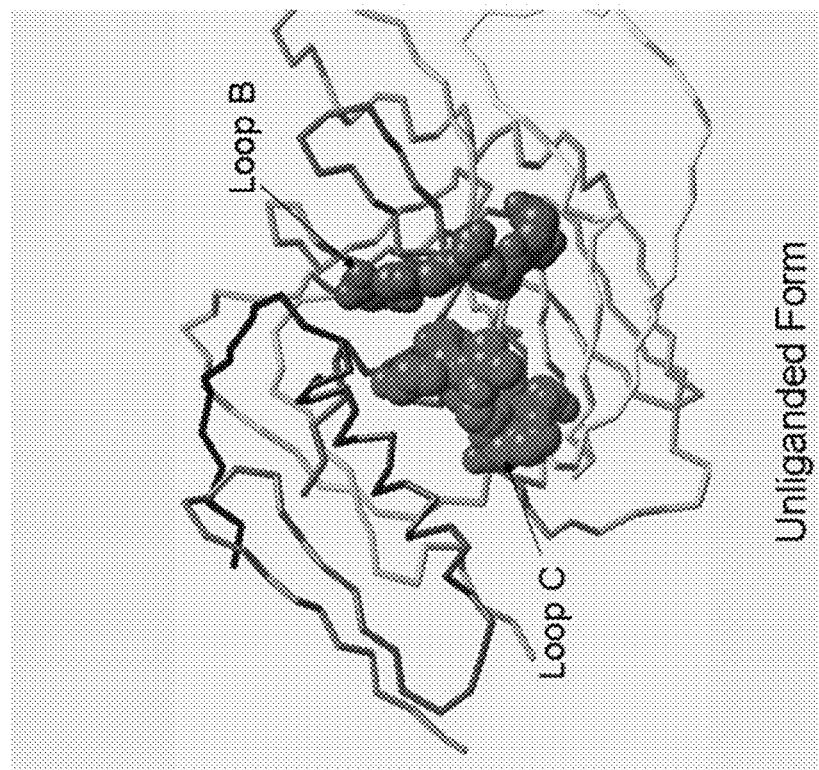
FIGS. 1A and 1B are digital images of the structure of a gp120 model based on unliganded SIV and CD4-bound HIV IIIB. Loops B and C cover the CD4 binding site in the unliganded form (FIG. 1B), but migrate relative to the a1 helix and rotate to expose the CD4B site (CD4BS) for ligand binding (FIG. 1A).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the designated date. In the accompanying sequence listing:

SEQ ID NO: 1 is a consensus amino acid sequence for the membrane proximal region (MPR) of gp41 of HIV-1. An X represents specific amino acids where alterations can be tolerated in which any amino acid may be present.

SEQ ID NOs: 2-22 are exemplary amino acid sequences that can be included within disclosed antigenic polypeptides.

SEQ ID NOs: 23-24 are oligonucleotide primers used to generate variant gp120 immunogens.

SEQ ID NO: 25 is a consensus amino acid sequence for the transmembrane spanning region of gp41. An X represents specific amino acids where alterations can be tolerated.

SEQ ID NOs: 26-28 are exemplary amino acid sequences for a transmembrane spanning region of gp41.

SEQ ID NO: 29 is an amino acid sequence for a disclosed isolated immunogen in which the first transmembrane domain of hepatitis B surface antigen is replaced with the MPR and transmembrane domain of gp41.

SEQ ID NO: 30 is the linker sequence including amino acids GPGP.

SEQ ID NO: 31 is an amino acid sequence of an exemplary wildtype HBsAg.

SEQ ID NO: 32 is an example of a nucleotide sequence for a T helper cell epitope.

SEQ ID NO: 33 is an example of an amino acid sequence for a T helper cell epitope.

SEQ ID NO: 34 is the CAAX amino acid sequence, where C is cystein, A is an aliphatic amino acid and X is any amino acid.

SEQ ID NOs: 35-43 are oligonucleotide primers used to generate variant gp120 immunogens.

SEQ ID NO: 44 is an amino acid sequence for a disclosed isolated immunogen in which the third transmembrane domain of hepatitis B surface antigen is replaced with the MPR and transmembrane domain of gp41.

SEQ ID NO: 45 is an amino acid sequence for a disclosed isolated immunogen in which the first and third transmembrane domains of hepatitis B surface antigen are each replaced with the MPR and transmembrane domain of gp41.

SEQ ID NO: 46 is a nucleic acid sequence for a disclosed isolated immunogen in which the third transmembrane domains of HBsAg is replaced with the MPR and transmembrane domain of gp41.

SEQ ID NO: 47 is an amino acid sequence of a variant gp120 with a V1V2 deleted gp120.

SEQ ID NO: 48 is a nucleic acid sequence of a variant gp120 with a V1V2 deleted gp120.

SEQ ID NO: 49 is a nucleic acid sequence of a variant gp120 polypeptide with a V1V2 deleted gp120 with a beta 20-21 loop deletion.

SEQ ID NO: 50 is an amino acid sequence for a variant gp120 with a V1V2 deletion with a beta 20-21 loop deletion.

SEQ ID NO: 51 is an amino acid sequence for a variant gp120 from HIV isolate JR-FL.

SEQ ID NO: 52 is a nucleic acid sequence for a variant gp120 from HIV isolate JR-FL.

SEQ ID NO: 53 is an amino acid sequence for a variant gp120 from HIV isolate AD8.

SEQ ID NO: 54 is a nucleic acid sequence for a variant gp120 from HIV isolate AD8.

SEQ ID NO: 55 is an amino acid sequence for a variant gp120 from HIV isolate BaL.

SEQ ID NO: 56 is a nucleic acid sequence for a variant gp120 from HIV isolate BaL.

SEQ ID NO: 57 is an amino acid sequence for a variant gp120 from HIV isolate IIIB.

SEQ ID NO: 58 is a nucleic acid sequence for a variant gp120 from HIV isolate IIB.

DETAILED DESCRIPTION

I. Terms and Abbreviations
A. Abbreviations
ADCC: antibody dependent cell cytotoxicity
AIDS: acquired immune deficiency syndrome
CTL: cytotoxic T lymphocyte
ELISA: enzyme linked immunosorbent assay
GP41: glycoprotein 41
GP120: glycoprotein 120
HBsAg: hepatitis B surface antigen
HIV: human immunodeficiency virus
MHC: major histocompatibility complex
MPR: membrane proximal region
PCR: polymerase chain reaction
TLR: toll like receptor
VLP: virus-like particle
B. Terms Unless otherwise noted, technical terms are used according to conventional usage. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Terms describing protein structure and structural elements of proteins can be found in Creighton, Proteins, Structures and Molecular Properties, W.H. Freeman & Co., New York, 1993 (ISBN 0-717-7030) which is incorporated by reference herein in its entirety.

The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

Although methods and materials similar or equivalent to those described herein can be used in the practice or testing of this disclosure, suitable methods and materials are described below. The term "comprises" means "includes." In case of conflict, the present specification, including explanations of terms, will control. In addition, the materials, methods, and examples are illustrative only and not intended to be limiting.

To facilitate review of the various embodiments of this disclosure, the following explanations of specific terms are provided:

Adjuvant: A vehicle used to enhance antigenicity; such as a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants (for example see U.S. Pat. Nos. 6,194,388; 6,207,646; 6,214,806; 6,218,371; 6,239,116; 6,339,068; 6,406,705; and 6,429,199). In some examples, an adjuvant is included in the disclosed pharmaceutical formulations.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term is used interchangeably with the term "immunogen." The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. In one embodiment, T cells respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as, 9, 10, 12 or 15 amino acids. The amino acids are in a unique spatial conformation. Methods of determining spatial conformation of epitopes include, for example, x-ray crystallography and multi-dimensional nuclear magnetic resonance spectroscopy. The term "antigen" denotes both subunit antigens, (for example, antigens which are separate and discrete from a whole organism with which the antigen is associated in nature), as well as killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

An "antigen," when referring to a protein, includes a protein with modifications, such as deletions, additions and substitutions (generally conservative in nature) to the native sequence, so long as the protein maintains the ability to elicit an immunological response, as defined herein. These modifications may be deliberate, as through site-directed mutagenesis, or may be accidental, such as through mutations of hosts which produce the antigens. In some examples, gp120 or a variant thereof, such as gp120 variants disclosed herein are antigens.

Antigen Delivery Platform or Epitope Mounting Platform: In the context of the present disclosure, the terms "antigen delivery platform" and "epitope mounting platform" refer to a macromolecular complex including one or more antigenic epitopes. Delivery of an antigen (including one or more epitopes) in the context of an epitope mounting platform enhances, increases, ameliorates or otherwise improves a desired antigen-specific immune response to the antigenic epitope(s). The molecular constituents of the antigen delivery platform may be antigenically neutral or may be immunologically active, that is, capable of generating a specific immune response. Nonetheless, the term antigen delivery platform is utilized to indicate that a desired immune response is generated against a selected antigen that is a component of the macromolecular complex other than the platform polypeptide to which the antigen is attached. Accordingly, the epitope mounting platform is useful for delivering a wide variety of antigenic epitopes, including antigenic epitopes of pathogenic organisms such as bacteria and viruses, for example surface glycoproteins of HIV such as gp41 or gp120. The antigen delivery platform of the present disclosure is particularly useful for the delivery of complex peptide or polypeptide antigens, which may include one or many distinct epitopes. In some examples, an antigen delivery platform is a HBsAg or a variant HBsAg, or a virus like particle (VLP) that includes an HBsAg or variant thereof.

Antibody: Immunoglobulin molecules and immunologically active portions of immunoglobulin molecules, that is, molecules that contain an antigen binding site that specifically binds (immunoreacts with) an antigen.

A naturally occurring antibody (e.g., IgG, IgM, or IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989) which consists of a $V_H$ domain; (v) an isolated complimentarity determining region (CDR); and (vi) a $F(ab')_2$ fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, *Current Protocols in Immunology* Wiley/Greene, NY, 1991; and Harlow and Lane, *Antibodies: A Laboratory Manual* Cold Spring Harbor Press, NY,1989; Stites et al., (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y. 1986; and Kohler and Milstein, *Nature* 256: 495-497, 1975. Other suitable techniques for antibody preparation include selection of libraries of recombinant antibodies in phage or similar vectors. See, Huse et al., *Science* 246: 1275-1281, 1989; and Ward et al., *Nature* 341: 544-546, 1989. "Specific" monoclonal and polyclonal antibodies and antisera (or antiserum) will usually bind with a $K_D$ of at least about 0.1 µM, preferably at least about 0.01 µM or better, and most typically and preferably, 0.001 µM or better.

Immunoglobulins and certain variants thereof are known and many have been prepared in recombinant cell culture (e.g., see U.S. Pat. Nos. 4,745,055; 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), *Antibody Engineering*, 2nd Edition Freeman and Company, NY, 1995; McCafferty et al., *Antibody Engineering, A Practical Approach*, IRL at Oxford Press, Oxford, England, 1996, and Paul *Antibody Engineering Protocols* Humana Press, Towata, N.J., 1995.

Animal: Living multi-cellular vertebrate organisms, a category that includes, for example, mammals and birds. The term mammal includes both human and non-human mammals. Similarly, the term "subject" includes both human and veterinary subjects.

Antigenic gp120 polypeptide: An "antigenic gp120 polypeptide" includes a gp120 molecule or a portion thereof that is capable of provoking an immune response in a mammal, such as a mammal with or without an HIV infection. Administration of an antigenic gp120 polypeptide that provokes an immune response preferably leads to protective immunity against HIV. In some examples, an antigenic gp120 polypeptide is a conserved loop 4 (C4) deletion mutant.

Antigenic surface: A surface of a molecule, for example a protein such as a gp120 protein or polypeptide, capable of eliciting an immune response. An antigenic surface includes the defining features of that surface, for example the three-dimensional shape and the surface charge. An antigenic surface includes both surfaces that occur on gp120 polypeptides as well as surfaces of compounds that mimic the surface of a gp120 polypeptide (mimetics).

Carrier: An immunogenic macromolecule to which a molecule, such as, for example, a gp120 variant, can be bound. When bound to a carrier, the bound molecule becomes more immunogenic. Carriers are chosen to increase the immunogenicity of the bound molecule and/or to elicit antibodies against the carrier that are diagnostically, analytically, and/or therapeutically beneficial. Covalent linking of a molecule to a carrier confers enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. In some examples, HBsAg is used as a carrier.

Examples of bacterial products useful as carriers include bacterial toxins, such as B. anthracis protective antigen (including fragments that contain at least one antigenic epitope, and analogs or derivatives capable of eliciting an immune response), lethal factor and lethal toxin, and other bacterial toxins and toxoids, such as tetanus toxin/toxoid, diphtheria toxin/toxoid, *P. aeruginosa* exotoxin/toxoid, pertussis toxin/toxoid, and *C. perfringens* exotoxin/toxoid. Additional bacterial products for use as carriers include bacterial wall proteins and other products (for example, streptococcal or staphylococcal cell walls and LPS). Viral proteins, such as hepatitis B surface antigen and core antigen, can also be used as carriers, as well as other viral proteins capable of self assembly.

CD4: Cluster of differentiation factor 4 polypeptide, a T-cell surface protein that mediates interaction with the MHC class II molecule. CD4 also serves as the primary receptor site for HIV on T-cells during HIV-I infection. The known sequence of the CD4 precursor has a hydrophobic signal peptide, an extracelluar region of approximately 370 amino acids, a highly hydrophobic stretch with significant identity to the membrane-spanning domain of the class II MHC beta chain, and a highly charged intracellular sequence of 40 resides (Maddon, *Cell* 42: 93, 1985).

CD4BS antibodies: Antibodies that bind to or substantially overlap the CD4 binding surface of a gp120 polypeptide. The antibodies interfere with or prevent CD4 from binding to a gp120 polypeptide.

CD4i antibodies: Antibodies that bind to a conformation of gp120 induced by CD4 binding.

Contacting: Placement in direct physical association; includes both in solid and liquid form.

Conservative variants: "Conservative" amino acid substitutions are those substitutions that do not substantially affect or decrease a desired activity of a protein or polypeptide. For example, in the context of the present disclosure, a conservative amino acid substitution does not substantially alter or decrease the immunogenicity of an antigenic epitope. Similarly, a conservative amino acid substitution does not substantially affect the structure or, for example, the stability of a protein or polypeptide. Specific, non-limiting examples of a conservative substitution include the following examples:

| Original Residue | Conservative Substitutions |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity or substantially alter a structure, such as a secondary or tertiary structure, of a protein or polypeptide. In some examples the resides of gp120, such as a disclosed gp120 variant that has the C4 loop deleted is substituted at certain positions with conservative amino acids.

Degenerate variant: A polynucleotide encoding a polypeptide or an antibody that includes a sequence that is degenerate as a result of the genetic code. For example, a polynucleotide encoding a gp120 polypeptide or an antibody that binds gp120 that includes a sequence that is degenerate as a result of the genetic code. There are 20 natural amino acids, most of which are specified by more than one codon. Therefore, all degenerate nucleotide sequences are included as long as the amino acid sequence of the gp120 polypeptide or antibody that binds gp120 encoded by the nucleotide sequence is unchanged. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified within a protein encoding sequence, the codon can be altered to any of the corresponding codons described without altering the encoded protein. Such nucleic acid variations are "silent variations," which are one species of conservative variations. Each nucleic acid sequence herein that encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Epitope: An antigenic determinant. These are particular chemical groups or peptide sequences on a molecule that are antigenic, that is, that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8-10 amino acids in a unique spatial conformation. Methods of determining spatial conformation of epitopes include, for example, x-ray crystallography and multi-dimensional nuclear magnetic resonance spectroscopy. See, e.g., "Epitope Mapping Protocols" in *Methods in Molecular Biology*, Vol. 66, Glenn E. Morris, Ed (1996). In one embodiment, an epitope binds an MHC molecule, e.g., an HLA molecule or a DR molecule. These molecules bind polypeptides having the correct anchor amino acids separated by about eight or nine amino acids. In some examples an epitope has a defined antigenic surface, such as the surface defined by the binding of a neutralizing antibody to gp120.

gp120: An envelope protein from HIV. The envelope protein is initially synthesized as a longer precursor protein of 845-870 amino acids in size, designated gp160. Gp160 forms a homotrimer and undergoes glycosylation within the Golgi apparatus. It is then cleaved by a cellular protease into gp120 and gp41. Gp41 contains a transmembrane domain and remains in a trimeric configuration; it interacts with gp120 in a non-covalent manner. Gp120 contains most of the external, surface-exposed, domains of the envelope glycoprotein complex, and it is gp120 which binds both to the cellular CD4 receptor and to the cellular chemokine receptors (such as CCR5).

The mature gp120 wildtype polypeptides have about 500 amino acids in the primary sequence. Gp120 is heavily N-glycosylated giving rise to an apparent molecular weight of 120 kD. Exemplary sequence of wt gp160 polypeptides are shown on GENBANK®, for example accession numbers AAB05604 and AAD12142 incorporated herein by reference in their entirety as available on Feb. 25, 2009.

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core comprises 25 beta strands, 5 alpha helices, and 10 defined loop segments. The 10 defined loop segments include five conserved regions (C1-C5) and five regions of high variability (V1-V5).

Gp120 polypeptides also include "gp120-derived molecules" which encompasses analogs (non-protein organic molecules), derivatives (chemically functionalized protein molecules obtained starting with the disclosed protein sequences) or mimetics (three-dimensionally similar chemicals) of the native gp120 structure, as well as proteins sequence variants (such as mutants, for example deletions, such as loop deletions, insertions or point mutation in any combination), genetic alleles, fusions proteins of gp120, or combinations thereof.

The numbering used in gp120 polypeptides disclosed herein is relative to the HXB2 numbering scheme as set forth in *Numbering Positions in HIV Relative to HXB2CG* (Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex. which is incorporated by reference herein in its entirety).

As used herein, a variant gp120 polypeptide is a gp120 polypeptide in which one or more amino acids have been altered (e.g., deleted or substituted). In one example, a variant gp120 polypeptide is a gp120 polypeptide in which at least 8 consecutive residues, such as 9, 10, 11 or 12 consecutive residues, of the fourth conserved loop (C4) between residues 419 and 434 of gp120 of SEQ ID NO: 47 has been deleted. In a particular example, a variant gp120 polypeptide includes a gp120 polypeptide in which residues 424-432 are deleted. Additional variant gp120 polypeptides include deletions of INMWQKVGK (residues 424-432 of SEQ ID NO:47), INMWQKVGKA (residues 424-433 of SEQ ID NO: 47), INMWQKVGKAM (residues 424-434 of SEQ ID NO: 47), RIKQIINMWQKVGK (residues 419-432 of SEQ ID NO: 47), IKQIINMWQKVGK (residues 420-432 of SEQ ID NO: 47), KQIINMWQKVGK (residues 421-432 of SEQ ID NO: 47), QIINMWQKVGK (residues 422-432 of SEQ ID NO: 47), IINMWQKVGK (residues 423-432 of SEQ ID NO: 47). In other embodiments, variant gp120 polypeptides include combinations of the amino and carboxyl ends between residues 419 and 434.

Any of the disclosed variant gp120 polypeptide including deletions in C4 can also include a deletion in the V1V2 loop region (with an amino acid sequence set forth in SEQ ID NO: 47); see S R Pollard and DC Wiley, *EMBO J.* 11:585-91, 1992 which is hereby incorporated by reference in its entirety.

Hepatitis B Surface Antigen (HBsAg): HBsAg is composed of 3 polypeptides, preS1, preS2 and S that are produced from alternative translation start sites. The surface proteins have many functions, including attachment and penetration of the virus into hepatocytes at the beginning of the infection process. The surface antigen is a principal component of the hepatitis B envelope. HBsAg has four membrane spanning domains. As used herein, a variant HBsAg is a HBsAg that can include a MPR from gp41. In a particular example, a variant HBsAg includes a MPR and a membrane spanning domain from gp41.

Host cells: Cells in which a polynucleotide, for example, a polynucleotide vector or a viral vector, can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus (HIV): A virus, known to cause AIDS that includes HIV-1 and HIV-2. HIV-1 is composed of two copies of single-stranded RNA enclosed by a conical capsid including the viral protein p24, typical of lentiviruses. The capsid is surrounded by a plasma membrane of host-cell origin.

The envelope protein of HIV-1 is made up of a glycoprotein called gp160. The mature, virion associated envelope protein is a trimeric molecule composed of three gp120 and three gp41 subunits held together by weak noncovalent interactions. This structure is highly flexible and undergoes substantial conformational changes upon gp120 binding with CD4 and chemokine coreceptors, which leads to exposure of the fusion peptides of gp41 that insert into the target cell membrane and mediate viral entry. Following oligomerization in the endoplasmic reticulum, the gp160 precursor protein is cleaved by cellular proteases and is transported to the cell surface. During the course of HIV-1 infection, the gp120 and gp41 subunits are shed from virions and virus-infected cells due to the noncovalent interactions between gp120 and gp41 and between gp41 subunits.

Immune response: A response of a cell of the immune system, such as a B cell, T cell, or monocyte, to a stimulus. In some cases, the response is specific for a particular antigen (that is, an "antigen-specific response"). In some cases, an immune response is a T cell response, such as a CD4+ response or a CD8+ response. Alternatively, the response is a B cell response, and results in the production of specific antibodies. For purposes of the present invention, a "humoral immune response" refers to an immune response mediated by antibody molecules, while a "cellular immune response" is one mediated by T-lymphocytes and/or other white blood cells. A "protective immune response" is an immune response that inhibits a detrimental function or activity (such as a detrimental effect of a pathogenic organism such as a virus), reduces infection by a pathogenic organism (such as, a virus), or decreases symptoms that result from infection by the pathogenic organism. A protective immune response can be measured, for example, by the inhibition of viral replication or plaque formation in a plaque reduction assay or ELISA-neutralization assay (NELISA), or by measuring resistance to viral challenge in vivo.

An immunogenic composition can induce a B cell response. The ability of a particular antigen to stimulate a B cell response can be measured by determining if antibodies are present that bind the antigen. In one example, neutralizing antibodies are produced.

One aspect of cellular immunity involves an antigen-specific response by cytolytic T-cells ("CTL"s). CTLs have specificity for peptide antigens that are presented in association with proteins encoded by the major histocompatibility complex (MHC) and expressed on the surface of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, for example, Erickson et al. (1993) *J. Immunol.* 151:4189-4199; Doe et al. (1994) *Eur. J. Immunol.* 24:2369-2376. Recent methods of measuring cell-mediated immune response include measurement of intracellular cytokines or cytokine secretion by T-cell populations, or by measurement of epitope specific T-cells (for example, by the tetramer technique) (reviewed by McMichael and O'Callaghan (1998) *J. Exp. Med.* 187(9)1367-1371; Mcheyzer-Williams et al. (1996) *Immunol. Rev.* 150:5-21; Lalvani et al. (1997) *J. Exp. Med.* 186: 859-865).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or gamma-delta T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

Immunogen: A compound, composition, or substance which is capable, under appropriate conditions, of stimulating an immune response, such as the production of antibodies (a B-cell response) or a T-cell response in an animal, including compositions that are injected or absorbed into an animal.

Immunogenic peptide : A peptide which comprises an allele-specific motif or other sequence such that the peptide will bind an MHC molecule and induce a cytotoxic T lymphocyte ("CTL") response, or a B cell response (e.g., antibody production) against the antigen from which the immunogenic peptide is derived. In some examples, an immunogenic peptide is a gp120 peptide.

Immunogenic composition: A composition comprising at least one epitope of a virus, or other pathogenic organism, that induces a measurable CTL response, or induces a measurable B cell response (for example, production of antibodies that specifically bind the epitope). It further refers to isolated nucleic acids encoding an immunogenic epitope of virus or other pathogen that can be used to express the epitope (and thus be used to elicit an immune response against this polypeptide or a related polypeptide expressed by the pathogen). For in vitro use, the immunogenic composition may consist of the isolated nucleic acid, protein or peptide. For in vivo use, the immunogenic composition will typically include the nucleic acid, protein or peptide in pharmaceutically acceptable carriers or excipients, and/or other agents, for example, adjuvants. An immunogenic polypeptide (such as an antigenic polypeptide), or nucleic acid encoding the polypeptide, can be readily tested for its ability to induce a CTL or antibody response by art-recognized assays.

Immunotherapy: A method of evoking an immune response against a virus based on their production of target antigens. Immunotherapy based on cell-mediated immune responses involves generating a cell-mediated response to cells that produce particular antigenic determinants, while immunotherapy based on humoral immune responses involves generating specific antibodies to virus that produce particular antigenic determinants.

Inhibiting or treating a disease: Inhibiting the full development of a disease or condition, for example, in a subject who is at risk for a disease such as AIDS, AIDS related conditions, HIV-I infection, or combinations thereof. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a nucleic acid or protein or organelle) has been substantially separated or purified away from other biological components in the cell of the organism in which the component naturally occurs, for example, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Ligand: Any molecule which specifically binds a protein, such as a gp120 protein, and includes, inter alia, antibodies that specifically bind a gp120 protein. In alternative embodiments, the ligand is a protein or a small molecule (one with a molecular weight less than 6 kiloDaltons).

Membrane proximal region (MPR) or membrane proximal external region (MPER) of gp41: A region that is immediately N-terminal of the transmembrane region of gp41. The MPR is highly hydrophobic (50% of residues are hydrophobic) and is highly conserved across many HIV clades (Zwick, M. B., et al., *J Virol*, 75 (22): p. 10892-905, 2001). The conserved MPR of HIV-1 gp41 is a target of two broadly neutralizing human monoclonal antibodies, 2F5 and 4E10.

Mimetic: A molecule (such as an organic chemical compound) that mimics the activity of an agent, such as the activity of a gp120 protein, for example by inducing an immune response to gp120. Peptidomimetic and organomimetic embodiments are within the scope of this term, whereby the three-dimensional arrangement of the chemical constituents of such peptido- and organomimetics mimic the three-dimensional arrangement of the peptide backbone and component amino acid side chains in the peptide, resulting in such peptido- and organomimetics of the peptides having substantial specific activity. For computer modeling applications, a pharmacophore is an idealized, three-dimensional definition of the structural requirements for biological activity. Peptido- and organomimetics can be designed to fit each pharmacophore with computer modeling software (using computer assisted drug design or CADD). See Walters, "Computer-Assisted Modeling of Drugs", in Klegerman & Groves, eds., 1993, Pharmaceutical Biotechnology, Interpharm Press: Buffalo Grove, Ill., pp. 165-174 and Principles of Pharmacology (ed. Munson, 1995), chapter 102 for a description of techniques used in computer assisted drug design.

Operatively linked: A first nucleic acid sequence is operatively linked with a second nucleic acid sequence when the first nucleic acid sequence is placed in a functional relationship with the second nucleic acid sequence. For instance, a promoter is operatively linked to a coding sequence if the promoter affects the transcription or expression of the coding sequence. Generally, operatively linked DNA sequences are contiguous and, where necessary to join two protein-coding regions, in the same reading frame, for example, two polypeptide domains or components of a fusion protein.

Peptide Modifications: The present disclosure includes mutant gp120 peptides, as well as synthetic embodiments. In addition, analogues (non-peptide organic molecules), derivatives (chemically functionalized peptide molecules obtained starting with the disclosed peptide sequences) and variants (homologs) of gp120 can be utilized in the methods described herein. The peptides disclosed herein include a sequence of amino acids that can be either L- and/or D- amino acids, naturally occurring and otherwise.

Peptides can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently II or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Peptidomimetic and organomimetic embodiments are also within the scope of the present disclosure, whereby the three-dimensional arrangement of the chemical constituents of such peptido- and organomimetics mimic the three-dimensional arrangement of the peptide backbone and component amino acid side chains, resulting in such peptido- and organomimetics of the proteins of this disclosure. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included within the scope of the disclosure are mimetics prepared using such techniques. In one example, a mimetic mimics the antigenic activity generated by gp120 a mutant, a variant, fragment, or fusion thereof.

Pharmaceutical agent: A chemical compound or composition capable of inducing a desired therapeutic or prophylactic effect when properly administered to a subject or a cell. "Incubating" includes a sufficient amount of time for a drug to interact with a cell. "Contacting" includes incubating a drug in solid or in liquid form with a cell. An "anti-viral agent" or "anti-viral drug" is an agent that specifically inhibits a virus from replicating or infecting cells. Similarly, an "anti-retroviral agent" is an agent that specifically inhibits a retrovirus from replicating or infecting cells.

A "therapeutically effective amount" is a quantity of a chemical composition or an anti-viral agent sufficient to achieve a desired effect in a subject being treated. For instance, this can be the amount necessary to inhibit viral replication or to measurably alter outward symptoms of the viral infection, such as increase of T cell counts in the case of an HIV-I infection. In general, this amount will be sufficient to measurably inhibit virus (for example, HIV) replication or infectivity. When administered to a subject, a dosage will generally be used that will achieve target tissue concentrations (for example, in lymphocytes) that has been shown to achieve in vitro inhibition of viral replication.

Pharmaceutically acceptable carriers and/or pharmaceutically acceptable excipients: The pharmaceutically acceptable carriers or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides and polynucleotides disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Preventing or treating an infection: Inhibiting infection by a pathogen such as a virus, such as a lentivirus, or other virus, refers to inhibiting the full development of a disease either by avoiding initial infection or inhibiting development of the disease process once it is initiated. For example, inhibiting a viral infection refers to lessening symptoms resulting from infection by the virus, such as preventing the development of symptoms in a person who is known to have been exposed to the virus, or to lessening virus number or infectivity of a virus in a subject exposed to the virus. "Treatment" refers to a therapeutic or prophylactic intervention that ameliorates or prevents a sign or symptom of a disease or pathological condition related to infection of a subject with a virus or other pathogen. Treatment can also induce remission or cure of a condition, such as elimination of detectable HIV infected cells. In particular examples, treatment includes preventing a disease, for example by inhibiting the full development of a disease, such as HIV, by inhibiting HIV replication or infection or the development of AIDS. Prevention of a disease does not require a total absence of disease. For example, a decrease of at least 50% can be sufficient.

Promoter: A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (for example, metallothionein promoter) or from mammalian viruses (for example, the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Purified: The term "purified" does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least 50% (such as, but not limited to, 70%, 80%, 90%, 95%, 98% or 99%) of the total peptide or protein content of the preparation.

Recombinant: A recombinant nucleic acid is one that has a sequence that is not naturally occurring or has a sequence that is made by an artificial combination of two otherwise separated segments of sequence, for example, a polynucleotide encoding a fusion protein. This artificial combination is often accomplished by chemical synthesis or, more commonly, by the artificial manipulation of isolated segments of nucleic acids, e.g., by genetic engineering techniques.

T cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutic agent: Used in a generic sense, it includes treating agents, prophylactic agents, and replacement agents.

Therapeutically Effective Amount: An amount of a composition that alone, or together with an additional therapeutic agent(s) (for example nucleoside/nucleotide reverse transcriptase inhibitors, a non-nucleoside reverse transcriptase inhibitors, protease inhibitors, fusion/entry inhibitors or integrase inhibitors) induces the desired response (e.g., inhibition of HIV infection or replication). In one example, a desired response is to inhibit HIV replication in a cell to which the therapy is administered. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of HIV), as compared to HIV replication in the absence of the composition.

In another example, a desired response is to inhibit HIV infection. The HIV infected cells do not need to be completely eliminated for the composition to be effective. For example, a composition can decrease the number of HIV infected cells by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to the number of HIV infected cells in the absence of the composition.

A therapeutically effective amount of a composition including variant gp120 polypeptides, can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 μg -10 mg per 70 kg body weight if administered intravenously.

Transformed or Transfected: A transformed cell is a cell into which a nucleic acid molecule has been introduced by molecular biology techniques. As used herein, the term introduction or transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV). HIV-1 is a retrovirus that causes immunosuppression in humans (HIV disease), and leads to a disease complex known as AIDS. "HIV infection" refers to the process in which HIV enters macrophages and CD4+ T cells by the adsorption of glycoproteins on its surface to receptors on the target cell followed by fusion of the viral envelope with the cell membrane and the release of the HIV capsid into the cell. "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

Virus-like particle (VLP): A nonreplicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) *Biophys. J.* 60:1445-1456; and Hagensee et al. (1994) *J. Virol.* 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

II. Overview of Several Embodiments

Disclosed herein are targeted deletions of the loops surrounding the CD4BS designed to expose the CD4BS or to overcome conformational barriers to antibody binding. Deletion of nine amino acids in the β20-β21 loop gave enhanced antibody binding to the CD4BS, both for a monoclonal that depends strongly on the protein conformation and for one that is relatively insensitive to it. As disclosed herein molecular modeling suggests that deletion of this loop improves antibody binding both by reducing steric hindrance and by altering the protein conformation to expose the CD4BS. The same features that prevent antibody binding could also interfere with induction of antibodies to conserved neutralizing determinants. However, the disclosed variant gp120 polypeptides have surprisingly improved antibody binding to the CD4BS and provide novel immunogens capable of eliciting antibodies to this broadly shared neutralizing determinant.

A. Isolated Immunogens with Variant gp120

Isolated immunogens including variant gp120 polypeptides are disclosed. In an example, a variant gp120 polypeptide includes a gp120 polypeptide in which at least 8 consecutive residues of the fourth conserved loop (C4) between residues 419 and 434 of gp120 according HXB2 numbering of SEQ ID NO: 47 are deleted. This deletion within the 1320-21 loop of the gp120 polypeptide exposes the CD4 binding site thereby providing improved antibody binding and antibody induction. In one example, a variant gp120 polypeptide is a gp120 polypeptide in which at least 8 consecutive residues, such as between 8-12, 8-11, 8-10, or 8-9 (for example, 9, 10, 11 or 12) consecutive residues of C4 between residues 419 and 434 of gp120 of SEQ ID NO: 47 have been deleted.

In a particular example, a variant gp120 polypeptide includes a gp120 polypeptide in which residues 424-432 are deleted. Additional variant gp120 polypeptides include deletions of INMWQKVGK (residues 424-432 of SEQ ID NO: 47), INMWQKVGKA (residues 424-433 of SEQ ID NO: 47), INMWQKVGKAM (residues 424-434 of SEQ ID NO: 47), RIKQIINMWQKVGK (residues 419-432 of SEQ ID NO: 47), IKQIINMWQKVGK (residues 420-432 of SEQ ID NO: 47), KQIINMWQKVGK (residues 421-432 of SEQ ID NO: 47), QIINMWQKVGK (residues 422-432 of SEQ ID NO: 47), or IINMWQKVGK (residues 423-432 of SEQ ID NO: 47). In other embodiments, variant gp120 polypeptides include combinations of the amino and carboxyl ends between residues 419 and 434.

In some embodiments, a variant gp120 polypeptide does not include a variant in which residues 419-428 of SEQ ID NO: 47 are deleted. In other embodiments, a variant gp120 polypeptide does not include a variant in which residues 437-452 of SEQ ID NO: 47 are deleted.

Any of the disclosed variant gp120 polypeptide including deletions in C4 can also include a deletion in the V1V2 loop region (spanning from amino acids 125 to 205 of wild-type gp120, such as demonstrated in SEQ ID NO: 47); see S R Pollard and D C Wiley, *EMBO J.* 11:585-91, 1992 which is hereby incorporated by reference in its entirety.

The immunogenic variant gp120 polypeptides disclosed herein can be chemically synthesized by standard methods, or can be produced recombinantly. An exemplary process for polypeptide production is described in Lu et al., *Federation of European Biochemical Societies Letters.* 429:31-35, 1998. They can also be isolated by methods including preparative chromatography and immunological separations.

Exemplary sequences for the amino acid sequence for full-length gp120 can be found on Genbank, EMBL and SwissProt websites. Exemplary non-limiting sequence information can be found for example, as SwissProt Accession No. PO4578, (includes gp41 and gp120, initial entry Aug. 13, 1987, last modified on Jul. 15, 1999) and Genbank Accession No. AAF69493 (Oct. 2, 2000, gp120), all of which are incorporated herein by reference as of Feb. 26, 2009.

In other embodiments, fusion proteins are provided including a first and second polypeptide moiety in which one of the protein moieties includes a variant gp120 polypeptide such as a variant gp120 polypeptide with an amino acid sequence in which INMWQKVGK (residues 424-432 of SEQ ID NO:47), INMWQKVGKA (residues 424-433 of SEQ ID NO: 47), INMWQKVGKAM (residues 424-434 of SEQ ID NO: 47), RIKQIINMWQKVGK (residues 419-432 of SEQ ID NO: 47), IKQIINMWQKVGK (residues 420-432 of SEQ ID NO: 47), KQIINMWQKVGK (residues 421-432 of SEQ ID NO: 47), QIINMWQKVGK (residues 422-432 of SEQ ID NO: 47), or IINMWQKVGK (residues 423-432 of SEQ ID NO: 47) has been deleted. The other moiety is a heterologous protein such as a carrier protein and/or an immunogenic protein. Such fusions also are useful to evoke an immune response against gp120. In certain embodiments the gp120 polypeptides disclosed herein are covalent or non-covalent addition of toll like receptor (TLR) ligands or dendritic cell or B cell targeting moieties to produce self-adjuvanting proteins (e.g., IL-21).

In certain embodiments, a variant gp120 includes a V1V2 deletion without a beta 20-21 loop deletion with an amino acid sequence as set forth as:

(SEQ ID NO: 47)
```
V P V W R E A T T T L F C A S D A K A Y D T E V H
N V W A T H A C V P T D P N P Q E V V L G N V T E
N F N M W K N N M V D Q M H E D I I S L W D E S L
K P C V K L T P L S V Q A C P K V S F Q P I P I H
Y C V P A G F A M L K C N N K T F N G S G P C T N
V S T V Q C T H G I R P V V S T Q L L L N G S L A
E E D I V I R S E N F T D N A K T I I V Q L N E S
V V I N C T R P N N N T R R L S I G P G R A F Y
A R R N I I G D I R Q A H C N I S R A K W N N T L
Q Q I V I K L R E K F R N K T I A F N Q S S G G D
P E I V M H S F N C G G E F F Y C N T A Q L F N S
T W N V T G G T N G T E G N D I I T L Q C R I K Q
I I N M W Q K V G K A M Y A P P I T G Q I R C S S
N I T G L L L T R D G G N S T E T E T E I F R P G
G G D M R D N W R S E L Y K Y K V V R I E P I G V
A P T R A K R.
```

Sequences for deletion to generate gp120 variant with an amino acid sequence set forth in SEQ ID NO: 50 are shown in bold.

In some embodiments, a variant gp120 includes a V1V2 deletion with a beta 20-21 loop deletion with an amino acid sequence as set forth as:

(SEQ ID NO: 50)
```
V P V W R E A T T T L F C A S D A K A Y D T E V H N V W A T H A C V
P T D P N P Q E V V L G N V T E N F N M W K N N M V D Q M H E D I I
S L W D E S L K P C V K L T P L S V Q A C P K V S F Q P I P I H Y C V P
A G F A M L K C N N K T F N G S G P C T N V S T V Q C T H G I R P V V
S T Q L L L N G S L A E E D I V I R S E N F T D N A K T I I V Q L N E S
V V I N C T R P N N N T R R L S I G P G R A F Y A R R N I I G D I R Q
A H C N I S R A K W N N T L Q Q I V I K L R E K F R N K T I A F N Q S S
G G D P E I V M H S F N C G G E F F Y C N T A Q L F N S T W N V T G G
```

-continued

```
T N G T E G N D I I T L Q C R I K Q L A M Y A P P I T G Q I R C S S N I

T G L L L T R D G G N S T E T E T E I F R P G G G D M R D N W R S E L

Y K Y K V V R I E P I G V A P T R A K R.
```

In other embodiments, a variant gp120 from a HIV isolate JRFL includes an amino acid sequence as set forth in SEQ ID NO: 51 and nucleic acid sequence set forth in SEQ ID NO: 52:

```
                                                         (SEQ ID NO: 51)
I I H T V P P S G A D P G P K R A E F K G L R R Q Q K Q G I I L L

T M K T I I A L S Y I L C L V L A Q K L P G N D N N S E F I T S G F L G

P L L V L Q A G F F L L T R I L T I P Q S L D S W W T S L N F L G G S P

V C L G Q N S Q S P T S N H S P T S C P P I C P G Y R M C L R R F I I F

L F I L L L C L I F L L V L L D Y Q G M L P V C P L I P G S T T T S T G P

C K T C T T P A Q G N S K F P S C C C T K P T D G N C T C I P I P S S W

A F A K Y L W E W A S V R F S W L S L L V P F V Q W F V G L S P T V

W L S A I W M M W Y W G P S L Y S I V S P F I P L L P I F F C L W V Y I

G V P V W K E A T T T L F C A S D A K A Y D T E V H N V W A T H A C

V P T D P N P Q E V V L E N V T E H F N M W K N N M V E Q M Q E D I I

S L W D Q S L K P C V K L T P L Q A C P K I S F E P I P I H Y C A P A G

F A I L K C N D K T F N G K G P C K N V S T V Q C T H G I R P V V S T

Q L L L N G S L A E E E V V I R S D N F T N N A K T I I V Q L K E S V E

I N C T R P N N N T R K S I H I G P G R A F Y T T G E I I G D I R Q A H

C N I S R A K W N D T L K Q I V I K L R E Q F E N K T I V F N H S S G G

D P E I V M H S F N C G G E F F Y C N S T Q L F N S T W N N N T E G S

N N T E G N T I T L P C R I K Q L A M Y A P P I R G Q I R C S S N I T G

L L L T R D G G I N E N G T E I F R P G G G D M R D N W R S E L Y K Y

K V V K I E P L G V A P T K A K R.
                                                         (SEQ ID NO: 52)
GGATTATTCATACCGTCCCACCATCGGGCGCGGATCCCGGTCCGAAGCGCGCGG

AATTCAAAGGCCTACGTCGACAGCAAAAGCAGGGGATAATTCTATTAACCATGAAGACT

ATCATTGCTTTGAGCTACATTTTATGTCTGGTTCTCGCTCAAAAACTTCCCGGAAATGAC

AACAACAGCGAATTCATCACCTCCGGCTTCCTGGGCCCCCTGCTGGTGCTGCAGGCCGG

CTTCTTCCTGCTGACCCGCATCCTGACCATCCCCCAGTCCCTGGACTCCTGGTGGACCTC

CCTGAACTTCCTGGGCGGCTCCCCCGTGTGCCTGGGCCAGAACTCCCAGTCCCCCACCTC

CAACCACTCCCCCACCTCCTGCCCCCCCATCTGCCCCGGCTACCGCTGGATGTGCCTGCG

CCGCTTCATCATCTTCCTGTTCATCCTGCTGCTGTGCCTGATCTTCCTGCTGGTGCTGCTG

GACTACCAGGGCATGCTGCCCGTGTGCCCCCTGATCCCCGGCTCCACCACCACCTCCACC

GGCCCCTGCAAGACCTGCACCACCCCCGCCCAGGGCAACTCCAAGTTCCCCTCCTGCTG

CTGCACCAAGCCCACCGACGGCAACTGCACCTGCATCCCCATCCCCTCCTCCTGGGCCTT

CGCCAAGTACCTGTGGGAGTGGGCCTCCGTGCGCTTCTCCTGGCTGTCCCTGCTGGTGCC

CTTCGTGCAGTGGTTCGTGGGCCTGTCCCCCACCGTGTGGCTGTCCGCCATCTGGATGAT

GTGGTACTGGGGCCCCTCCCTGTACTCCATCGTGTCCCCCTTCATCCCCCTGCTGCCCAT
```

-continued
CTTCTTCTGCCTGTGGGTGTACATCGGGGTACCTGTGTGGAAAGAAGCAACCACCACTCT

ATTTTGTGCATCAGATGCTAAAGCATATGATACAGAGGTACATAATGTTTGGGCCACAC

ATGCCTGTGTACCCACAGACCCCAACCCACAAGAAGTAGTATTGGAAAATGTAACAGAA

CATTTTAACATGTGGAAAAATAACATGGTAGAACAGATGCAGGAGGATATAATCAGTTT

ATGGGATCAAAGCCTAAAGCCATGTGTAAAATTAACCCCACTCCAGGCCTGTCCAAGA

TATCCTTTGAGCCAATTCCCATACATTATTGTGCCCCGGCTGGTTTTGCGATTCTAAAGT

GTAATGATAAGACGTTCAATGGAAAAGGACCATGTAAAAATGTCAGCACAGTACAATG

TACACATGGAATTAGGCCAGTAGTATCAACTCAACTGCTGCTAAATGGCAGTCTAGCAG

AAGAAGAGGTAGTAATTAGATCTGACAATTTCACGAACAATGCTAAAACCATAATAGTA

CAGCTGAAAGAATCTGTAGAAATTAATTGTACAAGACCCAACAACAATACAAGAAAAA

GTATACATATAGGACCAGGGAGAGCATTTTATACTACAGGAGAAATAATAGGAGATAT

AAGACAAGCACATTGTAACATTAGTAGAGCAAAATGGAATGACACTTTAAAACAGATA

GTTATAAAATTAAGAGAACAATTTGAGAATAAAACAATAGTCTTTAATCACTCCTCAGG

AGGGGACCCAGAAATTGTAATGCACAGTTTTAATTGTGGAGGAGAATTTTTCTACTGTA

ATTCAACACAACTGTTTAATAGTACTTGGAATAATAATACTGAAGGGTCAAATAACACT

GAAGGAAATACTATCACACTCCCATGCAGAATAAAACAGCTAGCAATGTATGCCCCTCC

CATCAGAGGACAAATTAGATGTTCATCAAATATTACAGGGCTGCTATTAACAAGAGATG

GTGGTATTAATGAGAATGGGACCGAGATCTTCAGACCTGGAGGAGGAGATATGAGGGA

CAATTGGAGAAGTGAATTATATAAATATAAAGTAGTAAAAATTGAACCATTAGGAGTAG

CACCCACCAAGGCAAAGAGATGACTAGTCGCGGCCGCTTTCGAATCTAGA.

In other embodiments, a variant gp120 from a HIV isolate AD8 includes an amino acid sequence as set forth in SEQ ID NO: 53 or nucleic acid sequence set forth in SEQ ID NO: 54:

(SEQ ID NO: 53)
I I H T V P P S G A D P G P K R A E F K G L R R Q
Q K Q G I I L L T M K T I I A L S Y I L C L V L A
Q K L P G N D N N S E F I T S G F L G P L L V L Q
A G F F L L T R I L T I P Q S L D S W W T S L N F
L G G S P V C L G Q N S Q S P T S N H S P T S C P
P I C P G Y R W M C L R R F I I F L F I L L L C L
I F L L V L L D Y Q G M L P V C P L I P G S T T T
S T G P C K T C T T P A Q G N S K F P S C C C T K
P T D G N C T C I P I P S S W A F A K Y L W E W A
S V R F S W L S L L V P F V Q W F V G L S P T V W
L S A I W M M W Y W G P S L Y S I V S P F I P L L
P I F F C L W V Y I G V P V W K E A T T T L F C A
S D A K A Y D T E V H N V W A T H A C V P T D P N
P Q E V V L E N V T E N F N M W K N N M V E Q M H
E D I I S L W D Q S L K P C V K L T P L Q A C P K
V S F E P I P I H Y C T P A G F A I L K C K D K A
F N G T G P C K N V S T V Q C T H G I R P V V S T
Q L L L N G S L A E E E V V I R S S N F T D N A K
N I I V Q L K E S V E I N C T R P N N N T R K S I
H I G P G R A F Y T T G E I I G D I R Q A H C N I
S R T K W N N T L N Q I A T K L K E Q F G N N K T
I V F N Q S S G G D P E I V M H S F N C G G E F F
Y C N S T Q L F N S T W N F N G T W N L T Q S N G
T E G N D T I T L P C R I K Q L A M Y A P P I R G
Q I R C S S N I T G L I L T R D G G N N H N N D T
E T F R P G G G D M R D N W R S E L Y K Y K V V K
I E P L G V A P T K A K R (SEQ ID NO: 54)
GGATTATTCATACCGTCCCACCATCGGGCGCGGATCCCGGTCCGAAGCGC
GCGGAATTCAAAGGCCTACGTCGACAGCAAAAGCAGGGGATAATTCTATT
AACCATGAAGACTATCATTGCTTTGAGCTACATTTTATGTCTGGTTCTCG
CTCAAAAACTTCCCGGAAATGACAACAACAGCGAATTCATCACCTCCGGC

-continued
TTCCTGGGCCCCCTGCTGGTGCTGCAGGCCGGCTTCTTCCTGCTGACCCG
CATCCTGACCATCCCCCAGTCCCTGGACTCCTGGTGGACCTCCCTGAACT
TCCTGGGCGGCTCCCCCGTGTGCCTGGGCCAGAACTCCCAGTCCCCCACC
TCCAACCACTCCCCCACCTCCTGCCCCCCATCTGCCCCGGCTACCGCTG
GATGTGCCTGCGCCGCTTCATCATCTTCCTGTTCATCCTGCTGCTGTGCC
TGATCTTCCTGCTGGTGCTGCTGGACTACCAGGGCATGCTGCCCGTGTGC
CCCCTGATCCCCGGCTCCACCACCACCTCCACCGGCCCCTGCAAGACCTG
CACCACCCCCGCCCAGGGCAACTCCAAGTTCCCCTCCTGCTGCTGCACCA
AGCCCACCGACGGCAACTGCACCTGCATCCCCATCCCCTCCTCCTGGGCC
TTCGCCAAGTACCTGTGGGAGTGGGCCTCCGTGCGCTTCTCCTGGCTGTC
CCTGCTGGTGCCCTTCGTGCAGTGGTTCGTGGGCCTGTCCCCCACCGTGT
GGCTGTCCGCCATCTGGATGATGTGGTACTGGGGCCCCTCCCTGTACTCC
ATCGTGTCCCCCTTCATCCCCCTGCTGCCCATCTTCTTCTGCCTGTGGGT
GTACATCGGGGTACCTGTGTGGAAAGAAGCAACCACCACTCTATTTTGTG
CATCAGATGCTAAAGCATATGATACAGAGGTACATAATGTTTGGGCCACA
CATGCCTGTGTACCCACAGACCCCAACCCACAAGAAGTAGTATTGGAAAA
TGTGACAGAAAATTTTAACATGTGGAAAAATAACATGGTAGAACAGATGC
ATGAGGATATAATCAGTTTATGGGATCAAAGCCTAAAGCCATGTGTAAAA
TTAACCCCACTCCAGGCCTGTCCAAAGGTATCCTTTGAGCCAATTCCCAT
ACATTATTGTACCCCGGCTGGTTTTGCGATTCTAAAGTGTAAAGACAAGA
AGTTCAATGGAACAGGGCCATGTAAAAATGTCAGCACAGTACAATGTACA
CATGGAATTAGGCCAGTAGTGTCAACTCAACTGCTGTTAAATGGCAGTCT
AGCAGAAGAAGAGGTAGTAATTAGATCTGTAATTTCACAGACAATGCAA
AAAACATAATAGTACAGTTGAAAGAATCTGTAGAAATTAATTGTACAAGA
CCCAACAACAATACAAGGAAAAGTATACATATAGGACCAGGAAGAGCATT
TTATACAACAGGAGAAATAATAGGAGATAAGACAAGCACATTGTAACA
TTAGTAGACAAAATGGAATAACACTTTAAATCAAATAGCTACAAAATTA
AAAGAACAATTTGGGAATAATAAAACAATAGTCTTTAATCAATCCTCAGG
AGGGGACCCAGAAATTGTAATGCACAGTTTTAATTGTGGAGGGGAATTTT
TCTACTGTAATTCAACACAACTGTTTAATAGTACTTGGAATTTTAATGGT
ACTTGGAATTTAACACAATCGAATGGTACTGAAGGAAATGACACTATCAC
ACTCCCATGTAGAATAAAACAGCTAGCAATGTATGCCCCTCCCATCAGAG
GACAAATTAGATGCTCATCAAATATTACAGGGCTAATATTAACAAGAGAT
GGTGGAAATAACCACAATAATGATACCGAGACCTTTAGACCTGGAGGAGG
AGATATGAGGGACAATTGGAGAAGTGAATTATATAAATATAAAGTAGTAA
AAATTGAACCATTAGGAGTAGCACCCACCAAGGCAAAAGATGACTAGT
C.

In other embodiments, a variant gp120 from a HIV isolate BaL includes an amino acid sequence as set forth in SEQ ID NO: 55 or a nucleic acid sequence as set forth in SEQ ID NO: 56:

(SEQ ID NO: 55)
```
I I H T V P P S G A D P G P K R A E F K G L R R Q
Q K Q G I I L L T M K T I I A L S Y I L C L V L A
Q K L P G N D N N S E F I T S G F L G P L L V L Q
A G F F L L T R I L T I P Q S L D S W W T S L N F
L G G S P V C L G Q N S Q S P T S N H S P T S C P
P I C P G Y R W M C L R R F I I F L F I L L L C L
I F L L V L L D Y Q G M L P V C P L I P G S T T T
S T G P C K T C T T P A Q G N S K F P S C C C T K
P T D G N C T C I P I P S S W A F A K Y L W E W A
S V R F S W L S L L V P F V Q W F V G L S P T V W
L S A I W M M W Y W G P S L Y S I V S P F I P L L
P I F F C L W V Y I G V P V W K E A T T T L F C A
S D A K A Y D T E V H N V W A T H A C V P T D P N
P Q E V E L E N V T E N F N M W K N N M V E Q M H
E D I I S L W D Q S L K P C V K L T P L Q A C P K
I S F E P I P I H Y C A P A G F A I L K C K D K K
F N G K G P C S N V S T V Q C T H G I R P V V S T
Q L L L N G S L A E E E V V I R S E N F A D N A K
T I I V Q L N E S V E I N C T R P N N N T R K S I
H I G P G R A L Y T T G E I I G D I R Q A H C N L
S R A K W N D T L N K I V I K L R E Q F G N K T I
V F K H S S G G D P E I V T H S F N C G G E F F Y
C N S T Q L F N S T W N V T E E S N N T V E N N T
I T L P C R I K Q L A M Y A P P I R G Q I R C S S
N I T G L L L T R D G G P E D N K T E V F R P G G
G D M R D N W R S E L Y K Y K V V K I E P L G V A
P T K A K R.
```

(SEQ ID NO: 56)
```
GGATTATTCATACCGTCCCACCATCGGGCGCGGATCCCGGTCCGAAGCGC
GCGGAATTCAAAGGCCTACGTCGACAGCAAAAGCAGGGGATAATTCTATT
AACCATGAAGACTATCATTGCTTTGAGCTACATTTTATGTCTGGTTCTCG
CTCAAAAACTTCCCGGAAATGACAACAACAGCGAATTCATCACCTCCGGC
TTCCTGGGCCCCCTGCTGGTGCTGCAGGCCGGCTTCTTCCTGCTGACCCG
CATCCTGACCATCCCCCAGTCCCTGGACTCCTGGTGGACCTCCCTGAACT
TCCTGGGCGGCTCCCCCGTGTGCCTGGGCCAGAACTCCCAGTCCCCCACC
TCCAACCACTCCCCCACCTCCTGCCCCCCCATCTGCCCCGGCTACCGCTG
GATGTGCCTGCGCCGCTTCATCATCTTCCTGTTCATCCTGCTGCTGTGCC
TGATCTTCCTGCTGGTGCTGCTGGACTACCAGGGCATGCTGCCCGTGTGC
CCCCTGATCCCCGGCTCCACCACCACCTCCACCGGCCCCTGCAAGACCTG
CACCACCCCCGCCCAGGGCAACTCCAAGTTCCCCTCCTGCTGCTGCACCA
AGCCCACCGACGGCAACTGCACCTGCATCCCCATCCCCTCCTCCTGGGCC
TTCGCCAAGTACCTGTGGGAGTGGGCCTCCGTGCGCTTCTCCTGGCTGTC
CCTGCTGGTGCCCTTCGTGCAGTGGTTCGTGGGCCTGTCCCCCACCGTGT
GGCTGTCCGCCATCTGGATGATGTGGTACTGGGGCCCCTCCCTGTACTCC
ATCGTGTCCCCCTTCATCCCCCTGCTGCCCATCTTCTTCTGCCTGTGGGT
GTACATCGGGGTACCTGTGTGGAAAGAAGCAACCACCACTCTATTTTGTG
CATCAGATGCTAAAGCATATGATACAGAGGTACATAATGTTTGGGCCACA
CATGCCTGTGTACCCACAGACCCCAACCCACAAGAAGTAGTATTGGTAAA
TGTGACAGAAAATTTTAACATGTGGAAAAATAACATGGTAGAACAGATGC
ATGAGGATATAATCAGTTTATGGGATCAAAGCCTAAAGCCATGTGTAAAA
TTAACTCCACTCCAGGCCTGTCCAAAGATATCCTTTGAGCCAATTCCCAT
ACATTATTGTGCCCGGCTGGTTTTGCGATTCTAAAGTGTAAAGATAAGA
AGTTCAATGGAAAAGGACCATGTTCAAATGTCAGCACAGTACAATGTACA
CATGGGATTAGGCCAGTAGTATCAACTCAACTGCTGTTAAATGGCAGTCT
AGCAGAAGAAGAGGTAGTAATTAGATCCGAAAATTTCGCGGACAATGCTA
AAACCATAATAGTACAGCTGAATGAATCTGTAGAAATTAATTGTACAAGA
CCCAACAACAATACAAGAAAAAGTATACATATAGGACCAGGCAGAGCATT
ATATACAACAGGAGAAATAATAGGAGATAGACAAGCACATTGTAACC
TTAGTAGAGCAAAATGGAATGACACTTTAAATAAGATAGTTATAAAATTA
AGAGAACAATTTGGGAATAAAACAATAGTCTTTAAGCATTCCTCAGGAGG
GGACCCAGAAATTGTGACGCACAGTTTTAATTGTGGAGGGGAATTTTTCT
ACTGTAATTCAACACAACTGTTTAATAGTACTTGGAATGTTACTGAAGAG
TCAAATAACACTGTAGAAAATAACACAATCACTCCCATGCAGAATAA
ACAGCTAGCAATGTATGCCCCTCCCATCAGAGGACAAATTAGATGTTCAT
CAAATATTACAGGGCTGCTATTAACAAGAGATGGTGGTCCAGAGGACAAC
AAGACCGAGGTCTTCAGACCTGGAGGAGGAGATATGAGGGACAATTGGAG
AAGTGAATTATATAAATATAAAGTAGTAAAAATTGAACCATTAGGAGTAG
CACCCACCAAGGCAAAGAGATGACTAGTCGCGGCCGCTTTCGAATCTAG
A.
```

In other embodiments, a variant gp120 from a HIV isolate IIIB includes an amino acid sequence as set forth in SEQ ID NO: 57 or a nucleic acid sequence as set forth in SEQ ID NO: 58):

(SEQ ID NO: 57)
```
I I H T V P P S G A D P G P K R A E F K G L R R Q
Q K Q G I I L L T M K T I I A L S Y I L C L V L A
Q K L P G N D N N S E F I T S G F L G P L L V L Q
A G F F L L T R I L T I P Q S L D S W W T S L N F
L G G S P V C L G Q N S Q S P T S N H S P T S C P
P I C P G Y R W M C L R R F I I F L F I L L L D C
L I F L L V L L D Y Q G M L P V C P L I P G S T T
T S T G P C K T C T T P A Q G N S K F P S C C C T
K P T D G N C T C I P I P S S W A F A K Y L W E W
A S V R F S W L S L L V P F V Q W F V G L S P T V
W L S A I W M M W Y W G P S L Y S I V S P F I P L
L P I F F C L W V Y I G V P V W K E A T T T L F C
A S D A K A Y D T E V H N V W A T H A C V P T D P
N P Q E V V L V N V T E N F N M W K N D M V E Q M
H E D I I S L W D Q S L K P C V K L T P L S V Q A
C P K V S F E P I P I H Y C A P A G F A I L K C N
N K T F N G T G P C T N V S T V Q C T H G I R P V
V S T Q L L L N G S L A E E E V V I R S V N F T D
N A K T I I V Q L N T S V E I N C T R P S V N F T
D N A K T I I V Q L N T S V E I N C T R P M R Q A
H C N I S R A K W N N T L K Q I A S K L R E Q F G
N N K T I I F K Q S S G G D P E I V T H S F N C G
G E F F Y C N S T Q L F N S T W F N S T W S T E G
S N N T E G S D T I T L P C R I K Q S I A M Y A P
P I S G Q I R C S S N I T G L L L T R D G G N S N
N E S E I F R P G G G D M R D N W R S E L Y K Y K
V V K I E P L G V A P T K A K R.
```

(SEQ ID NO: 58)
```
GGATTATTCATACCGTCCCACCATCGGGCGCGGATCCCGGTCCGAAGCGC
GCGGAATTCAAAGGCCTACGTCGACAGCAAAAGCAGGGGATAATTCTATT
AACCATGAAGACTATCATTGCTTTGAGCTACATTTTATGTCTGGTTCTCG
CTCAAAAACTTCCCGGAAATGACAACAACAGCGAATTCATCACCTCCGGC
TTCCTGGGCCCCCTGCTGGTGCTGCAGGCCGGCTTCTTCCTGCTGACCCG
CATCCTGACCATCCCCCAGTCCCTGGACTCCTGGTGGACCTCCCTGAACT
TCCTGGGCGGCTCCCCCGTGTGCCTGGGCCAGAACTCCCAGTCCCCCACC
TCCAACCACTCCCCCACCTCCTGCCCCCCCATCTGCCCCGGCTACCGCTG
GATGTGCCTGCGCCGCTTCATCATCTTCCTGTTCATCCTGCTGCTGTGCC
TGATCTTCCTGCTGGTGCTGCTGGACTACCAGGGCATGCTGCCCGTGTGC
CCCCTGATCCCCGGCTCCACCACCACCTCCACCGGCCCCTGCAAGACCTG
CACCACCCCCGCCCAGGGCAACTCCAAGTTCCCCTCCTGCTGCTGCACCA
AGCCCACCGACGGCAACTGCACCTGCATCCCCATCCCCTCCTCCTGGGCC
TTCGCCAAGTACCTGTGGGAGTGGGCCTCCGTGCGCTTCTCCTGGCTGTC
CCTGCTGGTGCCCTTCGTGCAGTGGTTCGTGGGCCTGTCCCCCACCGTGT
GGCTGTCCGCCATCTGGATGATGTGGTACTGGGGCCCCTCCCTGTACTCC
ATCGTGTCCCCCTTCATCCCCCTGCTGCCCATCTTCTTCTGCCTGTGGGT
GTACATCGGGGTACCTGTGTGGAAGGAAGCAACCACCACTCTATTTTGTG
CATCAGATGCTAAAGCATATGATACAGAGGTACATAATGTTTGGGCCACA
CATGCCTGTGTACCCACAGACCCCAACCCACAAGAAGTAGTATTGGTAAA
TGTGACAGAAAATTTTAACATGTGGAAAAATGACATGGTAGAACAGATGC
ATGAGGATATAATCAGTTTATGGGATCAAAGCCTAAAGCCATGTGTAAAA
TTAACCCCACTCTCGGTCCAGGCCTGTCAAAGGTATCCTTTGAGCCAAT
TCCCATACATTATTGTGCCCCGGCTGGTTTTGCGATTCTAAAATGTAAAA
ATAAGACGTTCAATGGAACAGGACCATGTACAAATGTCAGCACAGTACAA
TGTACACATGGAATTAGGCCAGTAGTATCAACTCAACTGCTGTTAAATGG
CAGTCTAGCAGAAGAAGAGGTAGTAATTAGATCTGTCAATTTCACGGACA
ATGCTAAAACCATAATAGTACAGCTGAACACATCTGTAGAAATTAATTGT
ACAAGACCCTCTGTCAATTTCACGGACAATGCTAAAACCATAATAGTACA
GCTGAACACATCTGTAGAAATTAATTGTACAAGACCCATGAGACAAGCAC
ATTGTAACATTAGTAGAGCAAATGGAATAACACTTTAAAACAGATAGCT
AGCAAATTAAGAGAACAATTTGGAAATAATAAAACAATAATCTTTAAGCA
ATCCTCAGGAGGGGACCCAGAAATTGTAACGCACAGTTTTAATTGTGGAG
GGGAATTTTTCTACTGTAATTCAACACAACTGTTTAATAGTACTTGGTTT
AATAGTACTTGGAGTACTGAAGGGTCAAATAACACTGAAGGAAGTGACAC
AATCACCCTCCCATGCAGAATAAAACAATCGATAGCAATGTATGCCCCTC
CCATCAGCGGACAAATTAGATGTTCATCAAATATTACAGGGCTGCTATTA
ACAAGAGATGGTGGTAATAGCAACAATGAGTCCGAGATCTTCAGACCTGG
AGGAGGAGATATGAGGGACAATTGGAGAAGTGAATTATATAAATATAAAG
TAGTAAAAATTGAACCATTAGGAGTAGCACCCACCAAGGCAAAGAGATA
A.
```

A gp120 polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the bound molecule which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as HBsAg and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

B. Isolated Immunogens with Variant HBsAgs

Isolated immunogens including variant HBsAgs are disclosed. Suitable amino acid sequences for HBsAg are known in the art, and are disclosed, for example, in PCT Publication No. WO 2002/079217, which is incorporated herein by reference. Additional sequences for HBsAg can be found, for example, in PCT Publication No. 2004/113369 and PCT Publication No. WO 2004/09849. An exemplary HBsAg amino acid sequence, and the sequence of a nucleic acid encoding HBsAg, is shown in Berkower et al., *Virology* 321: 74-86, 2004, which is incorporated herein by reference in its entirety. An exemplary amino acid sequence of an HBsAg is set forth as follows:

(SEQ ID NO: 31)
EFITSGFLGPLLVLQAGFFLLTRILTIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIS

IPSSWAFAKYLWEWASVRFSWLSLLVPFVQWFVGLSPTVWLSAIWMMWYW

GPSLYSIVSPFIPLLPIFFCLWVYIG.

Naturally occurring variants of HBsAg are found in other hepadnaviruses and also self assemble. These include: woodchuck hepatitis, ground squirrel hepatitis and duck hepatitis virus variants. Any of these naturally occurring HBsAg variants can combine with gp120 to produce virus-like particles.

By itself, HBsAg assembles into approximately 22 nm virus-like particles. When expressed together with an HIV-1 antigenic epitope, the HBsAg fusion proteins assemble spontaneously and efficiently into virus-like particles (see Berkower et al., *Virology* 321: 75-86, 2004, which is incorporated herein by reference). Without being bound by theory, the multimeric form expresses the one or more antigenic epitopes at the lipid-water interface. These epitopes can be used to induce an immune response, such as to induce the production of neutralizing antibodies.

The preparation of HBsAg is well documented. See, for example, Harford et al. (1983) *Develop. Biol. Standard* 54:125; Greg et al. (1987) *Biotechnology* 5:479; EP-A- 0 226 846; and EP-A-0 299 108.

Fragments and variants of HBsAgs as disclosed herein are fragments and variants that retain the ability to spontaneously assemble into virus-like particles. By "fragment" of an HBsAg is intended a portion of a nucleotide sequence encoding a HBsAg, or a portion of the amino acid sequence of the protein. By "homologue" or "variant" is intended a nucleotide or amino acid sequence sufficiently identical to the reference nucleotide or amino acid sequence, respectively.

It is recognized that the gene or cDNA encoding a polypeptide can be considerably mutated without materially altering one or more the polypeptide's functions. The genetic code is well known to be degenerate, and thus different codons encode the same amino acids. Even where an amino acid substitution is introduced, the mutation can be conservative and have no material impact on the essential functions of a protein (see Stryer, *Biochemistry* 4th Ed., W. Freeman & Co., New York, N.Y., 1995). Part of a polypeptide chain can be deleted without impairing or eliminating all of its functions. Sequence variants of a protein, such as a 5' or 3' variant, can retain the full function of an entire protein. Moreover, insertions or additions can be made in the polypeptide chain for example, adding epitope tags, without impairing or eliminating its functions (Ausubel et al., *Current Protocols in Molecular Biology*, Greene Publ. Assoc. and Wiley-Intersciences, 1998). Specific substitutions include replacing one or more transmembrane spanning domains of HBsAg with a gp41 transmembrane spanning domain, such as replacing the first domain and/or third domain of HBsAg with a gp41 transmembrane spanning domain. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquitination, labeling, such as with radionucleides, and various enzymatic modifications, as will be readily appreciated by those well skilled in the art. A variety of methods for labeling polypeptides and labels useful for such purposes is well known in the art, and includes radioactive isotopes such as $^{125}$I or $^3$H, ligands that bind to or are bound by labeled specific binding partners (such as antibodies), fluorophores, chemiluminescent agents, enzymes, and antiligands or crosslinkers to produce dimers or multimers.

Functional fragments and variants of HBsAg include those fragments and variants that are encoded by nucleotide sequences that retain the ability to spontaneously assemble into virus-like particles. Functional fragments and variants can be of varying length. For example, a fragment may consist of 10 or more, 25 or more, 50 or more, 75 or more, 100 or more, or 200 or more amino acid residues of a HBsAg amino acid sequence.

A functional fragment or variant of HBsAg is defined herein as a polypeptide that is capable of spontaneously assembling into virus-like particles and/or self-aggregating into stable multimers. This includes, for example, any polypeptide six or more amino acid residues in length that is capable of spontaneously assembling into virus-like particles. Methods to assay for virus-like particle formation are well known in the art (see, for example, Berkower et al. (2004) *Virology* 321:75-86, herein incorporated by reference in its entirety).

"Homologues" or "variants" of a HBsAg are encoded by a nucleotide sequence sufficiently identical to a nucleotide sequence of hepatitis B surface antigen, examples of which are described above. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, for example using the NCBI Blast 2.0 gapped BLAST set to default parameters. Alignment may also be performed manually by inspection. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). In one embodiment, the HBsAg protein is at least about 85%, at least about 90%, at least about 95%, at least about 96%, at least about 97%, at least about 98%, at least about 99% identical to the polypeptide sequence of SEQ ID NO: 31.

One or more conservative amino acid modifications can be made in the HBsAg amino acid sequence, whether an addition, deletion or modification, that does not substantially alter the 3-dimensional structure of the polypeptide. For example, a conservative amino acid substitution does not affect the ability of the HBsAg polypeptide to self-aggregate into stable multimers. HBsAg proteins having deletions of a small number of amino acids, for example, less than about 20% (such as less than about 18%, less than about 15%, less than about 10%, less than about 8%, less than about 5%, less than about 2%, or less than about 1%) of the total number of amino acids in the wild type HBsAg protein can also be included in the fusion proteins described herein. The deletion may be a terminal deletion, or an internal deletion, so long as the deletion does not substantially affect the structure or aggregation of the fusion protein.

In certain embodiments, a variant HBsAg can include a linker sequence. This peptide is a short amino acid sequence providing a flexible linker that permits attachment of an antigenic polypeptide, such as a variant gp120 polypeptide, without disruption of the structure, aggregation (multimerization) or activity of the self-aggregating polypeptide component. Typically, a linear linking peptide consists of between two and 25 amino acids. Usually, the linear linking peptide is between two and 15 amino acids in length. In one example, the linker polypeptide is two to three amino acids in length, such as a serine and an arginine, or two serine residues and an arginine residue, or two arginine residues and a serine residue.

In other examples, the linear linking peptide can be a short sequence of alternating glycines and prolines, such as the amino acid sequence glycine-proline-glycine-proline. A linking peptide can also consist of one or more repeats of the sequence glycine-glycine-serine. Alternatively, the linear linking peptide can be somewhat longer, such as the glycine (4)-serine spacer described by Chaudhary et al., *Nature* 339: 394-397,1989.

Directly or indirectly adjacent to the remaining end of the linear linking peptide (that is, the end of the linear linking peptide not attached to the self-aggregating polypeptide component of the fusion protein) is a polypeptide sequence including at least one antigenic epitope of HIV-1, such as an epitope of gp41, such as at least one antigenic epitope of the membrane proximal region. The antigenic polypeptide can be a short peptide sequence including a single epitope. For example the antigenic polypeptide can be a sequence of amino acids as short as eight or nine amino acids, sufficient in length to provide an antigenic epitope in the context of presentation by a cellular antigen presenting complex, such as the major histocompatibility complex (MHC). The antigenic polypeptide can also be of sufficient in length to induce antibodies, such as neutralizing antibodies. Larger peptides, in excess of 10 amino acids, 20 amino acids or 30 amino acids are also suitable antigenic polypeptides, as are much larger polypeptides provided that the antigenic polypeptide does not disrupt the structure or aggregation of the HBsAg polypeptide component.

In some examples, the variant HBsAg includes one or more epitopes of the envelope protein of HIV-1, and is about 20 to about 200 amino acids in length, such as about 25 to about 150 amino acids in length, such as about 25 to about 100 amino acids in length. In several additional examples, the antigenic polypeptide includes one or more antigenic epitopes of HIV-1 gp41, such as the membrane proximal region (MPR) of gp41.

Exemplary sequences for HIV-1, as well as the amino acid sequence for full-length gp41 can be found on Genbank, EMBL and SwissProt websites. Exemplary non-limiting sequence information can be found for example, as SwissProt Accession No. PO4578, (includes gp41 and gp120, initial entry Aug. 13, 1987, last modified on Jul. 15, 1999); Genbank Accession No. HIVHXB2CG (full length HIV-1, including RNA sequence and encoded proteins, Oct. 21, 2002); Genbank Accession No. CAD23678 (gp41, Apr. 15, 2005); and Genbank Accession No. CAA65369 (Apr. 18, 2005), all of which are incorporated herein by reference. Similar information is available for HIV-2.

Suitable Env proteins are known in the art and include, for example, gp160, gp120, gp41, and gp140. Any clade of HIV is appropriate for antigen selection, including HIV clades A, B, C, and the like. HIV Gag, Pol, Nef and/or Env proteins from HIV clades A, B, C, as well as nucleic acid sequences encoding such proteins and methods for the manipulation and insertion of such nucleic acid sequences into vectors, are known (see, for example, HIV Sequence Compendium, Division of AIDS, National Institute of Allergy and Infectious Diseases, 2003, HIV Sequence Database (on the world wide web at hiv-web.lanl.gov/content/hiv-db/mainpage.html), Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Association. Exemplary Env polypeptides, for example, corresponding to clades A, B and C are represented by the sequences of Genbank® Accession Nos. U08794, K03455 and AF286227, respectively.

Variant HBsAgs can form a self-aggregating multimeric spherical or rod-shaped structure upon expression in a host cell. Similarly, the variant HBsAgs can assemble spontaneously (self-aggregate) when placed in suspension in a solution of physiological pH (for example, a pH of about 7.0 to 7.6). Thus, in the present disclosure, wherever a single or monomeric variant HBsAg is disclosed, polymeric forms are also considered to be described.

In some embodiments, an isolated immunogen includes a variant HBsAg with one or more transmembrane domains of the HBsAg replaced with a gp41 antigenic insert. The gp41 antigenic insert can include (a) an antigenic polypeptide fragment of gp41 and (b) a transmembrane spanning region of gp41. In an example, the gp41 antigenic insert includes (a) an antigenic polypeptide fragment, such as an antigenic polypeptide fragment with the amino acid sequence set forth in SEQ ID NO:1 and is between 10 and 150 amino acids in length, such as 16 and 150, and (b) a transmembrane spanning gp41 region, such as a transmembrane spanning gp41 region with the amino acid sequence set forth in SEQ ID NO: 25 ($X_5$FIMIVGGL$X_6$GLRIVFT$X_7$LSIV) in which $X_5$, $X_6$ and $X_7$ are any hydrophobic amino acid) and is between 22 and 40 amino acids in length.

In one example, the antigenic polypeptide includes the amino acid sequence of NEX$_1$X$_2$LLX$_3$LDKWASLWNWFDITNWLWYIK (SEQ ID NO: 1), wherein X$_1$, X$_2$ and X$_3$ are any amino acid. The antigenic epitope can include repeats of this sequence, such as one to five copies of SEQ ID NO: 1. As noted above, the antigenic peptide includes one or more epitopes of the envelope protein of HIV-1, and, including SEQ ID NO: 1, can be from about 28 to about 200 amino acids in length, such from about 28 to about 150 amino acids in length, such as from about 28 to about 140 amino acids in length.

In several examples, the antigenic polypeptide includes one or more of the amino acid sequences set forth below:

a) SEQ ID NO: 2   (NEQELLALDKWASLWNWFDITNWLWYIK);
b) SEQ ID NO: 3   (NEQDLLALDKWASLWNWFDITNWLWYIK);
c) SEQ ID NO: 4   (NEQDLLALDKWANLWNWFDISNWLWYIK);
d) SEQ ID NO: 5   (NEQDLLALDKWANLWNWFNITNWLWYIR);
e) SEQ ID NO: 6   (NEQELLELDKWASLWNWFDITNWLWYIK);
f) SEQ ID NO: 7   (NEKDLLALDSWKNLWNWFDITNWLWYIK);
g) SEQ ID NO: 8   (NEQDLLALDSWENLWNWFDITNWLWYIK);
h) SEQ ID NO: 9   (NEQELLELDKWASLWNWFSITQWLWYIK);
i) SEQ ID NO: 10  (NEQELLALDKWASLWNWFDISNWLWYIK);
j) SEQ ID NO: 11  (NEQDLLALDKWDNLWSWFTITNWLWYIK);
k) SEQ ID NO: 12  (NEQDLLALDKWASLWNWFDITKWLWYIK);
l) SEQ ID NO: 13  (NEQDLLALDKWASLWNWFSITNWLWYIK);
m) SEQ ID NO: 14  (NEKDLLELDKWASLWNWFDITNWLWYIK);
n) SEQ ID NO: 15  (NEQEILALDKWASLWNWFDISKWLWYIK);
o) SEQ ID NO: 16  (NEQDLLALDKWANLWNWFNISNWLWYIK);
p) SEQ ID NO: 17  (NEQDLLALDKWASLWSWFDISNWLWYIK);
q) SEQ ID NO: 18  (NEKDLLALDSWKNLWSWFDITNWLWYIK);
r) SEQ ID NO: 19  (NEQELLQLDKWASLWNWFSITNWLWYIK);
s) SEQ ID NO: 20  (NEQDLLALDKWASLWNWFDISNWLWYIK);
t) SEQ ID NO: 21  (NEQELLALDKWASLWNWFDISNWLWYIR);
or
u) SEQ ID NO: 22  (NEQELLELDKWASLWNWFNITNWLWYIK).

The antigenic polypeptide can include one of the amino acid sequences set forth as SEQ ID NOs: 2-22. A single copy of one of SEQ ID NOs: 2-22 can be included as the antigenic polypeptide. Alternatively, multiple copies of one of SEQ ID NOs: 2-22 can be included as the antigenic polypeptide. Thus, one, two, three, four or five copies of one of the amino acid sequences set forth as SEQ ID NOs: 2-22 can be included as the antigenic polypeptide.

In additional embodiments, more than one of these sequences can be included in the antigenic polypeptide. Thus, in several examples, two, three, four or five of the amino acid sequences set forth as SEQ ID NOs: 2-22 can be included as the antigenic polypeptide in tandem. Each amino acid sequence included in the antigenic polypeptide can be present only a single time, or can be repeated.

In some embodiments, the transmembrane spanning gp41 region includes the amino acid sequence set forth in SEQ ID NO: 25. In this sequence, X$_1$, X$_2$ and X$_3$ are any amino acid and X$_4$, X$_5$, and X$_6$ are any hydrophobic amino acid and the transmembrane spanning gp41 region is between 22 and 40 amino acids in length. In several examples, the antigenic polypeptide includes one or more of the amino acid sequences set forth below:

a) SEQ ID NO: 26  (IFIMIVGGLIGLRIVFTVLSIV)
b) SEQ ID NO: 27  (LFIMIVGGLIGLRIVFTALSIV);
or
c) SEQ ID NO: 28  (IFIMIVGGLVGLRIVFTALSIV)

The HBsAg variants can include one or more transmembrane spanning domains that include one of the amino acid sequences set forth as SEQ ID NOs: 26-28. A single gp41 transmembrane can be included in the variant HBsAg. Alternatively, multiple gp41 transmembrane domains with amino acid sequences set forth as SEQ ID NOs: 26-28 can be included within the variant HBsAg. Thus, one, two, three, four or five gp41 transmembrane domains with one of the amino acid sequences set forth as SEQ ID NOs: 26-28 can be included in the variant HBsAg.

In one particular embodiment, an isolated immunogen includes a variant HBsAg in which the first transmembrane spanning domain of the HBsAg is replaced by a gp41 antigenic insert. For example, the gp41 antigenic insert replaces at least the first 29 amino acid residues of SEQ ID NO:20, for example amino acid residues 1-35 of SEQ ID NO: 31. In another example, the gp41 antigenic insert replaces amino acid residues 1-32 of SEQ ID NO: 31. In yet another example, the gp41 antigenic insert replaces amino acid residues 1-29 of SEQ ID NO: 31. In a particular example, an isolated immunogen includes a variant HBsAg in which the first transmembrane spanning domain of the HBsAg is replaced by a gp41 antigenic insert that has the amino acid sequence set forth as SEQ ID NO: 29.

In another particular embodiment, an isolated immunogen includes a variant HBsAg in which the third transmembrane spanning domain of the HBsAg is replaced by a gp41 antigenic insert. For example, the gp41 antigenic insert replaces at least 29 amino acids residues of SEQ ID NO: 31, for example amino acid residues 150-190 of SEQ ID NO: 31. In another example, the gp41 antigenic insert replaces amino acid residues 153-187 of SEQ ID NO: 31. In yet another example, the gp41 antigenic insert replaces amino acid residues 156-185 of SEQ ID NO: 31. In a particular example, an isolated immunogen including a variant HBsAg in which the third transmembrane spanning domain of the HBsAg is replaced by a gp41 antigenic insert has the amino acid sequence set forth as SEQ ID NO: 44.

In an even more particular embodiment, an isolated immunogen includes a variant HBsAg in which more than one transmembrane spanning domains of HBsAg have been replaced with an antigenic insert. In one example, an isolated immunogen includes a varaint HBsAg in which the first and the third transmembrane spanning domains of the HBsAg are replaced by a gp41 antigenic insert. For example, the gp41 antigenic insert replaces amino acid residues 1-35 and 150-190 of SEQ ID NO: 31. In another example, the gp4l antigenic insert replaces amino acid residues 1-32 and 153-187 of SEQ ID NO: 31. In yet another example, the gp41 antigenic insert replaces amino acid residues 1-29 and 156-185 of SEQ ID NO: 31. In a particular example, an isolated immunogen including a variant HBsAg in which the third transmembrane spanning domain of the HBsAg is replaced by a gp41 antigenic insert has the amino acid sequence set forth as:

(SEQ ID NO: 44)
MKTIIALSYIFCLVFAQDLPGNDNNSEFITSGFLGPLLVLQAGFFLLTRI

LTIPQSLDSWWTSLNFLGGSPVCLGQNSQSPTSNHSPTSCPPICPGYRWM

CLRRFIIFLFILLLCLIFLLVLLDYQGMLPVCPLIPGSTTTSTGPCKTCT

TPAQGNSKFPSCCCTKPTDGNCTCININEKELLELDKWASLWNWFDITNW

LWYIRLFIMIVGGLIGLRIVFAVLSIVVGLSPTVWLSAIWMMWYWGPSLY

SIVSPFIPLLPIFFCLWVYIG.

In one example of an isolated immunogen, in which the first transmembrane domain of HBsAg is replaced with the MPR and transmembrane domain of gp41 has the amino acid sequence set forth as:

(SEQ ID NO: 29)
MKTIIALSYIFCLVFAQDLPGNDNNSEFNEKELLELDKWASLWNWFDITN

WLWYIRLFIMIVGGLIGLRIVFAVLSIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIP

IPSSWAFAKYLWEWASSVRFSWLSLLVPFVQWFVGLSPTVWLSAIWMMWY

WGPSLYSIVSPFIPLLPIFFCLWVYIG.

In one example of the isolated immunogen, the third transmembrane domain of HBsAg is replaced with the MPR and transmembrane domain of gp41 has the amino acid sequence set forth as:

(SEQ ID NO: 44)
MKTIIALSYIFCLVFAQDLPGNDNNSEFITSGFLGPLLVLQAGFFLLTRI

LTIPQSLDSWWTSLNFLGGSPVCLGQNSQSPTSNHSPTSCPPICPGYRWM

CLRRFIIFLFILLLCLIFLLVLLDYQGMLPVCPLIPGSTTTSTGPCKTCT

TPAQGNSKFPSCCCTKPTDGNCTCININEKELLELDKWASLWNWFDITNW

LWYIRLFIMIVGGLIGLRIVFAVLSIVVGLSPTVWLSAIWMMWYWGPSLY

SIVSPFIPLLPIFFCLWVYIG.

In an example, an isolated immunogen is provided in which the first transmembrane domain and third domain of HBsAG is each replaced with the MPR and transmembrane domain of gp41 and has the amino acid sequence set forth as:

(SEQ ID NO: 45)
MKTIIALSYIFCLVFAQDLPGNDNNSEFNEKELLELDKWASLWNWFDITN

WLWYIRLFIMIVGGLIGLRIVFAVLSIPQSLDSWWTSLNFGGSPVCLGQN

SQSPTSNHSPTSCPPICPGYRWMCLRRFIIFLFILLCLIFLLVLLDYQGM

LPVCPLIPGSTTTSTGPCKTCTTPAQGNSKFPSCCCTKPTDGNCTCIPIN

EKELLELDKWASLWNWFDITNWLWYIRLFIMIVGGLIGLRIVFAVLSIVV

GLSPTVWLSAIWMMWYWGPSLYSIVSPFIPLLPIFFCLWVYIG.

In one example, an isolated immunogen is provided in which the first transmembrane domain of HBsAg is replaced with the MPR and transmembrane domain of gp41 and an additional MPR is inserted just proximal to the third membrane spanning domain of HBsAg. In another example, an isolated immunogen is provided in which multiple MPRs are inserted within the HBsAg, such as two, three, four or more MPRs are inserted just proximal to the third membrane spanning domain of HBsAg. In yet another example, an isolated immunogen is provided in which a MPR and transmembrane domain of gp41 is inserted following the fourth HBsAg membrane spanning domain.

The variant HBsAg can optionally include additional elements, such as a leader sequence or a suitable T cell epitope. Generally, a T cell epitope is about eight to about ten amino acids in length, such as about nine amino acid in length, and binds major histocompatibility complex (MHC), such as HLA 2, for example, HLA 2.2. Examples of suitable T cell epitopes include, but are not limited to, ASLWNWFNIT-NWLWY (SEQ ID NO: 32) and IKLFIMIVGGLVGLR (SEQ ID NO: 33).

The variant HBsAg may also include a CAAX (SEQ ID NO: 34) sequence, for isoprenyl addition in vivo. In this sequence, C is cysteine, A is an aliphatic amino acid and X is any amino acid. The X residue determines which isoprenoid will be added to the cysteine. When X is a methionine or serine, the farnesyl-transferase transfers a farnesyl, and when X is a leucine or isoleucine, the geranygeranyl-transferase I transfers a geranygeranyl group. In general, aliphatic amino acids have protein side chains containing only carbon or hydrogen atoms. Aliphatic amino acids include proline (P), glycine (G), alanine (A), valine (V), leucine (L), and isoleucine (I), presented in order from less hydrophobic to more hydrophobic. Although methionine has a sulphur atom in its side-chain, it is largely non-reactive, meaning that methionine effectively substitutes well with the true aliphatic amino acids. Further examples of HBsAg variant polypeptides that can be incorporated into compositions and methods disclosed herein are given in PCT Publication No. WO 2010/017209 which is hereby incorporated by reference in its entirety.

C. Polynucleotides Encoding Variant gp120 Polypeptides and/or Variant HBsAgs

Nucleic acids encoding the variant gp120 polypeptides and/or variant HBsAgs (including both natural variants of HBsAg as well as those disclosed herein) described herein are also provided. These nucleic acids include deoxyribonucleotides (DNA, cDNA) or ribodeoxynucleotides (RNA) sequences, or modified forms of either nucleotide, which encode the variant gp120 polypeptides and HBsAgs described herein. The term includes single and double stranded forms of DNA and/or RNA. The nucleic acids can be operably linked to expression control sequences, such as, but not limited to, a promoter.

The nucleic acids that encode the variant gp120 polypeptides disclosed herein include a polynucleotide sequence that encodes a variant gp120 polypeptide including a gp120 with at least a deletion of at least 8, such as at least 9, at least 10, at least 11, consecutive residues of the fourth conserved loop (C4) between residues 419 and 434 of gp120 of SEQ ID NO: 47.

In one example, nucleic acids that encode a variant gp120 polypeptide with a V1V2 deleted gp120 without a beta 20-21 loop deletion according to HXB2 numbering has the nucleotide sequence set forth as:

(SEQ ID NO: 48)
GGTACCTGTGTGGAGAGAAGCAACCACCACTCTATTTTGTGCATCAGATG

CTAAAGCCTATGATACAGAGGTACATAATGTTTGGGCCACACATGCCTGT

```
GTACCCACAGACCCCAACCCACAAGAAGTAGTATTGGGAAATGTGACAGA

AAATTTTAACATGTGGAAAAATAACATGGTAGATCAGATGCATGAGGATA

TAATCAGTTTATGGGATGAAAGCCTAAAGCCATGTGTAAAATTAACCCCA

CTCTCGGTCCAGGCCTGTCCAAAGGTATCCTTTCAGCCAATTCCCATACA

TTATTGTGTCCCGGCTGGGTTTGCGATGCTAAAGTGTAACAATAAGACAT

TCAATGGATCAGGACCATGCACAAATGTCAGCACAGTACAATGTACACAT

GGAATTAGGCCAGTGGTGTCAACTCAACTGCTGTTAAATGGCAGTCTAGC

AGAAGAAGACATAGTAATTAGATCTGAAAATTTCACAGACAATGCTAAAA

CCATAATAGTACAGCTAAATGAATCTGTAGTAATTAATTGTACAAGACCC

AACAACAATACAAGAAGAAGGTTATCTATAGGACCAGGGAGAGCATTTTT

ATGCAAGAAGAAACATAATAGGAGATATAAGACAAGCACATTGTAACATT

AGTAGAGCAAAATGGAATAACACTTTACAACAGATAGTTATAAAATTAAG

AGAAAAATTTAGGAATAAAACAATAGCCTTTAATCAATCCTCAGGAGGGG

ACCCAGAAATTGTAATGCACAGTTTTAATTGTGGAGGGGAATTTTTCTAC

TGTAATACAGCACAACTGTTTAATAGTACTTGGAATGTTACTGGAGGGAC

AAATGGCACTGAAGGAAATGACATAATCACACTCCAATGCAGAATAAAAC

AAATTATAAATATGTGGCAGAAAGTAGGAAAAGCAATGTATGCCCCTCCC

ATCACAGGACAAATTAGATGTTCATCAAATATTACAGGGCTGCTACTAAC

AAGAGATGGAGGTAATAGTACTGAGACTGAGACTGAGATCTTCAGACCTG

GAGGAGGAGATATGAGGGACAATTGGAGAAGTGAATTATATAAATATAAA

GTAGTAAGAATTGAACCAATAGGAGTAGCACCCACCAGGGCAAAGAGATG

ACTAGTCGCGGCCGCTTTCGAATCTAGA.
```

In one example, nucleic acids that encode a variant gp120 polypeptide with a V1V2 deleted gp120 with a beta 20-21 loop deletion according to HXB2 numbering has the nucleotide sequence set forth as:

```
                                          (SEQ ID NO: 49)
GGTACCTGTGTGGAGAGAAGCAACCACCACTCTATTTTGTGCATCAGATG

CTAAAGCCTATGATACAGAGGTACATAATGTTTGGGCCACACATGCCTGT

GTACCCACAGACCCCAACCCACAAGAAGTAGTATTGGGAAATGTGACAGA

AAATTTTAACATGTGGAAAAATAACATGGTAGATCAGATGCATGAGGATA

TAATCAGTTTATGGGATGAAAGCCTAAAGCCATGTGTAAAATTAACCCCA

CTCTCGGTCCAGGCCTGTCCAAAGGTATCCTTTCAGCCAATTCCCATACA

TTATTGTGTCCCGGCTGGGTTTGCGATGCTAAAGTGTAACAATAAGACAT

TCAATGGATCAGGACCATGCACAAATGTCAGCACAGTACAATGTACACAT

GGAATTAGGCCAGTGGTGTCAACTCAACTGCTGTTAAATGGCAGTCTAGC

AGAAGAAGACATAGTAATTAGATCTGAAAATTTCACAGACAATGCTAAAA

CCATAATAGTACAGCTAAATGAATCTGTAGTAATTAATTGTACAAGACCC

AACAACAATACAAGAAGAAGGTTATCTATAGGACCAGGGAGAGCATTTTA

TGCAAGAAGAAACATAATAGGAGATATAAGACAAGCACATTGTAACATTA

GTAGAGCAAAATGGAATAACACTTTACAACAGATAGTTATAAAATTAAGA

GAAAAATTTAGGAATAAAACAATAGCCTTTAATCAATCCTCAGGAGGGGA

CCCAGAAATTGTAATGCACAGTTTTAATTGTGGAGGGGAATTTTTCTACT

GTAATACAGCACAACTGTTTAATAGTACTTGGAATGTTACTGGAGGGACA

AATGGCACTGAAGGAAATGACATAATCACACTCCAATGCAGAATAAAACA

GCTAGCAATGTATGCCCCTCCCATCACAGGACAAATTAGATGTTCATCAA

ATATTACAGGGCTGCTACTAACAAGAGATGGAGGTAATAGTACTGAGACT

GAGACTGAGATCTTCAGACCTGGAGGAGGAGATATGAGGGACAATTGGAG

AAGTGAATTATATAAATATAAAGTAGTAAGAATTGAACCAATAGGAGTAG

CACCCACCAGGGCAAAGAGATGACTAGTCGCGGCCGCTTTC.
```

In an example, a polynucleotide sequence that encodes a variant gp120 polypeptide further includes a nucleic acid sequence molecule encoding a wild-type HBsAg or a variant thereof. The nucleic acids that encode the variant HBsAgs disclosed herein include a polynucleotide sequence that encodes a variant HBsAgs including a HBsAg with one or more MPRs and/or one or more transmembrane domains of the HBsAg replaced with a gp41 antigenic insert.

In one example, nucleic acids that encode a variant HBsAg in which a third transmembrane of HBsAg is replaced with a gp41 antigenic insert has the nucleotide sequence set forth as

```
                                          (SEQ ID NO: 46)
GGTACCGTCGACAGCAAAAGCAGGGGATAATTCTATTAACCATGAAGACT

ATCATTGCTTTGAGCTACATTTTCTGTCTGGTTTTCGCCCAAGACCTTCC

AGGAAATGACAACAACAGCGAATTCATCACCTCCGGCTTCCTGGGCCCCC

TGCTGGTCCTGCAGGCCGGGTTCTTCCTGCTGACCCGCATCCTCACCATC

CCCCAGTCCCTGGACTCGTGGTGGACCTCCCTCAACTTTCTGGGGGGCTC

CCCCGTGTGTCTGGGCCAGAACTCCCAGTCCCCCACCTCCAACCACTCCC

CCACCTCCTGCCCCCCCATCTGCCCCGGCTACCGCTGGATGTGCCTGCGC

CGCTTCATCATCTTCCTGTTCATCCTGCTGCTGTGCCTGATCTTCCTGCT

GGTGCTGCTGGACTACCAGGGCATGCTGCCCGTGTGCCCCCTGATCCCCG

GCTCCACCACCACCTCCACCGGCCCCTGCAAGACCTGCACCACCCCCGCC

CAGGGCAACTCCAAGTTCCCCTCCTGCTGCTGCACCAAGCCCACCGACGG

CAACTGCACCTGCATCAATATTAATGAAAAGAATTATTGGAATTGGATA

AATGGGCAAGTTTGTGGAATTGGTTTGACATAACAAACTGGCTGTGGTAT

ATAAGATTATTCATAATGATAGTAGGAGGCTTGATAGGTTTAAGAATAGT

TTTTGCTGTACTTTCTATAGTAGTGGGCCTGTCCCCCACCGTGTGGCTGT

CCGCCATCTGGATGATGTGGTACTGGGGCCCCTCCCTGTACTCCATCGTG

TCCCCCTTCATCCCCCTGCTGCCCATCTTCTTCTGCCTGTGGGTGTACAT

CTGACTAGTGAGCTC.
```

The variant gp120 polypeptides, variant HBsAgs polypeptides (natural and recombinant) and the polynucleotides encoding them described herein can be used to produce pharmaceutical compositions, including compositions suitable for prophylactic and/or therapeutic administration. These compositions can be used to induce an immune response to HIV, such as a protective immune response. However, the compositions can also be used in various assays, such as in assays designed to detect an HIV-1 infection.

Methods and plasmid vectors for producing the polynucleotides encoding variant gp120 polypeptides and/or variant HBsAgs and for expressing these polynucleotides in bacterial and eukaryotic cells are well known in the art, and specific methods are described in Sambrook et al. (In *Molecular Cloning: A Laboratory Manual*, Ch. 17, CSHL, New York, 1989). Such variant gp120 polypeptides and variant HBsAgs may be made in large amounts, are easy to purify, and can be used to elicit an immune response, including an antibody response and/or a T cell response. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Proteins, including variant gp120 polypeptides, may be isolated from protein gels, lyophilized, ground into a powder and used as an antigen.

Vector systems suitable for the expression of polynucleotides encoding variant gp120 polypeptides and/or HBsAgs or variant thereof include, in addition to the specific vectors described in the examples, the pUR series of vectors (Ruther and Muller-Hill, *EMBO J.* 2:1791, 1983), pEX1-3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177-3 (Amann and Brosius, *Gene* 40:183, 1985) and pET-3 (Studiar and Moffatt, *J. Mol. Biol.* 189:113, 1986), as well as the pCMV/R vector. The CMV/R promoter is described in, among other places, PCT Application No. PCT/US02/30251 and PCT Publication No. WO03/028632.

The DNA sequence can also be transferred from its existing context to other cloning vehicles, such as other plasmids, bacteriophages, cosmids, animal viruses and yeast artificial chromosomes (YACs) (Burke et al., *Science* 236:806-812, 1987). These vectors may then be introduced into a variety of hosts including somatic cells, and simple or complex organisms, such as bacteria, fungi (Timberlake and Marshall, *Science* 244:1313-1317, 1989), invertebrates, plants (Gasser and Fraley, *Science* 244:1293, 1989), and animals (Pursel et al., *Science* 244:1281-1288, 1989), which cell or organisms are rendered transgenic by the introduction of the heterologous cDNA. Specific, non-limiting examples of host cells include mammalian cells (such as CHO or HEK293 cells), insect cells (Hi5 or SF9 cells) or yeast cells.

For expression in mammalian cells, a cDNA sequence may be ligated to heterologous promoters, such as the simian virus (SV) 40 promoter in the pSV2 vector (Mulligan and Berg, *Proc. Natl. Acad. Sci. USA* 78:2072-2076, 1981), or the cytomegalovirus promoter, and introduced into cells, such as monkey COS-1 cells (Gluzman, *Cell* 23:175-182, 1981), to achieve transient or long-term expression. The stable integration of the chimeric gene construct may be maintained in mammalian cells by biochemical selection, such as neomycin (Southern and Berg, *J. Mol. Appl. Genet.* 1:327-341, 1982) and mycophenolic acid (Mulligan and Berg, *Proc. Natl. Acad. Sci. USA* 78:2072-2076, 1981).

DNA sequences can be manipulated with standard procedures such as restriction enzyme digestion, fill-in with DNA polymerase, deletion by exonuclease, extension by terminal deoxynucleotide transferase, ligation of synthetic or cloned DNA sequences, site-directed sequence-alteration via single-stranded bacteriophage intermediate or with the use of specific oligonucleotides in combination with PCR or other in vitro amplification.

A cDNA sequence (or portions derived from it) such as a cDNA encoding a variant HBsAg can be introduced into eukaryotic expression vectors by conventional techniques. These vectors are designed to permit the transcription of the cDNA in eukaryotic cells by providing regulatory sequences that initiate and enhance the transcription of the cDNA and ensure its proper splicing and polyadenylation. Vectors containing the promoter and enhancer regions of the SV40 or long terminal repeat (LTR) of the Rous Sarcoma virus and polyadenylation and splicing signal from SV40 are readily available (Mulligan et al., *Proc. Natl. Acad. Sci. USA* 78:1078-2076, 1981; Gorman et al., *Proc. Natl. Acad. Sci USA* 78:6777-6781, 1982). The level of expression of the cDNA can be manipulated with this type of vector, either by using promoters that have different activities (for example, the baculovirus pAC373 can express cDNAs at high levels in *S. frugiperda* cells (Summers and Smith, In *Genetically Altered Viruses and the Environment*, Fields et al. (Eds.) 22:319-328, CSHL Press, Cold Spring Harbor, N.Y., 1985) or by using vectors that contain promoters amenable to modulation, for example, the glucocorticoid-responsive promoter from the mouse mammary tumor virus (Lee et al., *Nature* 294:228, 1982). The expression of the cDNA can be monitored in the recipient cells 24 to 72 hours after introduction (transient expression).

In addition, some vectors contain selectable markers such as the gpt (Mulligan and Berg, *Proc. Natl. Acad. Sci. USA* 78:2072-2076, 1981) or neo (Southern and Berg, *J. Mol. Appl. Genet.* 1:327-341, 1982) bacterial genes. These selectable markers permit selection of transfected cells that exhibit stable, long-term expression of the vectors (and therefore the cDNA). The vectors can be maintained in the cells as episomal, freely replicating entities by using regulatory elements of viruses such as papilloma (Sarver et al., *Mol. Cell Biol.* 1:486, 1981) or Epstein-Barr (Sugden et al., *Mol. Cell Biol.* 5:410, 1985). Alternatively, one can also produce cell lines that have integrated the vector into genomic DNA. Both of these types of cell lines produce the gene product on a continuous basis.

One can also produce cell lines that have amplified the number of copies of the vector (and therefore of the cDNA as well) to create cell lines that can produce high levels of the gene product (Alt et al., *J. Biol. Chem.* 253:1357, 1978).

The transfer of DNA into eukaryotic, in particular human or other mammalian cells, is conventional. The vectors are introduced into the recipient cells as pure DNA (transfection) by, for example, precipitation with calcium phosphate (Graham and vander Eb, *Virology* 52:466, 1973) or strontium phosphate (Brash et al., *Mol. Cell Biol.* 7:2013, 1987), electroporation (Neumann et al., *EMBO J* 1:841, 1982), lipofection (Feigner et al., *Proc. Natl. Acad. Sci USA* 84:7413, 1987), DEAE dextran (McCuthan et al., *J. Natl. Cancer Inst.* 41:351, 1968), microinjection (Mueller et al., *Cell* 15:579, 1978), protoplast fusion (Schafner, *Proc. Natl. Acad. Sci. USA* 77:2163-2167, 1980), or pellet guns (Klein et al., *Nature* 327:70, 1987). Alternatively, the cDNA, or fragments thereof, can be introduced by infection with virus vectors. Systems are developed that use, for example, retroviruses (Bernstein et al., *Gen. Engr'g* 7:235, 1985), adenoviruses (Ahmad et al., *J. Virol.* 57:267, 1986), or Herpes virus (Spaete et al., *Cell* 30:295, 1982). Polynucleotides that encode proteins, such as variant gp120 polypeptides, can also be delivered to target cells in vitro via non-infectious systems, for instance liposomes.

Using the above techniques, the expression vectors containing a polynucleotide encoding a variant gp120 polypeptide and/or variant HBsAg as described herein or cDNA, or fragments or variants or mutants thereof, can be introduced into human cells, mammalian cells from other species or non-mammalian cells as desired. The choice of cell is determined by the purpose of the treatment. For example, monkey COS cells (Gluzman, Cell 23:175-182, 1981) that produce high levels of the SV40 T antigen and permit the replication of vectors containing the SV40 origin of replication may be used. Similarly, Chinese hamster ovary (CHO), mouse NIH 3T3 fibroblasts or human fibroblasts can be used.

The present disclosure, thus, encompasses recombinant vectors that comprise all or part of the polynucleotides encoding self-aggregating variant gp120 polypeptides with HBsAgs (or variant HBsAgs) or cDNA sequences, for expression in a suitable host, either alone or as a labeled or otherwise detectable protein. The DNA is operatively linked in the vector to an expression control sequence in the recombinant DNA molecule so that the variant molecules can be expressed. The expression control sequence may be selected from the group consisting of sequences that control the expression of genes of prokaryotic or eukaryotic cells and their viruses and combinations thereof. The expression control sequence may be specifically selected from the group consisting of the lac system, the tip system, the tac system, the trc system, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Any host cell can be transfected with the vector of this disclosure. Exemplary host cells include, but are not limited to *E. coli, Pseudomonas, Bacillus subtilis, Bacillus stearothermophilus* or other bacilli; other bacteria; yeast; fungi; insect; mouse or other animal; plant hosts; or human tissue cells.

Multimeric forms of a variant gp120-HBsAg particle can be recovered (such as for administration to a subject, or for other purposes) using any of a variety of methods known in the art for the purification of recombinant polypeptides. The variant gp120 polypeptides and variant HBsAgs disclosed herein can produced efficiently by transfected cells and can be recovered in quantity using any purification process known to those of skill in the art, such as a nickel (NTA-agarose) affinity chromatography purification procedure.

A variety of common methods of protein purification may be used to purify the disclosed variants. Such methods include, for instance, protein chromatographic methods including ion exchange, gel filtration, HPLC, monoclonal antibody affinity chromatography, hydrophobic interaction chromatography, and isolation of insoluble protein inclusion bodies after over production.

In one embodiment one or more purification affinity-tags, for instance a six-histidine sequence, is recombinantly fused to the protein, such as the variant HBsAg or variant gp120 polypeptide, and used to facilitate polypeptide purification (optionally, in addition to another functionalizing portion of the protein, such as a targeting domain or another tag, or a fluorescent protein, peptide, or other marker).

Commercially produced protein expression/purification kits provide tailored protocols for the purification of proteins made using each system. See, for instance, the QIAEXPRESS™ expression system from QIAGEN™ (Chatsworth, Calif.) and various expression systems provided by INVITROGEN™ (Carlsbad, Calif.). Where a commercial kit is employed to produce a protein, such as a variant HBsAg, the manufacturer's purification protocol is a preferred protocol for purification of that protein. For instance, proteins expressed with an amino-terminal hexa-histidine tag can be purified by binding to nickel-nitrilotriacetic acid (Ni-NTA) metal affinity chromatography matrix (*The QIAexpressionist*, QIAGEN, 1997).

D. Therapeutic Methods and Pharmaceutical Compositions

Polynucleotides encoding the variant gp120 polypeptides and/or variant HBsAgs are disclosed herein, and variant gp120 polypeptides and/or HBsAgs can be administered to a subject in order to generate an immune response to HIV-1. In one example, the immune response is a protective immune response. Thus, the polynucleotides and polypeptides disclosed herein can be used in a vaccine, such as a vaccine to prevent subsequent infection with HIV. In some examples the disclosed variant polypeptides are administered with HBsAg or variant HBsAg, for example as a virus like particle.

A therapeutically effective amount of variant gp120 polypeptide, a virus-like particle including these variant pg120s, or a polynucleotide encoding one or more of these polypeptides can be administered to a subject to prevent, inhibit or to treat a condition, symptom or disease, such as acquired immunodeficiency syndrome (AIDS). As such, the variant gp120 polypetides and polynucleotides encoding variant gp120 peptides can be administered as vaccines to prophylactically or therapeutically induce or enhance an immune response. For example, the pharmaceutical compositions described herein can be administered to stimulate a protective immune response against HIV, such as a HIV-1. In some examples, a disclosed variant gp120 polypeptide is administered to a subject either alone or in combination with HBsAgs or variant HBsAgs (such as virus-like particles including HBsAgs or any of the variant HBsAgs disclosed in U.S. Provisional application 61/086,098, filed on Aug. 4, 2008, which is incorporated herein by reference in its entirety. A single administration can be utilized to prevent or treat an HIV infection, or multiple sequential administrations can be performed.

In exemplary applications, compositions are administered to a subject infected with HIV, or likely to be exposed to an infection, in an amount sufficient to raise an immune response to HIV. Administration induces a sufficient immune response to reduce viral load, to prevent or lessen a later infection with the virus, or to reduce a sign or a symptom of HIV infection. Amounts effective for this use will depend upon various clinical parameters, including the general state of the subject's health, and the robustness of the subject's immune system, amongst other factors. A therapeutically effective amount of the compound is that which provides either subjective relief of one or more symptom(s) of HIV infection, an objectively identifiable improvement as noted by the clinician or other qualified observer, a decrease in viral load, an increase in lymphocyte count, such as an increase in CD4 cells, or inhibition of development of symptoms associated with infection.

The variant gp120 polypeptides alone or in combination with HBsAgs or variant HBsAgs (such as virus-like particles including HBsAgs or any of the variant HBsAgs disclosed in U.S. Provisional application 61/086,098, filed on Aug. 4, 2008), polynucleotides encoding them can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. The variant gp120 polypeptides alone or in combination with HBsAgs or variant HBsAgs or polynucleotides encoding them can be administered in a formulation including a carrier or excipient. A wide variety of suitable excipients are known in the art, including physiological phosphate buffered saline (PBS), and the like. Optionally, the formulation can include additional components, such as aluminum hydroxylphophosulfate, alum, diphtheria $CRM_{197}$, or liposomes. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Aluminum salts may also be used as adjuvants to produce an immune response.

In one embodiment, the variant gp120 polypeptides alone or in combination with HBsAgs or variant HBsAgs is mixed with an adjuvant containing two or more of a stabilizing detergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, for example, Schmolka, *J. Am. Oil. Chem. Soc.* 54:110, 1977; and Hunter et al., *J. Immunol* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

An adjuvant can be included in the composition. In one example, the adjuvant is a water-in-oil emulsion in which antigen solution is emulsified in mineral oil (such as Freund's incomplete adjuvant or montanide-ISA). In one embodiment, the adjuvant is a mixture of stabilizing detergents, micelle-forming agent, and oil available under the name PROVAX® (IDEC Pharmaceuticals, San Diego, Calif.). Other examples of suitable adjuvants are listed in the terms section of this specification.

In another embodiment, a pharmaceutical composition includes a nucleic acid encoding variant gp120 polypeptide alone or in combination with HBsAgs or variant HBsAgs disclosed herein. A therapeutically effective amount of the immunogenic polynucleotide can be administered to a subject in order to generate an immune response, such as a protective immune response.

One approach to administration of nucleic acids is direct immunization with plasmid DNA, such as with a mammalian expression plasmid. As described above, the nucleotide sequence encoding a variant gp120 polypeptide alone or in combination with HBsAgs or variant HBsAgs can be placed under the control of a promoter to increase expression of the molecule. Suitable vectors are described, for example, in U.S. Pat. No. 6,562,376.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. No. 5,593,972 and U.S. Pat. No. 5,817,637 (which describe operatively linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids, and immune-stimulating constructs, or ISCOMS™, negatively charged cage-like structures of 30-40 nm in size formed spontaneously on mixing cholesterol and QUILA™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, a variant gp120 polypeptide alone or in combination with HBsAgs or variant HBsAgs as disclosed herein can also be expressed by an attenuated viral host or vector, or a bacterial vector. Recombinant adeno-associated virus (AAV), herpes virus, retrovirus, or other viral vectors can be used to express the peptide or protein, thereby eliciting a CTL response.

In one embodiment, a nucleic acid encoding the variant gp120 polypeptide alone or in combination with HBsAgs or variant HBsAgs is introduced directly into cells. For example, the nucleic acid may be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues subject to or in proximity to a site of infection. Dosages for injection are usually around 0.5 μg/kg to about 50 mg/kg, and typically are about 0.005 mg/kg to about 5 mg/kg (see, e.g., U.S. Pat. No. 5,589,466).

In one specific, non-limiting example, a pharmaceutical composition for intravenous administration, would include about 0.1 µg to 10 mg of a variant gp120 polypeptide alone or in combination with HBsAgs or variant HBsAgs per subject per day. Dosages from 0.1 pg to about 100 mg per subject per day can be used, particularly if the composition is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceuticals Sciences*, 19th Ed., Mack Publishing Company, Easton, Pa. (1995).

The compositions can be administered, either systemically or locally, for therapeutic treatments, such as to treat an HIV infection. In therapeutic applications, a therapeutically effective amount of the composition is administered to a subject infected with HIV, such as, but not limited to, a subject exhibiting signs or symptoms of AIDS. Single or multiple administrations of the compositions can be administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of the HIV infection without producing unacceptable toxicity to the subject.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa. (1995). Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly (see Kreuter, *Colloidal Drug Delivery Systems*, J. Kreuter, ed., Marcel Dekker, Inc., New York, N.Y., pp. 219-342 (1994); Tice & Tabibi, *Treatise on Controlled Drug Delivery*, A. Kydonieus, ed., Marcel Dekker, Inc. New York, N.Y., pp. 315-339 (1992)). In one example, virus like particles are in the range of 10-30 nm.

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. Nos. 5,055,303; 5,188,837; 4,235,871; 4,501,728; 4,837,028; 4,957,735; and 5,019,369; 5,055,303; 5,514,670; 5,413,797; 5,268,164; 5,004,697; 4,902,505; 5,506,206; 5,271,961; 5,254,342; and 5,534,496).

E. Immunodiagnostic Reagents and Kits

In addition to the therapeutic methods provided above, any of the variant gp120 polypeptides and variant HBsAgs or combinations thereof disclosed herein can be utilized to produce antigen specific immunodiagnostic reagents, for example, for serosurveillance. Immunodiagnostic reagents can be designed from any of the antigenic polypeptide described herein. For example, the presence of serum antibodies to HIV can be monitored using the isolated immunogens disclosed herein, such as to detect an HIV infection. Generally, the method includes contacting a sample from a subject, such as, but not limited to a blood, serum, plasma, urine or sputum sample from the subject with one or more of the variant molecules disclosed herein and detecting binding of antibodies in the sample to the variant molecule. For example, the method can include contacting a sample from a subject, such as, but not limited to a blood, serum, plasma, urine or sputum sample from the subject with one or more of the variant gp120 polypeptides disclosed herein and detecting binding of antibodies in the sample to the variant gp120 polypeptide. The binding can be detected by any means known to one of skill in the art, including the use of labeled secondary antibodies that specifically bind the antibodies from the sample. Labels include radiolabels, enzymatic labels, and fluorescent labels.

Any such immunodiagnostic reagents can be provided as components of a kit. Optionally, such a kit includes additional components including packaging, instructions and various other reagents, such as buffers, substrates, antibodies or ligands, such as control antibodies or ligands, and detection reagents.

The disclosure is illustrated by the following non-limiting Examples.

EXAMPLES

Example 1

Materials and Methods

This example describes the materials and methods used in Examples 2 and 3.

Antibodies and antigens: Antibodies were obtained from the NIH AIDS Research and Reference Reagent Program. They include: monoclonal 2G12 (Trkola et al., *J. Virol.* 70, 1100-1108, 1996), monoclonal IgG1 b12 (Burton et al., *Science* 266,1024-1027, 1994), (Posner et al., *J. Acquir. Immune Defic. Syndr. Hum. Retrovirol.* 6, 7-14, 1993), and polyclonal HIV immunoglobulin. Multivalent CD4-Ig was obtained from the NIH (Arthos et al., *J. Biol. Chem.* 277, 11456-11464, 2002). Aldrithiol-2 inactivated HIV-1 virions of the IIIB strain or SHIV virions of the 89.6 were obtained from the AIDS Vaccine Program, NCI (Lifson et al., *AIDS Research* 20, 772-787, 2004).

DNA mutants: Plasmids coding for HIV gp120 of the IIIB and 89.6 strains (Collman et al., *J. Virol.* 66, 7517-7521, 1992) were obtained. The gp120 genes were cloned downstream of the baculovirus polyhedrin promoter in a pfastbac vector in tandem with codon-optimized synthetic HBsAg and the influenza hemagglutinin signal peptide, and V1V2 regions were deleted as described in Berkower et al., Virology 321, 75-86, 2004, incorporated herein by reference in its entirety. To create loop deletions, the pfastbac plasmids were mutagenized by the QuickChange® method using non-overlapping primer pairs shown in Table 1. When the ends of the PCR amplified products were cut with restriction enzyme and ligated together, the gap between primers created a deletion in gp120. The mutants were screened for acquisition of a new restriction site at the site of the deletion, and the gp120 deletions were confirmed by DNA sequencing. The pfastbac DNA was then transposed into bacmid DNA coding for infectious baculovirus. For all loop deletions but one, the mutation was made on the 89.6 background. Since loop B contained multiple critical residues, a IIIB background was used so that it would start with a high binding phenotype.

TABLE 1

Non-overlapping DNA primers

| Loop | Primer pairs | SEQ ID NOS: | Restriction enzyme |
|---|---|---|---|
| A | CTGTGAAATTTATCGATCTAATTACT ATGTCTTC | 23 | Cla I |
|   | TGCTAAATCGATAATAGTACAGCT AAATGAATC | 24 | |
| B | CCATCGATTGCTTAAAGATTATTGT | 35 | Cla I |
|   | CCATCGATTGTAACGCACAGTTTTA | 36 | |
| C | GCCACATATTTGCTAGCTGTTTTATT CTGCATTGGAGTG | 37 | Nhe I |
|   | GGCAGAAAGTAGGGCTAGCAATGTAT GCCCC | 38 | |
| D | ACCTCCATCCCGGGTTAGTAGCAGCC CTG | 39 | Xma I |
|   | GCCCCGGGGCTTCAGACCTGGAGGAG GAGATATG | 40 | |
| E | CTCCTCCCGGGCGGAAGATCTCAGTC TCAG | 41 | Xma I |
|   | CGCCCGGGAGGAGGGGACAATTGGAG AAGTGAATTAT | 42 | |
|   | GGCCCGGGGACAATTGGAGAAGTG | 43 | |

PCR products were cut with the indicated restriction enzyme and ligated together, creating a deletion.

Baculovirus recombinants: Bacmids were transformed into Sf-9 cells (ATG Laboratories, Eden Prairie, Minn.). After 3 to 4 days in culture, cell pellets were suspended in phosphate buffered saline (PBS) at 5×106/ml, sonicated and screened for protein expression by western blot. Positive viruses were plaque purified, screened for protein expression, and expanded to 200 ml of titered baculovirus. Protein expression and purification Hi 5 cells were cultured overnight at 0.8×106 per ml and then infected with titered stocks of baculovirus recombinants at a multiplicity of infection (moi) of 3 to 5:1. After 28 hours on a shaker at 27° C., the infected cells were harvested by centrifugation at 1000 rpm for 10 minutes in a Sorvall RT6000 centrifuge. Preliminary experiments showed that 28 to 30 hours gave the greatest yield, and that most of the protein remained intracellular.

The cell pellet from 200 ml of culture were resuspended in 10 ml PBS and stored frozen at −80 ° C. The cells were thawed, diluted 1:1 with PBS in 0.5% CHAPS plus protease inhibitor cocktail (BD Pharmingen). After 30 minutes at 4° C., they were sonicated for 40 seconds in a Vibra Cell™ sonicator with an external probe, followed by centrifugation for 10 min at 2000 rpm in a TJ-6 desktop centrifuge to remove cell debris. In these HBsAg-gp120 hybrids, HBsAg acts as a carrier protein that assembles and incorporates gp120 into virus-like particles. Ten milliliters of the supernatant was layered onto a discontinuous sucrose gradient, consisting of layers of 10%, 20% and 40% sucrose, and sedimented in a Beckman SW28 rotor for 2⅓ at 27,000 rpm. Fractions of about 0.7 ml each were collected from the bottom of the tube and assayed for gp120 content by ELISA using 2G12 as the primary antibody and goat anti-human IgG conjugated to alkaline phosphatase (MP Biomedicals, Aurora, Ohio), as the detecting reagent. Peak fractions were pooled and diafiltered against PBS.

Antibody binding ELISA assays: Each purified gp120 was serially diluted on enzyme linked immunosorbent assay (ELISA) plates and tested for 2G12 binding. Dilutions that gave approximately 1 optical density (OD) in 20 min were chosen for subsequent experiments. Equivalent amounts of each variant gp120 were coated side by side on an ELISA plate overnight at 4° C. The plates were blocked with 1% BSA, and monoclonal antibodies or CD4-Ig were serially diluted 3-fold, starting at a concentration of 3 μg/ml. After 2 hours at 25° C., the plates were washed, and goat antihuman IgG conjugated alkaline phosphatase was added as second antibody. After another 1½ hours at 25° C., the plates were washed, phosphatase substrate was added, and OD410 measured in an ELISA plate reader. For each gp120 variant, the OD readings for antibody binding were normalized to a time point when peak 2G12 binding was between 1.6 and 2 OD. Differences in apparent affinities were determined by comparing half maximal binding for each gp120 variant. The results must be interpreted carefully, since binding was measured on the solid phase, not in solution, and the antigens are multimeric virus-like particles, which tend to increase the apparent affinity.

Structure modeling and computational analysis: The CD4 bound and unliganded forms of gp120 for the 89.6 strain were modeled based on the crystal structures for HIV and SIV gp120. Sequence alignment between the templates of the crystal structures and strain 89.6 were carried out by using HMAP (Tang et al., *J. Mol. Biol.* 334, 1043-1062, 2003) and then adjusted manually, conserving the overall secondary structure and positioning the residues known to be important in the family. Five out of seven S—S bonds in SIV gp120 are conserved in the unliganded state of 89.6 gp120. The model was built using NEST in the Jackal package (Xiang, *Curr. Protein Pept. Sci.* 7, 217-227, 2006). The gp120 conformation of loop mutants was modeled using the LOOPY program (Xiang et al., *Proc. Natl. Acad. Sci. U.S.A.* 99, 7432-7437, 2002b). All models were subjected to energy minimization using the TINKER minimization protocol under the CHARMM all-atom force field (Mackerell et al., *J. Phys. Chem. B.* 102, 3586-3616, 1998).

Example 2

Molecular Modeling of gp120

This example describes the results of molecular modeling of the gp120 surface loops.

Based on the 3D structure of gp120, five loop structures were identified that surround the CD4 binding site in the liganded conformation and may protect it from antibodies (Table 2).

TABLE 2

Loops surrounding the CD4 binding site

| Loop | Amino acids deleted | gp120 domain | 2° structure |
|---|---|---|---|
| A | 275-282 ENFTDNAK | C2 | B10-β11 |
| B | 366-371 GGDPEI | C3 | β15-α3 |
| C | 424-432 INMWQKVGK | C4 | β20-β21 |
| D | 457-468 DGGNSTETETEI | V5 | £V5-β24 |
| E | 472-476 GGDMR | C5 | Exit loop |

Loops A, B, C and E are located in the conserved regions C2, C3, C4 and C5, respectively, while loop D is in variable region V5. As shown in FIG. 1A, loops A and C are located on the right and left margins of the CD4 binding site in the bound conformation, while loops B and E form the floor and back wall of the site. Loop B has important contact residues for CD4 and for antibodies. Loop C contributes to the bridging sheet that holds together the inner and outer domains in the liganded conformation. The space between loops B and C forms a hydrophobic pocket for CD4 binding. Loop A anchors an oligosaccharide side chain, and removing this group enhances b12 binding moderately. For antibodies that bind this conformation, one or more of the loops may interfere with antibody binding through steric hindrance.

Figure 1B:
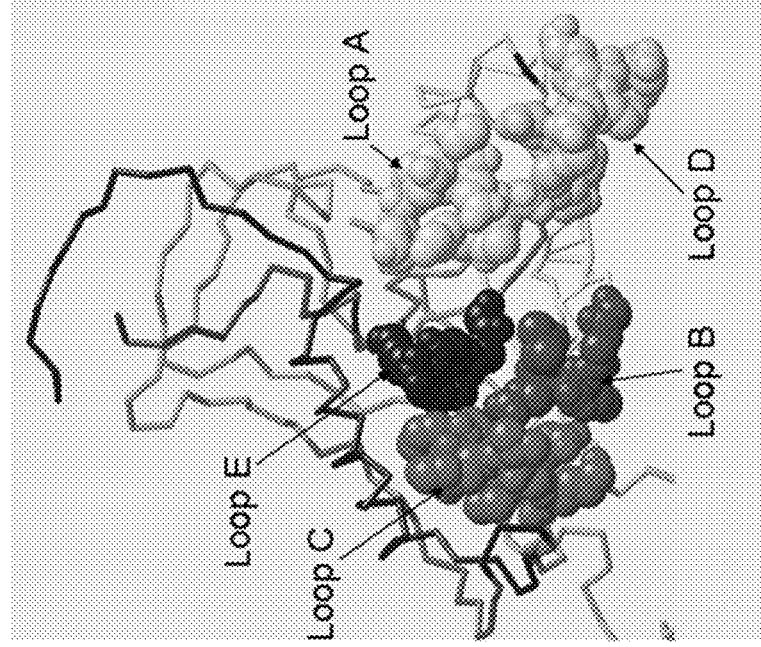

A second conformation of gp120 is the unliganded form, as found on the virus prior to binding its receptor (FIG. 1B). In this structure, loops B and C are located directly in front of the CD4 binding site, where they could interfere with antibody binding by covering up the site. Normally, when gp120 binds its receptor, these loops move out of the way to reveal the CD4 binding pocket. However, by stabilizing the unbound conformation, the loops may prevent the formation and exposure of the CD4 binding site, so antibodies cannot bind.

Example 3

Preparation and Characterization of gp120 Loop Mutants

Because of the potential to affect antibody binding, mutant gp120s that lacked each loop structure were prepared and tested for exposure of the CD4 binding site. Loop deletions were generated in gp120 of either the IIIB or 89.6 background by the QuickChange® method. Since this method introduces a new restriction site at the site of the deletion, the presence of a novel restriction site was confirmed for each mutant (Table 2 and FIG. 2, left panel). For example, digestion from the Sal I restriction site at the 5' end of the expression cassette to the Nhe I restriction site at the loop C deletion, revealed a new restriction fragment at 1.95 kb, as predicted. This was confirmed by sequencing. Similar analysis of the other deletion mutants showed progressively larger restriction fragments for deletion mutants A through E.

The gp120 mutants were expressed in baculovirus recombinants in tandem with HBsAg as described in Berkower et al., *Virology* 321, 75-86, 2004 and Berkower et al. *Virology* 377:330-338, 2008 incorporated herein by reference in its entirety. The HBsAg-gp120 hybrids assembled into gp120-rich virus-like particles, and these were purified by sedimentation at high MW in sucrose gradients.

These partially purified mutant forms of gp120 were expressed at the expected MW, were antigenically pure, and were used in comparable amounts to the wild type gp120, as shown by western blot (FIG. 2B). Each gp120 variant was characterized for binding to a panel of monoclonal antibodies. Monoclonal 2G12 binds N-linked sugars (at Asn 332 and Asn 339) on the opposite side of gp120 from the CD4 binding site. Since its binding was generally unaffected by point mutations in loops A, B, C and E, this was used to define conditions of equal ELISA plate coating for variant and wild type gp120. For example, equal binding of 2G12 was demonstrated for gp120 of the IIIB wild type and its loop B mutant, as well as the 89.6 wild type and its loop C mutant (FIG. 2C). Similar results were obtained using polyclonal HIV immune globulin. In all subsequent tests, various gp120s were tested under conditions of equal plate coating as demonstrated by equal 2G12 binding.

Figure 3B:
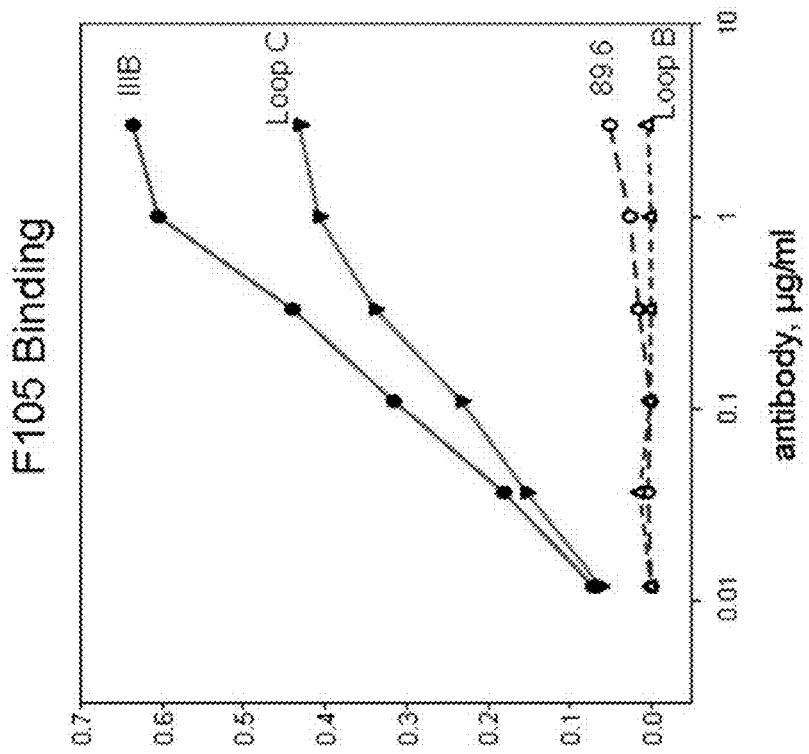
FIGS. 3A and 3B are graphs showing antibody binding to gp120 variants. Monoclonal antibodies b12 (FIG. 3A), and F105 (FIG. 3B) were tested on two gp120s of IIIB type (wild type or loop B deletion) or on two gp120s of the 89.6 type (wild type or loop C deletion). Under conditions of equal plate coating, both monoclonals consistently bound wild type IIIB better than 89.6. Loop B deletion blocked antibody binding completely. Deletion of loop C increased b12 binding 3-fold, to equal IIIB, and enhanced F105 binding by more than 10-fold.
Figure 3A:
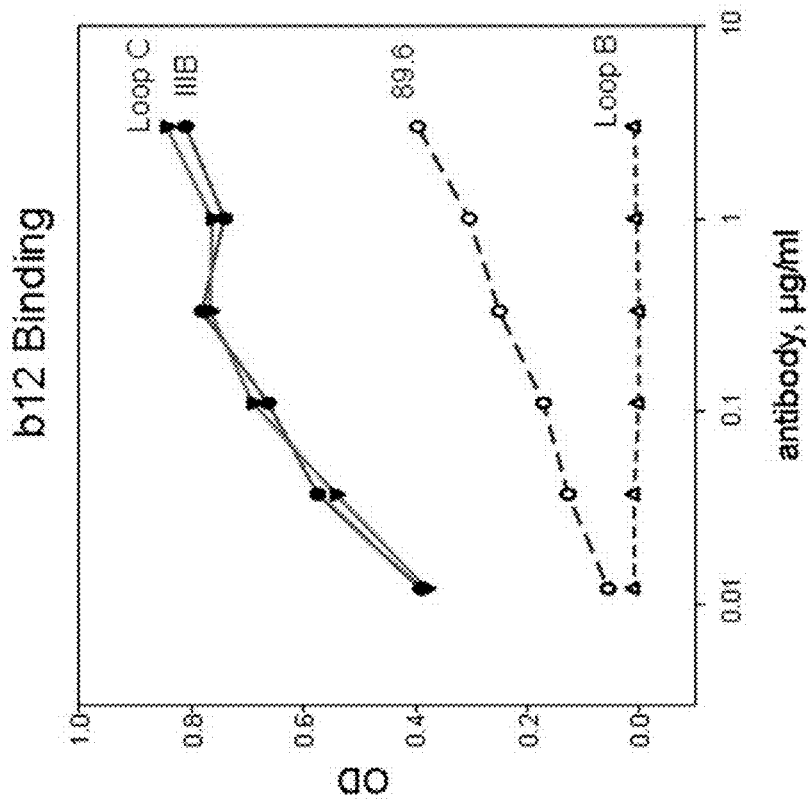
Figure 4A:
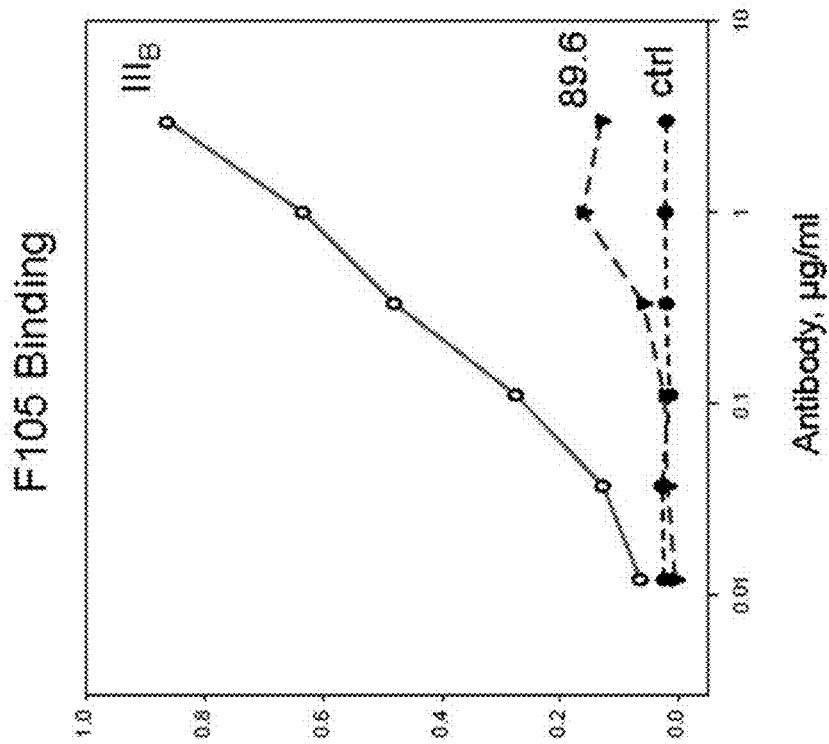
FIGS. 4A and 4B are graphs showing antibody binding to AT-2 inactivated HIV-1 virions of the IIIB type or SHIV virions of the 89.6 type or control microvesicles. Monoclonal antibodies b12 (FIG. 4A) and F105 (FIG. 4B) produced a similar pattern as observed for virus-like particles of the same gp120 type.
Figure 4B:
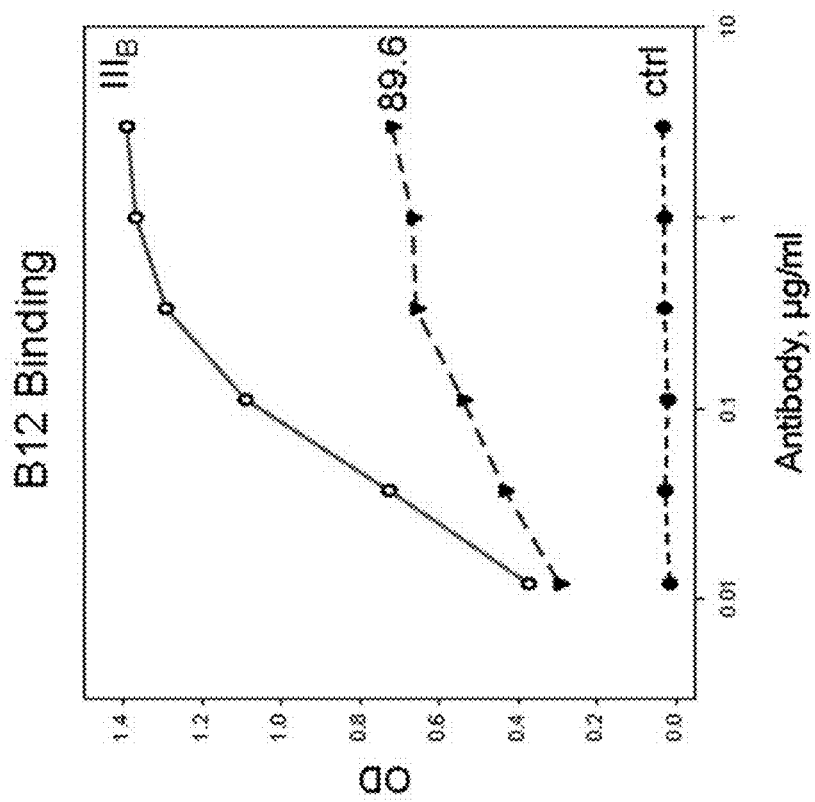

Antibody binding to the CD4BS was measured using two monoclonals, b12 and F105. Both are specific for the CD4 binding site, but their footprints are different, so they could be affected differently by subtle changes in the CD4BS. Monoclonal b12 consistently bound gp120 of the IIIB wild type 2.8 to 4-fold better than gp120 of the 89.6 type (FIG. 3A). This effect was even more pronounced for monoclonal F105 (FIG. 3B), which bound IIIB 8 to 16-fold better than 89.6. Nearly identical results were obtained when the assay was repeated using AT-2 inactivated HIV-1 virions instead of recombinant gp120 particles (FIGS. 4A and 4B). Monoclonal b12 consistently bound IIIB virions better than 89.6 virions, and the effect was even greater for F105, indicating that these differences are an intrinsic property of gp120 and are not an artifact of recombinant gp120 particles. The CD4 binding site may be better exposed for antibody binding in IIIB, which is T cell line adapted, than in 89.6, which is a primary isolate. Strain 89.6 may limit antibody binding by partially concealing this site. As shown in FIGS. 3A and 3B, deletion of loop B completely abrogated binding of both monoclonal antibodies to gp120 of the IIIB type. This result agrees with earlier studies showing that loop B contains critical contact residues for both antibodies, including Gly 366, Gly 367, Asp 368, and Glu 370. X-ray crystallographic results also show that monoclonal b12 and CD4 straddle this loop in the liganded form of gp120.

Deletion of loop C increased b12 binding, as measured by ELISA peak OD, by a mean of 2.6+/−0.37 fold in six experiments. The deletion was made in the 89.6 background, and it increased b12 binding to nearly the same level or equal to IIIB (peak OD between 80 and 100% of the IIIB value).

Figures 5A, 5B:
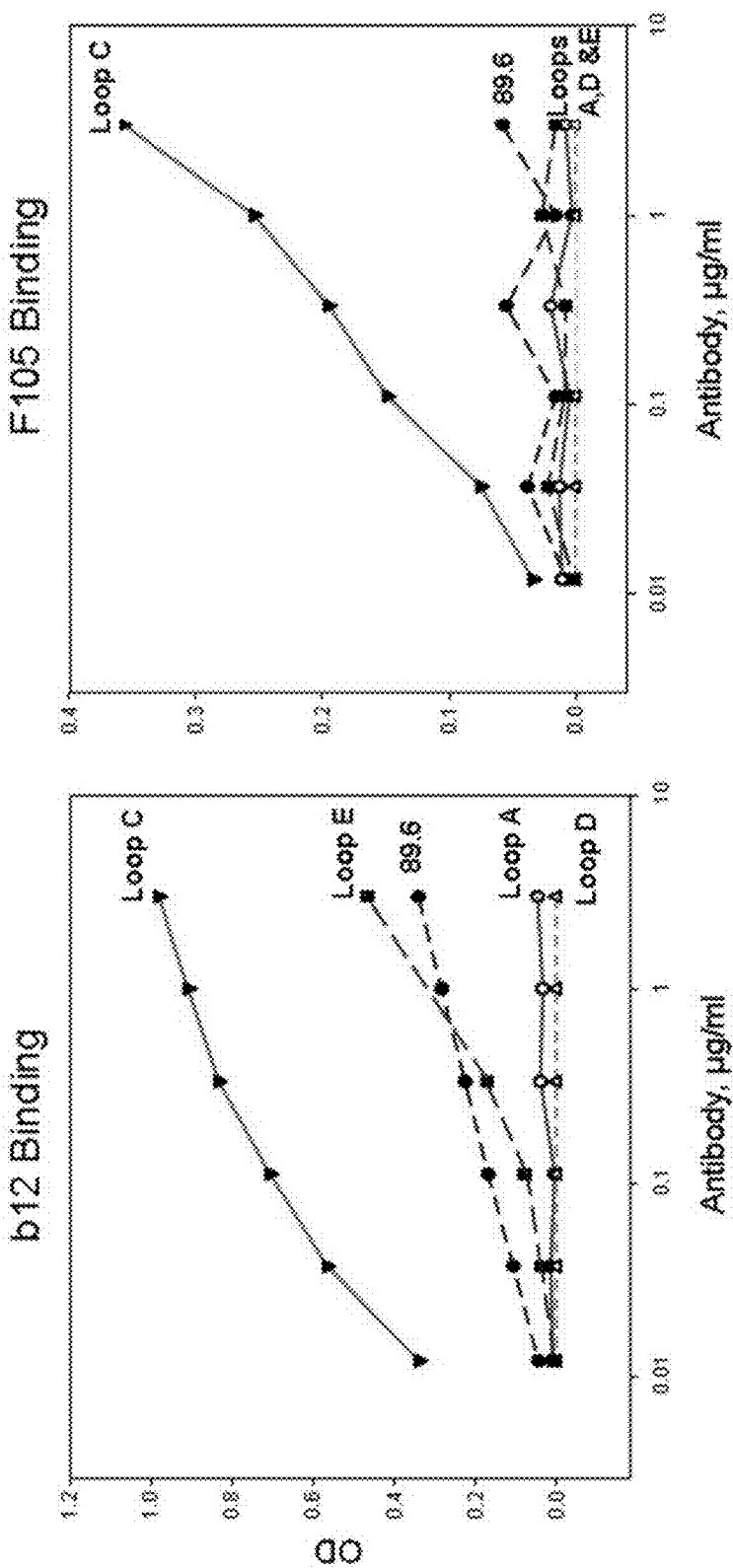
FIGS. 5A and 5B are graphs showing the effect of additional loop deletions on antibody binding. Monoclonal antibodies b12 (FIG. 5A) and F105 (FIG. 5B) showed enhanced binding to loop C deleted gp120, minimal effect on loop E deletion, and markedly reduced binding to loop A or D deleted gp120.

Binding was increased over the entire range of antibody concentrations, from low level binding to saturation. The effect of the loop C deletion on apparent affinity is shown by comparing half maximal binding of the loop C mutant with the concentration of wild type 89.6 needed to reach the same OD. As shown, loop C deletion shifted the b12 binding curve to the left by 300-fold relative to wild type gp120. For F105, the enhanced binding was even greater, as measured by peak OD (FIG. 3B). Deletion of loop C consistently enhanced F105 binding relative to 89.6 wild type by a mean of 7.1+/−2.0 fold in six experiments. The shift in apparent affinity for F105 was greater than 100-fold, and could not be estimated accurately because 89.6 wild type never achieved half maximal binding of the loop C mutant. This result is consistent with X-ray crystallography of b12 bound to gp120, showing that essential contact residues are not located within loop C. The fact that antibody binding to 89.6 envelope was restored by a deletion indicates that wild type 89.6 does not lack contact residues for antibody binding. The mechanism that allowed 89.6 to evade these two neutralizing antibodies was reversed by the deletion of just nine conserved amino acids in loop C. Deletion of loops A or D resulted in mutant gp120s that failed to bind either monoclonal, b12 or F105 (FIGS. 5A and 5B). The effect of the loop A deletion was much greater than the generally modest effects (including enhancement) of single amino acid substitutions in the same loop, while loop D includes residues that were identified as critical by the substitution method. Deletion of three amino acids at loop E (Asp-Met-Arg) had no effect on b12 binding but inhibited F105 completely, and both findings agree with the effect of multiple Ala substitutions at the same site. The different effects of loop E modification on these two monoclonals may reflect their different binding footprints within the CD4BS. The binding of each gp120 variant to a multimeric form of CD4-Ig that could detect binding even at low affinity was measured.

Figure 6A:
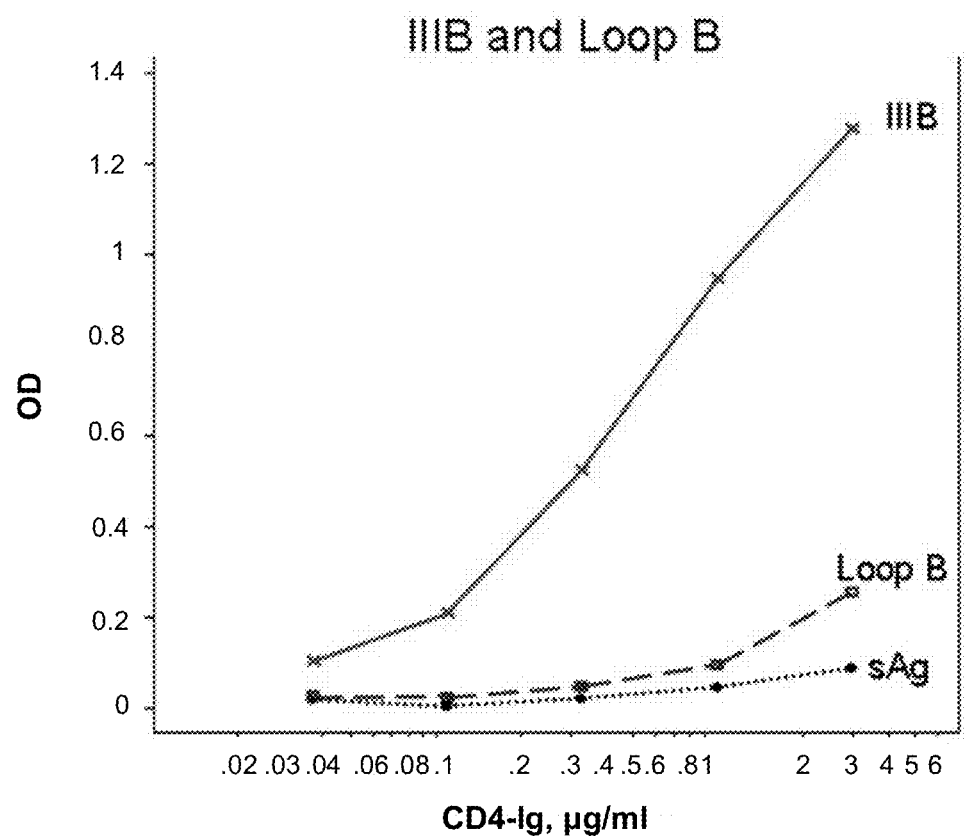
FIGS. 6A and 6B are graphs showing CD4-Ig binding measured for gp120 of the IIIB type and its loop B deletion (FIG. 6A) or 89.6 with deletion of loops A, C or D (FIG. 6B). Deletion of loop B reduced CD4-Ig binding to the level of the HBsAg control. The other loop deletions had little or no effect on CD4-Ig binding.
Figure 6B:
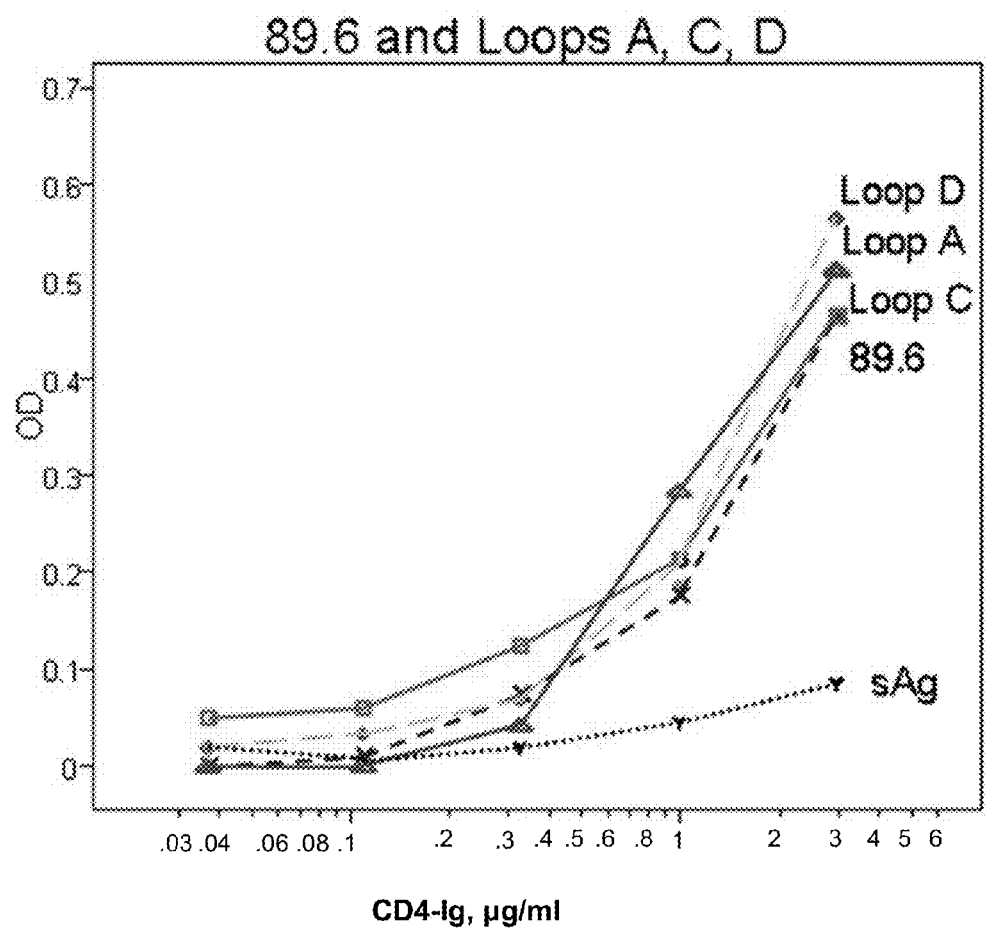

Deletion of loop B, on the IIIB background, gave complete loss of CD4-Ig binding (FIG. 6A), which was nearly as low as the HBsAg control. Deletion of loops A, C, or D on the 89.6 background had little or no effect on CD4-Ig binding (FIG. 6B). Some loop deletions, such as loop B, had negative effects on both antibody and CD4 binding, while others, such as loops A and D, inhibited one but not the other. Loop C enhanced antibody binding without affecting CD4, even though both ligands bind within the same binding pocket on gp120. The CD4 bound form of wild type gp120 (strain 89.6) and the loop C mutant were modeled based on the crystal structures of gp120 from HIV-1 IIIB and SIV.

Figures 7A, 7B, 7C:
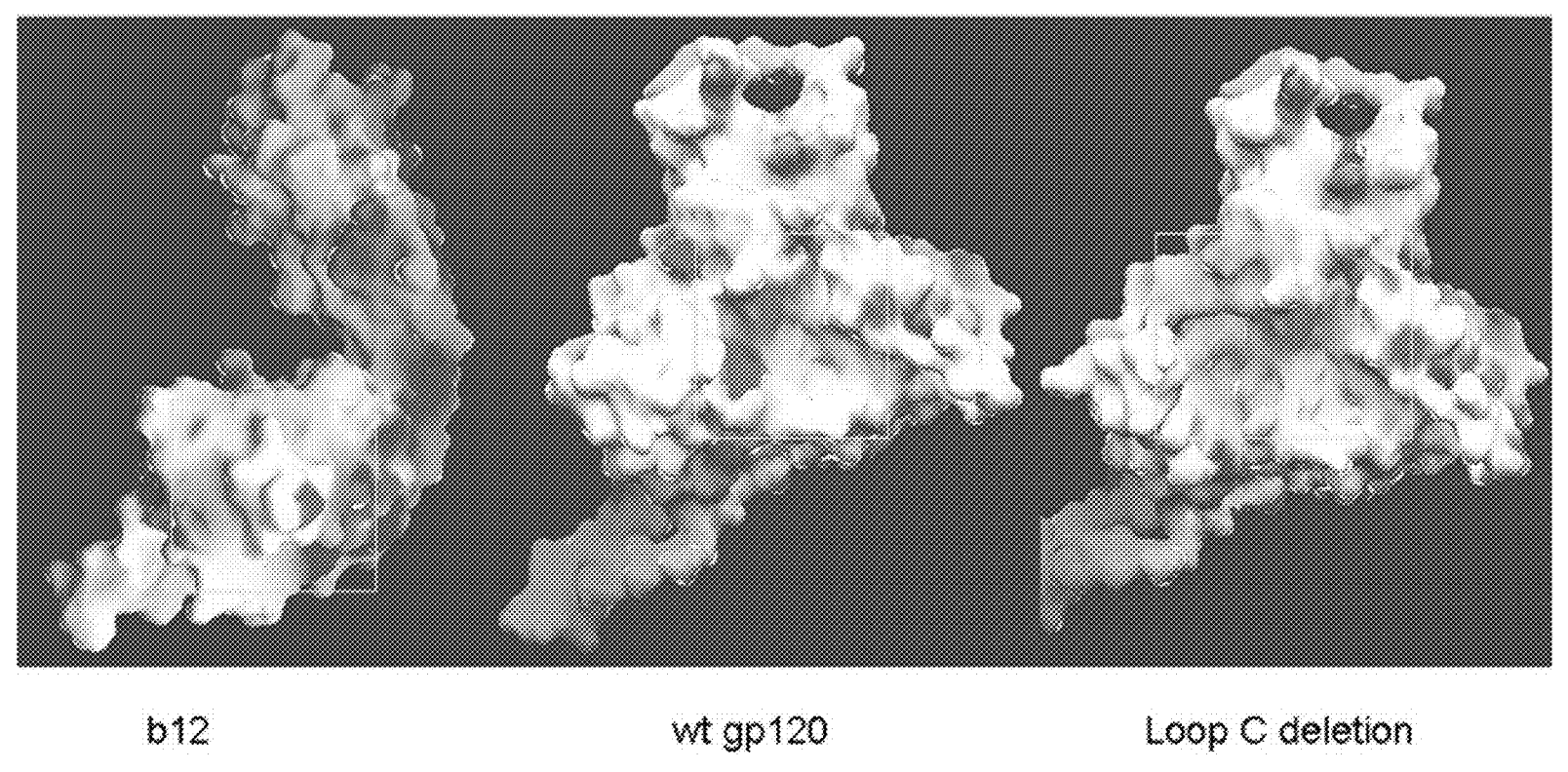

Computational analysis of surface charge distribution indicated that hydrophobic and electrostatic interactions were the driving force for the binding between gp120 and its ligands. As shown for monoclonal b12 (FIG. 7A), the gp120-binding sites on CD4, b12, and F105 were mainly hydrophobic to slightly positive charged, while the binding pocket on gp120 was hydrophobic to slightly negative charged (FIG. 7B). Deletion at loop C exposed the CD4 binding pocket beyond normal for the bound conformation and increased its hydrophobicity (see FIG. 7), both of which increased ligand binding. In addition, deletion of loop C may destabilize the unliganded conformation by exposing a large hydrophobic cavity (radius 6.5 Å) that is destabilized by water molecules trapped inside.

Example 4

Treatment of HIV in a Human Subject

This example describes a particular method that can be used to treat HIV in a human subject by administration of one or more compositions that includes an effective amount of any of the disclosed isolated immunogens. Although particular methods, dosages, and modes of administrations are provided, one skilled in the art will appreciate that variations can be made without substantially affecting the treatment.

Based upon the teaching disclosed herein, HIV, such as HIV type 1, can be treated by administering a therapeutically effective amount of a composition that includes variant gp120 polypeptide to reduce or eliminate HIV infection, replication or a combination thereof. The method can include screening subjects to determine if they are HIV sero-positive, for example infected with HIV-1. Subjects having HIV infection are selected. In one example, subjects having increased levels of HIV antibodies in their blood (as detected with an enzyme-linked immunosorbent assay, Western blot, immunofluorescence assay, or nucleic acid testing, including viral RNA or proviral DNA amplification methods) are selected. In one example, a clinical trial would include half of the subjects following the established protocol for treatment of HIV (such as a highly active antiretroviral therapy). The other half would follow the established protocol for treatment of HIV (such as treatment with highly active antiretroviral compounds) in combination with administration of the compositions including variant gp120 polypeptide (as described herein). In another example, a clinical trial would include half of the subjects following the established protocol for treatment of HIV (such as a highly active antiretroviral therapy). The other half would receive a composition including the variant gp120 polypeptide, alone or in combination with HBsAgs or variant HBsAgs (such as virus-like particles including HBsAgs or any of the variant HBsAgs disclosed in U.S. Provisional application 61/086,098, filed on Aug. 4, 2008, which is incorporated herein by reference in its entirety, such as variant HBsAg TM16, variant HBsAg TM20, variant HBsAg MPRS, variant DA31-34, variant DA31-32F, variant TM16+20, variant TM16+31/34 or any combination thereof).

Screening Subjects

In particular examples, the subject is first screened to determine if they are infected with HIV. Examples of methods that can be used to screen for HIV infection include a combination of measuring a subject's CD4+ T cell count and the level of HIV in serum blood levels or determine whether a subject is sero-positive for HIV antibodies.

In some examples, HIV testing consists of initial screening with an enzyme-linked immunosorbent assay (ELISA) to detect antibodies to HIV, such as to HIV-1. Specimens with a nonreactive result from the initial ELISA are considered HIV-negative unless new exposure to an infected partner or partner of unknown HIV status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV infection. Specimens that are repeatedly ELISA-reactive and occasionally provide an indeterminate Western blot result, which may be either an incomplete antibody response to HIV in an infected person, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV in a subject's blood is also indicative that the subject has HIV and is a candidate for receiving the therapeutic compositions disclosed herein. Moreover, detection of a CD4+ T cell count below 350 per microliter, such as 200 cells per microliter, suggests that the subject is likely to have HIV.

Pre-screening is not required prior to administration of the therapeutic compositions disclosed herein.

Pre-Treatment of Subjects

In particular examples, the subject is treated prior to administration of a therapeutic composition that includes one or more of the disclosed variant gp120 polypeptide either alone or in combination with a HBsAg or variant thereof. However, such pre-treatment is not always required, and can be determined by a skilled clinician. For example, the subject can be treated with an established protocol for treatment of HIV (such as a highly active antiretroviral therapy).

Administration of Therapeutic Compositions

Following subject selection, a therapeutic effective dose of the composition including variant gp120 polypeptide, alone or in combination with HBsAgs or variant HBsAgs (such as virus-like particles including HBsAgs or any of the variant HBsAgs disclosed in U.S. Provisional application 61/086, 098, filed Aug. 4, 2008 or naturally occurring variants) is administered to the subject (such as an adult human or a newborn infant either at risk for contracting HIV or known to be infected with HIV). Administration induces a sufficient immune response to reduce viral load, to prevent or lessen a later infection with the virus, or to reduce a sign or a symptom of HIV infection. Additional agents, such as anti-viral agents, can also be administered to the subject simultaneously or prior to or following administration of the disclosed compositions. Administration can be achieved by any method known in the art, such as oral administration, inhalation, intravenous, intramuscular, intraperitoneal, or subcutaneous.

In some particular examples, the composition includes a variant HBsAg with one or more transmembrane domains of the HBsAg replaced with a gp41 antigenic insert. The gp41 antigenic insert includes (a) an antigenic polypeptide fragment of gp41, such as an antigenic polypeptide gp41 fragment with the amino acid sequence of SEQ ID NO: 1, and (b) a transmembrane spanning region of gp41, such as a transmembrane spanning gp41 region with the amino acid sequence set forth in SEQ ID NO: 25 (in which wherein $X_1$, $X_2$ and $X_3$ are any amino acid $X_4$, $X_5$, and $X_6$ are any hydrophobic amino acid). In one example, the antigenic polypeptide fragment of gp41 is between 28 and 150 amino acids in length and the membrane spanning region of gp41 is between 22 and 40 amino acids in length.

In one particular example, the composition includes a variant HBsAg in which the first transmembrane spanning domain of the HBsAg is replaced by a gp41 antigenic insert. For example, the gp41 antigenic insert replaces amino acid residues 1-35 of SEQ ID NO: 31. In another example, the gp41 antigenic insert replaces amino acid residues 1-32 of SEQ ID NO: 31. In yet another example, the gp41 antigenic insert replaces amino acid residues 1-29 of SEQ ID NO: 31. In further examples, the composition includes a variant HBsAg in which the first transmembrane spanning domain of the HBsAg is replaced by a gp41 antigenic insert has the amino acid sequence set forth as SEQ ID NO: 29.

In another particular example, the composition includes includes a variant HBsAg in which the third transmembrane spanning domain of the HBsAg is replaced by a gp41 antigenic insert. For example, the gp41 antigenic insert replaces amino acid residues 150-190 of SEQ ID NO: 31. In another example, the gp41 antigenic insert replaces amino acid residues 153-187 of SEQ ID NO: 31. In yet another example, the gp41 antigenic insert replaces amino acid residues 156-185 of SEQ ID NO: 31. In a further example, the composition includes a variant HBsAg in which the third transmembrane spanning domain of the HBsAg is replaced by a gp41 antigenic insert has the amino acid sequence set forth as SEQ ID NO: 44.

In an even more particular example, the composition includes a variant HBsAg in which the first and the third transmembrane spanning domains of the HBsAg are replaced by a gp41 antigenic insert. For example, the gp41 antigenic insert replaces amino acid residues 1-35 and 150-190 of SEQ ID NO: 31. In another example, the gp41 antigenic insert replaces amino acid residues 1-32 and 153-187 of SEQ ID NO: 31. In yet another example, the gp41 antigenic insert replaces amino acid residues 1-29 and 156-185 of SEQ ID NO: 31. In a particular example, the the composition includes a variant HBsAg in which the third transmembrane spanning domain of the HBsAg is replaced by a gp41 antigenic insert has the amino acid sequence set forth as SEQ ID NO: 45.

In additional examples, the composition includes variant HBsAgs with a gp41 transmembrane spanning domain inserted into the first domain and third domain of the HBsAgs. In another example, the composition includes variant HBsAgs with at least one MPR inserted into the HBsAg in between the second domain and third domain. In additional examples, the composition includes a combination of the disclosed variant HBsAgs, such as variant HBsAgs with a gp41 antigenic insert (including a gp41 transmembrane domain and MPR) replacing the first and third domain of the HBsAg (variant HBsAg TM16+TM20) and variant HBsAgs with a gp41 antigenic insert (a gp41 transmembrane domain and MPR) replacing the first domain of the HBsAg and a MPR in between the second and third transmembrane domains (TM16+31/34). In other examples, the composition includes isolated nucleic acid molecules encoding a variant gp120 polypeptide, a HBsAg or variant thereof or viral-like particles including a variant gp120-HBsAg hybrid or variant gp120-variant HBsAg hybrid.

The amount of the composition administered to prevent, reduce, inhibit, and/or treat HIV or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly, or monthly repeated administration protocol). In one example, therapeutic compositions that include variant gp120 polypeptide, alone or in combination with HBsAgs or variant HBsAgs, are administered intravenously to a human. As such, these compositions may be formulated with an inert diluent or with a pharmaceutically acceptable carrier.

In one specific example, a composition including variant gp120 polypeptide, alone or in combination with HBsAgs or variant HBsAgs, is administered intravenously from 0.1 pg to about 100 mg per kg per day. In an example, the composition is administered continuously. In another example, the composition is administered at 50 μg per kg given twice a week for 2 to 3 weeks. Administration of the therapeutic compositions can be taken long term (for example over a period of months or years).

Assessment

Following the administration of one or more therapies, subjects having HIV (for example, HIV-1 or HIV-2) can be monitored for reductions in HIV levels, increases in a subjects CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 5

Method of Monitoring Serum Antibodies to HIV

This example illustrates the methods of monitoring serum antibodies to HIV.

Based upon the teachings disclosed herein, the presence of serum antibodies to HIV can be monitored using the isolated immunogens disclosed herein, such as to detect an HIV infection. Generally, the method includes contacting a sample from a subject, such as, but not limited to a blood, serum, plama, urine or sputum sample from the subject with one or more of the variant gp120 polypeptide and detecting binding of antibodies in the sample to the variant gp120 polypeptide. The binding can be detected by any means known to one of skill in the art, including the use of labeled secondary antibodies that specifically bind the antibodies from the sample. Labels include radiolabels, enzymatic labels, and fluorescent labels.

Example 6

Binding of HIVIgG and Human Sera from HIV-1 Positive Patients to Disclosed Variant gp120 Peptides Based upon the teaching herein, the utility of variant gp120 polypeptides to identify sera that contain neutralizing antibodies against gp120 can be determined by screening a set of weakly and broadly neutralizing human HIV-1 positive sera and HIV-IgG for binding to variant gp120 polypeptides or virus like particles that include variant gp120 polypeptides. Human sera from HIV-1 positive patients and antibody 2F5 can be serially diluted and analyzed for binding to variant gp120 polypeptides and particles containing such polypeptides in ELISA format.

Example 7

Immunization of Rabbits with Variant gp120 Particles

Based upon the teaching herein, rabbits are immunized with 5, 20, 50 and 100 μg of the disclosed variant gp120 polypeptide or virus like particles containing the gp120 polypeptides in ALUM and CpG as adjuvant by intramuscular route. The rabbit sera is analyzed for binding to b12 or F105 epitope-containing peptide by ELISA. In addition, the sera can be checked for their neutralizing ability in a viral neutralization assay using sensitive HIV-1 strains and chimeric HIV-2 strains containing HIV-1 b12 or F105 epitope. If the rabbits are immunized to variant gp120 polypeptides, then a high titer of antibodies will be raised to an b12 or F105 epitope.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. An isolated immunogen comprising a variant gp120 polypeptide, wherein the variant gp120 polypeptide has a deletion of at least 8 consecutive amino acid residues of the fourth conserved loop (C4) between residues 423 and 433, wherein said numbering is based upon the prototypic HIV-1 isolate HXB2, wherein the deletion reveals a cryptic CD4 binding site epitope.

2. The isolated immunogen of claim 1, wherein residues 424-432 of gp120 are deleted.

3. The isolated immunogen of claim 1, wherein the sequence consisting of the amino acid sequence INMWQKVGK (residues 424 to 432 of SEQ ID NO: 47) is deleted.

4. The isolated immunogen of claim 1, wherein the immunogen comprises the amino acid sequence according to SEQ ID NO: 50.

5. A composition comprising the isolated immunogen of claim 1.

6. The composition of claim 5, further comprising a carrier protein.

7. The composition of claim 6, wherein the carrier protein is a hepatitis B surface antigen or a variant thereof.

8. The composition of claim 7, wherein the carrier protein is covalently linked to the hepatitis B surface antigen or variant thereof.

9. A viral-like particle comprising the isolated immunogen of claim 1.

10. The viral-like particle of claim 9, further comprising at least one TLR ligand.

* * * * *